US012364763B2

(12) United States Patent
De Fougerolles et al.

(10) Patent No.: US 12,364,763 B2
(45) Date of Patent: *Jul. 22, 2025

(54) DELIVERY AND FORMULATION OF ENGINEERED NUCLEIC ACIDS

(71) Applicant: ModernaTX, Inc., Cambridge, MA (US)

(72) Inventors: Antonin De Fougerolles, Waterloo (BE); Sayda M. Elbashir, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/820,652

(22) Filed: Aug. 30, 2024

(65) Prior Publication Data

US 2025/0090667 A1 Mar. 20, 2025

Related U.S. Application Data

(60) Continuation of application No. 18/417,715, filed on Jan. 19, 2024, which is a continuation of application No. 17/141,753, filed on Jan. 5, 2021, now Pat. No. 11,911,474, which is a continuation of application No. 15/927,730, filed on Mar. 21, 2018, now Pat. No. 10,898,574, which is a continuation of application No. 15/379,284, filed on Dec. 14, 2016, now Pat. No. 9,950,068, which is a division of application No. 14/337,513, filed on Jul. 22, 2014, now Pat. No. 9,533,047, which is a continuation of application No. 13/897,362, filed on May 18, 2013, now abandoned, which is a continuation of application No. 13/437,034, filed on Apr. 2, 2012, now Pat. No. 8,710,200.

(60) Provisional application No. 61/470,451, filed on Mar. 31, 2011.

(51) Int. Cl.

| | |
|---|---|
| ***A61K 47/18*** | (2017.01) |
| ***A61K 31/7088*** | (2006.01) |
| ***A61K 31/7115*** | (2006.01) |
| ***A61K 38/19*** | (2006.01) |
| ***A61K 38/48*** | (2006.01) |
| ***A61K 47/22*** | (2006.01) |
| ***A61K 47/28*** | (2006.01) |
| ***A61K 48/00*** | (2006.01) |
| ***C07K 14/535*** | (2006.01) |
| ***C12N 9/64*** | (2006.01) |
| ***C12N 15/67*** | (2006.01) |
| ***C12N 15/87*** | (2006.01) |

(52) U.S. Cl.

CPC .......... *A61K 47/18* (2013.01); *A61K 31/7088* (2013.01); *A61K 31/7115* (2013.01); *A61K 38/193* (2013.01); *A61K 38/4846* (2013.01); *A61K 47/22* (2013.01); *A61K 47/28* (2013.01); *C07K 14/535* (2013.01); *C12N 9/644* (2013.01); *C12N 15/67* (2013.01); *C12N 15/87* (2013.01); *A61K 48/00* (2013.01); *C12N 2310/335* (2013.01)

(58) Field of Classification Search

None

See application file for complete search history.

(56) References Cited

U.S. PATENT DOCUMENTS

| | | | |
|---|---|---|---|
| 5,034,506 | A | 7/1991 | Summerton et al. |
| 5,426,180 | A | 6/1995 | Kool |
| 5,489,677 | A | 2/1996 | Sanghvi et al. |
| 5,512,439 | A | 4/1996 | Hornes et al. |
| 5,591,722 | A | 1/1997 | Montgomery et al. |
| 5,637,459 | A | 6/1997 | Burke et al. |
| 5,639,873 | A | 6/1997 | Barascut et al. |
| 5,641,400 | A | 6/1997 | Kaltenbach et al. |
| 5,789,578 | A | 8/1998 | Burton et al. |
| 5,808,039 | A | 9/1998 | Reddy et al. |
| 5,989,911 | A | 11/1999 | Fournier et al. |
| 6,022,715 | A | 2/2000 | Merenkova et al. |
| 6,022,737 | A | 2/2000 | Niven et al. |
| 6,248,268 | B1 | 6/2001 | Cook |
| 6,303,378 | B1 | 10/2001 | Bridenbaugh et al. |
| 6,423,492 | B1 | 7/2002 | Harbron |
| 6,511,832 | B1 | 1/2003 | Guarino et al. |
| 6,521,411 | B2 | 2/2003 | Hecker et al. |
| 7,691,569 | B2 | 4/2010 | Wohlgemuth et al. |
| 8,075,780 | B2 | 12/2011 | Pearce |
| 8,093,367 | B2 | 1/2012 | Kore et al. |
| 8,664,194 | B2 | 3/2014 | de Fougerolles et al. |
| 8,680,069 | B2 | 3/2014 | de Fougerolles et al. |
| 8,691,750 | B2 | 4/2014 | Constien et al. |
| 8,710,200 | B2 | 4/2014 | Schrum et al. |
| 8,716,465 | B2 | 5/2014 | Rossi et al. |

(Continued)

FOREIGN PATENT DOCUMENTS

| | | | |
|---|---|---|---|
| CA | 2028849 | A1 | 9/1991 |
| CA | 2473135 | A1 | 6/2003 |

(Continued)

OTHER PUBLICATIONS

U.S. Appl. No. 61/404,413, Afeyan et al.

(Continued)

*Primary Examiner* — Robert M Kelly

(74) *Attorney, Agent, or Firm* — Clark & Elbing LLP

(57) ABSTRACT

Provided are formulations, compositions and methods for delivering biological moieties such as modified nucleic acids into cells to modulate protein expression. Such compositions and methods include the delivery of biological moieties, and are useful for production of proteins.

2 Claims, 20 Drawing Sheets

Specification includes a Sequence Listing.

(56) References Cited

U.S. PATENT DOCUMENTS 8,802,438 B2 8/2014 Rossi et al.
8,822,663 B2 9/2014 Schrum et al.
8,883,506 B2 11/2014 Rossi et al.
8,898,864 B1 12/2014 Porter
8,969,353 B2 3/2015 Mahon et al.
8,980,864 B2 3/2015 Hoge et al.
8,999,380 B2 4/2015 Bancel et al.
9,050,297 B2 6/2015 Chakraborty et al.
9,061,059 B2 6/2015 Chakraborty et al.
9,089,604 B2 7/2015 Chakraborty et al.
9,095,552 B2 8/2015 Chakraborty et al.
9,107,886 B2 8/2015 Chakraborty et al.
9,114,113 B2 8/2015 Chakraborty et al.
9,149,506 B2 10/2015 Chakraborty et al.
9,428,535 B2 8/2016 de Fougerolles et al.
9,533,047 B2 1/2017 de Fougerolles et al.
9,675,668 B2 6/2017 Bancel et al.
9,803,177 B2 10/2017 Rossi et al.
9,872,900 B2 1/2018 Ciaramella et al.
9,950,068 B2 4/2018 De Fougerolles et al.
10,022,435 B2 7/2018 Ciaramella et al.
10,064,935 B2 9/2018 Ciaramella et al.
10,286,086 B2 5/2019 Roy et al.
10,463,751 B2 11/2019 De Fougerolles et al.
10,501,513 B2 12/2019 De Fougerolles et al.
10,577,403 B2 3/2020 De Fougerolles et al.
10,898,574 B2 1/2021 de Fougerolles et al.
10,925,935 B2 2/2021 Chakraborty et al.
2001/0025097 A1 9/2001 Sheridan et al.
2002/0001812 A1 1/2002 Smith et al.
2002/0016450 A1 2/2002 Laugharn et al.
2002/0062017 A1 5/2002 Hecker et al.
2002/0114784 A1 8/2002 Li et al.
2002/0130430 A1 9/2002 Castor
2002/0153312 A1 10/2002 Gjerde et al.
2002/0164635 A1 11/2002 Salerno
2003/0120035 A1 6/2003 Gao et al.
2003/0170876 A1 9/2003 Widner et al.
2003/0170891 A1 9/2003 McSwiggen
2003/0180779 A1 9/2003 Lofton-Day et al.
2004/0038278 A1 2/2004 Tzertzinis et al.
2004/0142433 A1 7/2004 Padgett et al.
2004/0220127 A1 11/2004 Sternberg et al.
2004/0259097 A1 12/2004 De Backer et al.
2005/0003496 A1 1/2005 McGall et al.
2005/0130196 A1 6/2005 Hofstadler et al.
2006/0058266 A1 3/2006 Manoharan et al.
2006/0121441 A1 6/2006 Spira
2006/0223081 A1 10/2006 Jarrell et al.
2007/0020678 A1 1/2007 Ault-Riche et al.
2007/0037148 A1 2/2007 Fong et al.
2007/0037770 A1 2/2007 Gryaznov et al.
2007/0244062 A1 10/2007 Laux et al.
2007/0281336 A1 12/2007 Jendrisak et al.
2008/0076910 A1 3/2008 Takkellapati et al.
2008/0171711 A1 7/2008 Hoerr et al.
2008/0274463 A1 11/2008 Chen et al.
2008/0311140 A1 12/2008 Lee et al.
2009/0215125 A1 8/2009 Reed et al.
2009/0264511 A1 10/2009 de Fougerolles et al.
2009/0286852 A1 11/2009 Kariko et al.
2010/0015232 A1 1/2010 Besenbacher et al.
2010/0047261 A1 2/2010 Hoerr et al.
2010/0086922 A1 4/2010 Bryant et al.
2010/0159456 A1 6/2010 Albitar
2010/0178272 A1 7/2010 Hartmann et al.
2010/0183639 A1 7/2010 Uhlmann et al.
2010/0255574 A1 10/2010 Rosen et al.
2010/0261228 A1 10/2010 Gharib et al.
2010/0261231 A1 10/2010 Kore et al.
2010/0317532 A1 12/2010 Liu et al.
2011/0130440 A1 6/2011 Manoharan et al.
2011/0143397 A1 6/2011 Kariko et al.
2011/0218170 A1 9/2011 Thottassery et al.
2011/0244026 A1 10/2011 Guild et al.
2011/0281938 A1 11/2011 Schaub et al.
2012/0046346 A1 2/2012 Rossi et al.
2012/0100136 A1 4/2012 Patel et al.
2012/0129261 A1 5/2012 Eberwine et al.
2012/0251618 A1 10/2012 Schrum et al.
2012/0309053 A1 12/2012 Wellings
2013/0046083 A1 2/2013 Brown et al.
2013/0046084 A1 2/2013 Brown et al.
2013/0052721 A1 2/2013 Hollander et al.
2013/0058894 A1 3/2013 Maldonado et al.
2013/0115272 A1 5/2013 de Fougerolles et al.
2013/0115274 A1 5/2013 Knopov et al.
2013/0123481 A1 5/2013 de Fougerolles et al.
2013/0156849 A1 6/2013 de Fougerolles et al.
2013/0165504 A1 6/2013 Bancel et al.
2013/0197068 A1 8/2013 Kariko et al.
2013/0203115 A1 8/2013 Schrum et al.
2013/0244282 A1 9/2013 Schrum et al.
2013/0245103 A1 9/2013 de Fougerolles et al.
2013/0245105 A1 9/2013 de Fougerolles et al.
2013/0245106 A1 9/2013 De Fougerolles et al.
2013/0251618 A1 9/2013 Li et al.
2013/0259923 A1 10/2013 Bancel et al.
2013/0259924 A1 10/2013 Bancel et al.
2014/0010861 A1 1/2014 Bancel et al.
2014/0105964 A1 4/2014 Bancel et al.
2014/0105966 A1 4/2014 Bancel et al.
2014/0147454 A1 5/2014 Chakraborty et al.
2014/0200261 A1 7/2014 Hoge et al.
2014/0206752 A1 7/2014 Afeyan et al.
2014/0206852 A1 7/2014 Hoge et al.
2014/0243399 A1 8/2014 Schrum et al.
2014/0273230 A1 9/2014 Chen et al.
2014/0275227 A1 9/2014 Hoge et al.
2014/0343129 A1 11/2014 de Fougerolles et al.
2014/0371302 A1 12/2014 Afeyan et al.
2015/0005372 A1 1/2015 Hoge et al.
2015/0017211 A1 1/2015 de Fougerolles et al.
2015/0030576 A1 1/2015 Bancel
2015/0050354 A1 2/2015 Bouchon et al.
2015/0050738 A1 2/2015 Ozsolak et al.
2015/0051268 A1 2/2015 Bancel et al.
2015/0056253 A1 2/2015 Bancel et al.
2015/0064235 A1 3/2015 Bancel et al.
2015/0064236 A1 3/2015 Bancel et al.
2015/0064725 A1 3/2015 Schrum et al.
2015/0086614 A1 3/2015 Bancel et al.
2015/0111248 A1 4/2015 Bancel et al.
2015/0140120 A1 5/2015 McCauley et al.
2015/0141269 A1 5/2015 Soldatov et al.
2015/0141499 A1 5/2015 Bancel et al.
2015/0166616 A1 6/2015 Bancel et al.
2015/0167017 A1 6/2015 Roy et al.
2015/0211039 A1 7/2015 Wang et al.
2015/0307542 A1 10/2015 Roy et al.
2016/0017313 A1 1/2016 Spivak et al.
2016/0024140 A1 1/2016 Issa et al.
2016/0024141 A1 1/2016 Issa et al.
2016/0024492 A1 1/2016 Issa et al.
2016/0024547 A1 1/2016 Bancel et al.
2016/0032273 A1 2/2016 Shahrokh et al.
2016/0038612 A1 2/2016 Hoge et al.
2016/0177295 A1 6/2016 Rudolph et al.
2016/0194368 A1 7/2016 Hoge et al.
2016/0194625 A1 7/2016 Hoge et al.
2016/0237108 A1 8/2016 Fraley et al.
2016/0244742 A1 8/2016 Linnarsson et al.
2016/0326575 A1 11/2016 Von Der Mulbe et al.
2016/0354490 A1 12/2016 Roy et al.
2016/0354491 A1 12/2016 Roy et al.
2016/0354492 A1 12/2016 Roy et al.
2016/0354493 A1 12/2016 Roy et al.
2016/0367702 A1 12/2016 Hoge et al.
2017/0088888 A1 3/2017 El-Sagheer et al.
2017/0136131 A1 5/2017 Roy et al.

(56) References Cited

U.S. PATENT DOCUMENTS

2017/0136132 A1 5/2017 Roy et al.
2017/0175129 A1 6/2017 Roy et al.

FOREIGN PATENT DOCUMENTS

EP 0366400 A2 5/1990
EP 1083232 B1 2/2005
EP 1611899 A1 1/2006
EP 1619254 A1 1/2006
EP 1383556 B9 3/2008
EP 1831160 B1 6/2010
EP 2092064 B1 9/2010
EP 2377938 A1 10/2011
EP 2484770 A1 8/2012
EP 2188379 B1 1/2013
EP 2548960 A1 1/2013
EP 3112467 A1 1/2017
EP 2510099 B1 8/2017
EP 3287525 A1 2/2018
EP 2578685 B1 4/2019
EP 2622064 B1 5/2019
EP 3492109 A1 6/2019
EP 3590949 A1 1/2020
EP 3682905 B1 12/2021
EP 2791160 B1 3/2022
EP 3611266 B1 11/2022
JP 2010530245 A 9/2010
JP 2010280714 A 12/2010
JP 2011-130725 A 7/2011
JP 2014-530601 A 11/2014
JP 2015-513912 A 5/2015
JP 2018-166528 A 11/2018
RU 2540017 C2 1/2015
WO WO-91/05058 A1 4/1991
WO WO-93/03052 A1 2/1993
WO WO-93/13121 A1 7/1993
WO WO-98/05673 A1 2/1998
WO WO-99/14346 A2 3/1999
WO WO-00/42175 A1 7/2000
WO WO-200155306 A2 8/2001
WO WO-02/44399 A2 6/2002
WO WO-03/039523 A2 5/2003
WO WO-03/051881 A1 6/2003
WO WO-2004/020575 A2 3/2004
WO WO-2004/020576 A2 3/2004
WO WO-2004/064782 A2 8/2004
WO WO-2004/082703 A1 9/2004
WO WO-2005/039551 A2 5/2005
WO WO-2006/015445 A1 2/2006
WO WO-2007024708 A2 3/2007
WO WO-2007/089607 A2 8/2007
WO WO-2007/120863 A2 10/2007
WO WO-2008/039669 A1 4/2008
WO WO-2008/045505 A2 4/2008
WO WO-2008083949 A2 7/2008
WO WO-2008/120016 A1 10/2008
WO WO-2008/156829 A2 12/2008
WO WO-2009/051451 A2 4/2009
WO WO-2009042971 A2 4/2009
WO WO-2009127230 A1 10/2009
WO WO-20090127060 A1 10/2009
WO WO-2009/147519 A1 12/2009
WO WO-2009149253 A2 12/2009
WO WO-2010/014895 A2 2/2010
WO WO-2010/017510 A1 2/2010
WO WO-2010/042877 A1 4/2010
WO WO-2010/054401 A1 5/2010
WO WO-2010/109289 A1 9/2010
WO WO-2010144740 A1 12/2010
WO WO-2011/005850 A1 1/2011
WO WO-2011012316 A2 2/2011
WO WO-2011068810 A1 6/2011
WO WO-2011071931 A2 6/2011
WO WO-2011/127933 A1 10/2011
WO WO-2011130624 A2 10/2011
WO WO-2011133868 A2 10/2011
WO WO-2011/140627 A1 11/2011
WO WO-2012019168 A2 2/2012
WO WO-2012/077080 A1 6/2012
WO WO-2012135805 A2 10/2012
WO WO-2012138530 A1 10/2012
WO WO-2012/158736 A1 11/2012
WO WO-2012/164565 A1 12/2012
WO WO-2013/036748 A1 3/2013
WO WO-2013039857 A1 3/2013
WO WO-2013039861 A2 3/2013
WO WO-2013052523 A1 4/2013
WO WO-2013064911 A2 5/2013
WO WO-2013/090186 A1 6/2013
WO WO-2013/090648 A1 6/2013
WO WO-2013/096709 A2 6/2013
WO WO-2013090294 A1 6/2013
WO WO-2013090897 A1 6/2013
WO WO-2013/101690 A1 7/2013
WO WO-2013103659 A1 7/2013
WO WO-2013113326 A1 8/2013
WO WO-2013113501 A1 8/2013
WO WO-2013113502 A1 8/2013
WO WO-2013130161 A1 9/2013
WO WO-2013/151666 A2 10/2013
WO WO-2013151663 A1 10/2013
WO WO-2013151664 A1 10/2013
WO WO-2013151665 A2 10/2013
WO WO-2013151667 A1 10/2013
WO WO-2013151668 A2 10/2013
WO WO-2013151669 A1 10/2013
WO WO-2013151670 A2 10/2013
WO WO-2013151671 A1 10/2013
WO WO-2013151672 A2 10/2013
WO WO-2013151736 A2 10/2013
WO WO-2013/184976 A2 12/2013
WO WO-2014028429 A2 2/2014
WO WO-2014/081507 A1 5/2014
WO WO-2014/093622 A2 6/2014
WO WO-2014093574 A1 6/2014
WO WO-2014093924 A1 6/2014
WO WO-2014/113089 A2 7/2014
WO WO-2014/152513 A1 9/2014
WO WO-2014/152659 A1 9/2014
WO WO-2014/152673 A1 9/2014
WO WO-2014144039 A1 9/2014
WO WO-2014144711 A1 9/2014
WO WO-2014144767 A1 9/2014
WO WO-2014152027 A1 9/2014
WO WO-2014152030 A1 9/2014
WO WO-2014152031 A1 9/2014
WO WO-2014152211 A1 9/2014
WO WO-2014152540 A1 9/2014
WO WO-2014164253 A1 10/2014
WO WO-2015006747 A2 1/2015
WO WO-2015034925 A1 3/2015
WO WO-2015034928 A1 3/2015
WO WO-2015038892 A1 3/2015
WO WO-2015/051169 A2 4/2015
WO WO-2015048744 A2 4/2015
WO WO-2015051173 A2 4/2015
WO WO-2015051214 A1 4/2015
WO WO-2015058069 A1 4/2015
WO WO-2015/070413 A1 5/2015
WO WO-2015/085318 A2 6/2015
WO WO-2015/089511 A2 6/2015
WO WO-2015/101414 A2 7/2015
WO WO-2015/101416 A1 7/2015
WO WO-2015105926 A1 7/2015
WO WO-2015/196118 A1 12/2015
WO WO-2015/196128 A2 12/2015
WO WO-2015/196130 A2 12/2015
WO WO-2016/010840 A1 1/2016
WO WO-2016/011222 A2 1/2016
WO WO-2016/011226 A1 1/2016
WO WO-2016/034620 A1 3/2016
WO WO-2016/036902 A1 3/2016

(56) References Cited

FOREIGN PATENT DOCUMENTS

WO WO-2016/118724 A1 7/2016
WO WO-2016/118725 A1 7/2016

OTHER PUBLICATIONS

U.S. Appl. No. 61/470,451, Afeyan et al.
"AutoImmune shares collapse on Colloral data in rheumatoid arthritis," Pharma MarketLetter, *Marketletter Publications Ltd.* ISSN:0951-3175 (1999) (2 pages).
"Structure and Properties of Nucleosides and Nucleotides," Department of Chemistry Lecture, University of Maine, <http://chemistry.umeche.maine.edu/CHY431/Basics/Nucleo.html>, retrieved on Dec. 12, 2014, last modified Dec. 18, 2008 (5 pages).
Agris et al., "Thermodynamic contribution of nucleoside modifications to yeast tRNAPhe anticodon stem loop analogs," Acta Biochim Pol., 46(1):163-72 (Feb. 1999).
Akinc et al., Targeted Delivery of RNAi Therapeutics With Endogenous and Exogenous Ligand-Based Mechanisms,Mol Ther. 2009 17:872-879.
Alexopoulou et al., "Recognition of double-stranded RNA and activation of NF-κB by Toll-like receptor 3," Nature 413:732-38 (2001).
Anderson et al., "Incorporation of pseudouridine into mRNA enhances translation by diminishing PKR activation," Nucleic Acids Res. 38(17):5884-92 (2010).
Anderson et al., "Nucleoside modifications in RNA limit activation of 2'-5'-oligoadenylate synthetase and increase resistance to cleavage by RNase L," Nucleic Acids Res. 39(21): 9329-38 (Aug. 2011) (10 pages).
Anderson, Bart R., Dissertation: "Nucleoside Modifications Suppress RNA Activation of Cytoplasmic RNA Sensors," Doctor of Philosophy, Cell & Molecular Biology, University of Pennsylvania, 2010 (197 pages).
Andries et al., "N1-methylpseudouridine-incorporated mRNA outperforms pseudouridine-incorporated mRNA by providing enhanced protein expression and reduced immunogenicity in mammalian cell lines and mice," J Control Release. 217:337-44 (2015).
Applied Biosystems, DNA Synthesizer Model 380B Operations Manual, 2001 (327 pages).
Aviv et al., "Purification of Biologically Active Globin Messenger RNA by Chromatography on Oligothymidylic acid-Cellulose," Proc Nat Acad Sci USA 69(6):1408-1412 (1972).
Bell et al., "In trans T cell tolerance diminishes autoantibody responses and exacerbates experimental allergic encephalomyelitis," J Immunol. 180(3):1508-16 (2008).
Berg et al., Chapter 4: DNA, RNA, and the Flow of Genetic Information. *Biochemistry, Sixth Edition*. W.H. Freeman and Company, 107, 119, 126 (2007) (5 pages).
Berry & Associates, 2009 Product Catalog, downloaded Sep. 3, 2024 (288 pages).
Bio-Rad Laboratories, Inc. "Stocking Up? Reagents and Supplies Quick Reference Guide," <www.discover.bio-rad.com> (24 Pages).
Brand et al., "Biosynthesis of a Hypermodified Nucleotide in *Saccharomyces carlsbergensis* 17S and HeLa-Cell 18S Ribosomal Ribonucleic Acid," Biochem J. 169(1):71-77 (1978) (9 pages).
Bélanger et al., "Characterization of hMTr1, a human Cap1 2'-O-ribose methyltransferase," J Biol Chem. 285(43):33037-44 (2010).
Chang et al., "Synthesis and solution conformation studies of 3-substituted uridine and pseudouridine derivatives," Bioorg Med Chem. 16(5):2676-86 (2008) (11 pages).
Charette et al., "Pseudouridine in RNA: What, Where, How, and Why," IUBMB Life 49(5);341-51 (2000).
Chatterjee et al., "The archaeal COG1901/DUF358 SPOUT-methyltransferase members, together with pseudouridine synthase Pus10, catalyze the formation of 1-methylpseudouridine at position 54 of tRNA," RNA., 18(3):421-33 (Mar. 2012).
Communication pursuant to Rule 164(2)(b) and Article 94(3) EPC for European Application No. 12722942.5, dated Mar. 9, 2018 (11 pages).
Conrad et al., "Enzymatic synthesis of 2'-modified nucleic acids: identification of important phosphate and ribose moieties in RNase P substrates," Nucleic Acids Res 23(11):1845-53 (1995).
Davis et al., "Ribonucleic acids from yeast which contain a fifth nucleotide," J Biol Chem., 227(2):907-15 (Aug. 1957).
De Wet et al., "Firefly Luciferase Gene: Structure and Expression in Mammalian Cells," Mol Cell Bio 7(2):725-37 (1987).
Decision of Rejection for Japanese Patent Application No. 2016-148493, mailed Oct. 16, 2018 (6 pages).
Derrigo et al., "RNA-protein interactions in the control of stability and localization of messenger RNA (review)," Int J Mol Med. 5(2):111-23 (2000).
Diebold et al., "Innate antiviral responses by means of TLR7-mediated recognition of single-stranded RNA," Science. 303(5663): 1529-31 (2004).
El-Sagheer et al., "Click nucleic acid ligation: applications in biology and nanotechnology," Acc Chem Res. 45(8):1258-67 (2012).
Examination Report for Canadian Application No. 2,831,613, dated Sep. 20, 2019 (4 pages).
Fath et al., "Multiparameter RNA and codon optimization: a standardized tool to assess and enhance autologous mammalian gene expression," PLoS One. 6(3):e17596 (2011) (14 pages).
Feng et al., "MDA5 Detects the Double-Stranded RNA Replicative Form in Picornavirus-Infected Cells," Cell Rep 2(5);1187-96 (Nov. 2012).
Gallie et al., "Heat Shock Disrupts Cap and Poly(A) Tail Function during Translation and Increases mRNA Stability of Introduced Reporter mRNA," Plant Physiol 108(4):1703-13 (1995).
Gallie et al., "Post-transcriptional regulation in higher eukaryotes: The role of the reporter gene in controlling expression," Mol Gen Genet 228:258-64 (1991).
Gilham, "The Synthesis of Polynucleotide-Celluloses and Their Use in the Fractionation of Polynucleotides," J Am Chem Soc. 86(22):4982-4985 (1964).
Goodnow, "Pathways for self-tolerance and the treatment of autoimmune diseases," Lancet. 357(9274):2115-21 (2001).
Grosjean, Modification and editing of RNA: historical overview and important facts to remember. *Fine-Tuning of RNA Functions by Modification and Editing*. Grosjean H, 1-22 (2005).
Hames et al., Processing of Eukaryotic Pre-mRNA. *Biochemistry, Third Edition*. Taylor & Francis Group, 220-7 (2005) (10 pages).
Hansen et al., "Circular RNA and miR-7 in Cancer," Cancer Res. 73(18):5609-12 (Sep. 2013).
Hansen et al., "Natural RNA circles function as efficient microRNA sponges," Nature. 495(7441):384-8 (Feb. 2013) (7 pages).
Haseltine et al., "Rous sarcoma virus genome is terminally redundant: the 5' sequence," Proc Natl Acad Sci USA. 74(3):989-93 (1977).
Heil et al., "Species-Specific Recognition of Single-Stranded RNA via Toll-like Receptor 7 and 8." *Science* 303(5663):1526-9 (with supplementary material) (2004) (8 pages).
Helm, M., "Post-transcriptional nucleotide modification and alternative folding of RNA," Nucleic Acids Res 34(2):721-33 (2006).
Henke et al., "microRNA-122 stimulates translation of hepatitis C virus RNA," EMBO J. 27(24):3300-10 (2008).
Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).
Irier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).
Ishii et al., *Nucleic Acids in Innate Immunity*, CRC Press (304 pages) (2008).
Ivanov et al., "RNA Synthesis by T7 RNA Polymerase Supported Primer Extension," J Mol Biol 38(5):674-9 (2004).
Jani et al., "In vitro transcription and capping of Gaussia luciferase mRNA followed by HeLa cell transfection," J Vis Exp. 61:e3702 (2012) (9 pages).

(56) References Cited

OTHER PUBLICATIONS

Jawalekar et al., "Oligonucleotide tagging for copper-free click conjugation," Molecules. 18(7):7346-63 (Jul. 2013).
Karikó et al., "Phosphate-enhanced transfection of cationic lipid-complexed mRNA and plasmid DNA," Biochim Biophys Acta. 1369(2):320-34 (1998).
Karikó et al., "Generating the optimal mRNA for therapy: HPLC purification eliminates immune activation and improves translation of nucleoside-modified, protein-encoding mRNA," Nucleic Acids Res. 39(21): e142, DOI: 10.1093/nar/gkr695 (2011) (10 pages).
Karikó et al., "In vivo protein expression from mRNA delivered into adult rat brain," J Neurosci Methods. 105(1): 77-86 (2001).
Karikó et al., "Incorporation of pseudouridine into mRNA yields superior nonimmunogenic vector with increased translational capacity and biological stability." Mol Ther. 16(11):1833-40 (2008).
Karikó et al., "Increased erythropoiesis in mice injected with submicrogram quantities of pseudouridine-containing mRNA encoding erythropoietin," Mol Ther. 20(5): 948-953 (May 2012).
Karikó et al., "mRNA is an endogenous ligand for Toll-like receptor 3," J Biol Chem. 279(13):12542-50 (2004).
Karikó et al., "Naturally occurring nucleoside modifications suppress the immunostimulatory activity of RNA: Implication for therapeutic RNA development," Curr Opin Drug Discov Devel. 10(5): 523-532 (2007).
Karikó et al., "Suppression of RNA recognition by Toll-like receptors: the impact of nucleoside modification and the evolutionary origin of RNA," Immunity. 23(2):165-75 (2005).
Karikó et al., Supplementary material for "Incorporation of Pseudouridine in mRNA Yields Superior Nonimmunogenic Vector with Increased Translational Capacity and Biological Stability," Mol Ther 16(11):1833-40 (2008) (4 pages).
Kierzek et al., "Influence of N6-isopentenyladenosine ($i^6A$) on thermal stability of RNA duplexes," Biophys Chem., 91(2):135-40 (2001).
Kluiver et al., "Rapid generation of MicroRNA Sponges for MicroRNA Inhibition ," PLoS One. 7(1):E29275 (Jan. 2012)(8 pages).
Kore et al., "Synthesis and application of 2'-fluoro-substituted cap analogs," Bioorg Med Chem Letters. 17:5295-9 (2007).
Kormann et al., "Expression of therapeutic proteins after delivery of chemically modified mRNA in mice," Nat Biotechnol. 29(2):154-7 (including supplement) (2011) (6 pages).
Kozak, M., "Regulation of translation via mRNA structure in prokaryotes and eukaryotes," Gene 361:13-37 (2005).
Kraus et al., "Oral tolerance and inflammatory bowel disease," Curr Opin Gastroenterol. 21(6):692-6 (2005).
Kuribayashi-Ohta et al., "Application of oligo(dT)30-latex for rapid purification of poly(A)+ mRNA and for hybrid subtraction with the in situ reverse transcribed cDNA," Biochim Biophys Acta. 1156(2):204-12 (1993).
Kuwahara et al., "Molecular evolution of functional nucleic acids with chemical modifications," Molecules. 15(8):5423-44 (2010).
Li et al., "Effects of chemically modified messenger RNA on protein expression," Bioconjug Chem. 27(3):849-53 (2016).
Lietard et al., "New strategies for cyclization and bicyclization of oligonucleotides by click chemistry assisted by microwaves," J Org Chem. 73(1):191-200 (2008).
Limbach et al., "Summary: the modifiers nucleosides of RNA," Nucleic Acids Res. 22(12):2183-96 (1994).
Lorenzi et al., "Intranasal vaccination with messenger RNA as a new approach in gene therapy: Use against tuberculosis," BMC Biotechnol. 10(77): 1-11 (2010).
Love et al., "Lipid-like materials for low-dose, in vivo gene silencing," Proc Natl Acad Sci USA. 107(5):1864-9 (2010).
Lukavsky et al., "Large-scale Preparation and Purification of Polyacrylamide-Free RNA Oligonucleotides," RNA. 10(5):889-93 (2004) (6 pages).
Matsumoto et al., "Establishment of a monoclonal antibody against human Toll-like receptor 3 that blocks double-stranded RNA-mediated signaling," Biochem Biophys Res Commun 293(5):1364-9 (2002).
McCloskey et al., "Post-transcriptional modification in archaeal tRNAs: identities and phylogenetic relations of nucleotides from mesophilic and hyperthermophilic *Methanococcales*," Nucleic Acids Res 29(22):4699-706 (2001).
Melton et al., "Efficient in vitro synthesis of biologically active RNA and RNA hybridization probes from plasmids containing a bacteriophage SP6 promoter," Nucleic Acids Res. 12(18):7035-56 (1984).
Memczak et al., "Circular RNAs are a large class of animal RNAs with regulatory potency," Nature. 495(7441):333-8 (Feb. 2013) (10 pages).
Meyer et al., "Combinatorial recombination of gene fragments to construct a library of chimeras," Curr Protoc Protein Sci. Chapter 26:Unit 26.2 (2006) (17 pages).
Mignone et al., "Untranslated regions of mRNAs," Genome Biol. 3(3):Reviews0004 (2002) (10 pages).
Milligan et al., Synthesis of Small RNAs Using T7 RNA Polymerase. *Methods in Enzymology*, vol. 180. Academic Press, Inc., 51-62 (1989).
Miyoshi-Akiyama et al., "Complete genome sequence of *Streptococcus pyogenes* M1 476, isolated from a patient with streptococcal toxic shock syndrome," J Bacteriol. 194(19):5466 (Oct. 2012).
MMessage mMachine Kit Product Manual, Ambion/Invitrogen. Last revised Jan. 4, 2007 (34 pages).
Moretti et al., "Mechanism of translational regulation by miR-2 from sites in the 5' untranslated region or the open reading frame," RNA. 16(12):2493-502 (2010).
Motorin et al, "RNA nucleotide methylation," Wiley Interdiscip Rev RNA., 2(5):611-31 (Sep.-Oct. 2011).
Motorin et al., "5-methylcytosine in RNA: detection, enzymatic formation and biological functions," Nucleic Acids Res., 38(5):1415-30 (Dec. 2009).
Motorin et al., "Appendix 1: Chemical Structures and Classification of Posttranscriptionally Modified Nucleosides in RNA," *Modification and Editing of RNA*. ASM Press, 543-9 (1998).
Motorin, "RNA modification," eLS. John Wiley & Sons, DOI:10.1002/9780470015902.a0000528.pub3 (2015) (18 pages).
Nagata et al., "Molecular cloning and expression of cDNA for human granulocyte colony-stimulating factor," Nature. 319(6052):415-8 (1986).
Nakazato et al., "Purification of messenger RNA and heterogeneous nuclear RNA containing poly(A) sequences," Methods Enzymol. 29:431-43 (1974).
Newby et al., "Investigation of Overhauser effects between pseudouridine and water protons in RNA helices," Proc Natl Acad Sci 99(20):12697-702 (2002) (6 pages).
Nielsen et al., "An mRNA is capped by a 2',5' lariat catalyzed by a group I-like ribozyme," Science. 309(5740):1584-7 (2005).
Notification of Reason for Rejection for Japanese Application No. 2016-148493, mailed May 22, 2018 (6 pages).
Notification of Reasons for Rejection for Japanese Application No. 2019-025010, mailed Mar. 3, 2020 (12 pages).
Notification of Reasons for Rejection for Japanese Patent Application No. 2016-148493, mailed Aug. 4, 2020 (49 pages).
Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).
Oliva et al., "Accurate energies of hydrogen bonded nucleic acid base pairs and triplets in tRNA tertiary interactions," Nucleic Acids Res 34(3):865-79 (2006).
Pang et al., "Structure of a Modified Nucleoside in Archaebacterial tRNA Which Replaces Ribosylthymine. 1-Methylpseudouridine," J Biol Chem., 257(7):3589-92 (Apr. 1982).
Pardi et al., "Expression kinetics of nucleoside-modified mRNA delivered in lipid nanoparticles to mice by various routes," available in PMC Nov. 10, 2016, published in final edited form as: J Control Release. 217:345-51 (2015) (18 pages).
Parham, *The Immune System, Third Edition*.. Garland Science, Taylor & Francis Group, 49-50 (2009) (5 pages).

(56) References Cited

OTHER PUBLICATIONS

Pascolo, Chapter 3: Vaccination With Messenger RNA. *Methods in Molecular Medicine, vol. 127: DNA Vaccines: Methods and Protocols: Second Edition*. Saltzman et al., Humana Press Inc., 23-40 (2006).
Pascolo, S. Vaccination with messenger RNA (mRNA). Handb Exp Pharmacol. 2008; 183:221-235.
Pelletier et al., "The involvement of mRNA secondary structure in protein synthesis," Biochem Cell Biol 65(6):576-81 (1987).
Pozzilli et al., "No effect of oral insulin on residual beta-cell function in recent-onset type I diabetes (the IMDIAB VII)," Diabetologia. 43(8):1000-4 (2000).
PubChem CID 99543, "Compound Summary for 1-Methylpseudouridine," <https://pubchem.ncbi.nlm.nih.gov/compound/1-Methylpseudouridine>, modified Apr. 9, 2022, retrieved on Apr. 14, 2022 (22 pages).
Pyhtila et al., "Signal sequence- and translation-independent mRNA localization to the endoplasmic reticulum," RNA. 14(3):445-53 (2008).
Qiu et al., "Creating a flexible multiple microRNA expression vector by linking precursor microRNAs," Biochem Biophys Res Commun. 411(2):276-80 (Jul. 2011).
R&D Systems, ELISA Catalog & Reference Guide 2007, downloaded Sep. 3, 2024 (60 pages).
Rehm et al., 5b Mutations, Biotechnology, *A Comprehensive Treatise in 8 Volumes, vol. 1: Microbial Fundamentals*. H.J. Rehm and G. Reed, 282 (1981) (3 pages).
Reichman et al., "Nucleosides. CVI. Syntheses of 1-N-methyl-5-(Beta-D-ribofuranosyl)uracil (1-N-methyl-Psi-uridine) and its identity with a metabolite elaborated by *Streptomyces platensis* VAR. *Clarensis*," J Antibiot (Tokyo). 30(2):129-31 (Feb. 1977).
RNA Modification Database Entry for 1-methylpseudouridine <https://mods.rna.albany.edu/mods/modifications/view/55>, retrieved on Feb. 26, 2019 (1 page).
Robbins et al., "2'-O-methyl-modified RNAs Act as TLR7 Antagonists," Mol Ther., 15(9): 1663-9 (Sep. 2007).
Rodriguez et al., "Magnetic poly (styrene/divinylbenzene/acrylic acid)-based hybrid microspheres for bio-molecular recognition," Micro Nano Lett. 6(6):349-352 (2011).
Santner et al., "Efficient access to 3'-terminal azide-modified RNA for inverse click-labeling patterns," Bioconjug Chem. 25(1):188-95 (Jan. 2014).
Second Examination Report for Australian Patent Application No. 2017279733, dated May 2, 2019 (3 pages).
Semple et al., "Rational design of cationic lipids for siRNA delivery," Nat Biotechnol. 28(2):172-6 (2010) (26 pages).
Skyler et al., "Effects of oral insulin in relatives of patients with type 1 diabetes: The Diabetes Prevention Trial—Type 1," Diabetes Care 28(5):1068-76 (2005).
Song et al., "m7GpppG cap dependence for efficient translation of *Drosophila* 70-kDa heat-shock-protein (Hsp70) mRNA," Eur J Biochem 232(3):778-88 (1995).
Sonoke et al., "Tumor regression in mice by delivery of Bcl-2 small interfering RNA with pegylated cationic liposomes," Cancer Res. 68(21):8843-51 (2008) (10 pages).
Sprinzl et al., "Compilation of tRNA sequences and sequences of tRNA genes," Nucleic Acids Res 26(1):148-53 (1998).
Stewart et al., "Effect of azide position on the rate of azido glucose-cyclooctyne cycloaddition," Journal of Carbohydrate Chemistry. 33(7-8):408-19 (2014).
Stocher et al., "Removal of Template DNA From CRNA Preparations by Combined Oligo (dT) Affinity Chromatography and DNase I Digestion," Biotechniques. 36(3):480-2 (2004).
Takita et al., "Precise sequential DNA ligation on a solid substrate: solid-based rapid sequential ligation of multiple DNA molecules," DNA Res. 20(6):583-92 (Dec. 2013).
Tavernier et al., "mRNA as gene therapeutic: how to control protein expression," J Control Release. 150(3):238-47 (Mar. 2011).
Tcherepanova et al., "Ectopic expression of a truncated CD40L protein from synthetic post-transcriptionally capped RNA in dendritic cells induces high levels of IL-12 secretion," BMC Mol Biol., 9:90 (13 pages) (Oct. 2008).
Valadi et al., "Exosome-mediated transfer of mRNAs and microRNAs is a novel mechanism of genetic exchange between cells," Nat Cell Biol. 9(6):654-9 (2007) (17 pages).
Van Tendeloo et al., "mRNA-based gene transfer as a tool for gene and cell therapy," Curr Opin Mol Ther. 9(5):423-31 (2007).
Virnekäs et al., "Trinucleotide phosphoramidites: ideal reagents for the synthesis of mixed oligonucleotides for random mutagenesis," Nucleic Acids Res. 22(25):5600-7 (1994).
Wang et al., "Improving the stability of aptamers by chemical modification," Curr Med Chem. 18(27):4126-38 (2011).
Warren et al., "Highly efficient reprogramming to pluripotency and directed differentiation of human cells with synthetic modified mRNA," Cell Stem Cell. 7(5):618-30 (2010).
Weiner et al., "Oral tolerance," available in PMC May 1, 2012, published in final edited form as: Immunol Rev. 241(1):241-59 (2011) (14 pages).
Weiss et al., "Prophylactic mRNA vaccination against allergy," Curr Opin Allergy Clin Immunol. 10(6):567-74 (2010) (8 pages).
Williams et al., "Messenger Nucleic Acids." *The Encyclopedia of Biochemistry*. Reinhold Publishing Corporation, 513, 692 (1967) (4 pages).
Wilusz et al., "Molecular Biology. A circuitous route to noncoding RNA," Science. 340(6131):440-1 (Apr. 2013).
Wurm et al., "The ribosome assembly factor Nep1 responsible for Bowen-Conradi syndrome is a pseudouridine-N1-specific methyltransferase," Nucleic Acids Res 38(7):2387-98 (2010).
Yamamoto et al., "Current prospects for mRNA gene delivery," Eur J Pharm Biopharm. 71(3):484-9 (2009).
Yarian et al., "Structural and functional roles of the N1- and N3-protons of psi at tRNA's position 39," Nucleic Acids Res., 27(17):3543-9 (Sep. 1999).
Zhou et al., "Synthesis of Functional mRNA in Mammalian Cells by Bacteriophage T3 RNA Polymerase," Mol Cell Biol 10(9):4529-37 (1990).
Züst et al., "Ribose 2'-O-methylation provides a molecular signature for the distinction of self and non-self mRNA dependent on the RNA sensor Mda5," Nat Immunol., 12(2):137-43 (Feb. 2011) (8 pages).

98N12-5 (TETA5-LAP)

DLin DMA

DLin-K-DMA (2,2-Dilinoleyl-4-dimethylaminomethyl-[1,3]-dioxolane)

DLin-KC2-DMA

DLin-MC3-DMA

C12-200

PRIOR ART

SEQUENCE LISTING

```
Sequence total quantity: 17
SEQ ID NO: 1            moltype = DNA  length = 624
FEATURE                 Location/Qualifiers
source                  1..624
                        mol_type = other DNA
                        organism = Homo sapiens
SEQUENCE: 1
atggctggac ctgccaccca gagccccatg aagctgatgg ccctgcagct gctgctgtgg  60
cacagtgcac tctggacagt gcaggaagcc accccccctgg gccctgccag ctccctgccc  120
cagagcttcc tgctcaagtg cttagagcaa gtgaggaaga tccagggcga tggcgcagcg  180
ctccaggaga agctggtgag tgagtgtgcc acctacaagc tgtgccaccc cgaggagctg  240
gtgctgctcg gacactctct gggcatcccc tgggctcccc tgagcagctg ccccagccag  300
gccctgcagc tggcaggctg cttgagccaa ctccatagcg gccttttcct ctaccagggg  360
ctcctgcagg ccctggaagg gatctccccc gagttgggtc ccaccttgga cacactgcag  420
ctggacgtcg ccgactttgc caccaccatc tggcagcaga tggaagaact gggaatggcc  480
cctgccctgc agcccaccca gggtgccatg ccggccttcg cctctgcttt ccagcgccgg  540
gcaggagggg tcctggttgc ctcccatctg cagagcttcc tggaggtgtc gtaccgcgtt  600
ctacgccacc ttgcccagcc ctga                                          624

SEQ ID NO: 2            moltype = DNA  length = 829
FEATURE                 Location/Qualifiers
source                  1..829
                        mol_type = other DNA
                        organism = Homo sapiens
SEQUENCE: 2
ttggaccctc gtacagaagc taatacgact cactataggg aaataagaga gaaaagaaga  60
gtaagaagaa atataagagc caccatggct ggacctgcca cccagagccc catgaagctg  120
atggccctgc agctgctgct gtggcacagt gcactctgga cagtgcagga agccaccccc  180
ctgggccctg ccagctccct gccccagagc ttcctgctca agtgcttaga gcaagtgagg  240
aagatccagg gcgatggcgc agcgctccag gagaagctgg tgagtgagtg tgccacctac  300
aagctgtgcc accccgagga gctggtgctg ctcggacact ctctgggcat cccctgggct  360
cccctgagca gctgccccag ccaggccctg cagctggcag gctgcttgag ccaactccat  420
agcggccttt tcctctacca ggggctcctg caggccctgg aagggatctc ccccgagttg  480
ggtcccacct tggacacact gcagctggac gtcgccgact ttgccaccac catctggcag  540
cagatggaag aactgggaat ggcccctgcc ctgcagccca cccagggtgc catgccggcc  600
ttcgcctctg ctttccagcg ccgggcagga ggggtcctgg ttgcctccca tctgcagagc  660
ttcctggagg tgtcgtaccg cgttctacgc caccttgccc agccctgaag cgctgccttc  720
tgcggggctt gccttctggc catgcccttc ttctctccct tgcacctgta cctcttggtc  780
tttgaataaa gcctgagtag gaaggcggcc gctcgagcat gcatctaga               829

SEQ ID NO: 3            moltype = DNA  length = 772
FEATURE                 Location/Qualifiers
source                  1..772
                        mol_type = other DNA
                        organism = Homo sapiens
SEQUENCE: 3
ttggaccctc gtacagaagc taatacgact cactataggg aaataagaga gaaaagaaga  60
gtaagaagaa atataagagc caccatggcc ctgcagttgc tgctttggca ctcggccctc  120
tggacagtcc aagaagcgac tcctctcgga cctgcctcat cgttgccgca gtcattcctt  180
ttgaagtgtc tggagcaggt gcgaaagatt cagggcgatg gagccgcact ccaagagaag  240
```

```
ctctgcgcga catacaaact ttgccatccc gaggagctcg tactgctcgg gcacagcttg  300
gggattccct gggctcctct ctcgtcctgt ccgtcgcagg ctttgcagtt ggcagggtgc  360
ctttcccagc tccactccgg tttgttcttg tatcagggac tgctgcaagc ccttgaggga  420
atctcgccag aattgggccc gacgctggac acgttgcagc tcgacgtggc ggatttcgca  480
acaaccatct ggcagcagat ggaggaactg ggatggcac  ccgcgctgca gcccacgcag  540
ggggcaatgc cggcctttgc gtccgcgttt cagcgcaggg cgggtggagt cctcgtagcg  600
agccaccttc aatcatttt  ggaagtctcg taccgggtgc tgagacatct tgcgcagccg  660
tgagccttct gcggggcttg ccttctggcc atgcccttct tctctccctt gcacctgtac  720
ctcttggtct ttgaataaag cctgagtagg aaggcggccg ctcgagcatg ca          772

SEQ ID NO: 4           moltype = RNA  length = 746
FEATURE                Location/Qualifiers
source                 1..746
                       mol_type = mRNA
                       organism = Homo sapiens
SEQUENCE: 4
ctcactatag ggaaataaga gagaaaagaa gagtaagaag aaatataaga gccaccaatg  60
gccctgcagt tgctgctttg gcactcggcc ctctggacag tccaagaagc gactcctctc  120
ggacctgcct catcgttgcc gcagtcattc cttttgaagt gtctggagca ggtgcgaaag  180
attcagggcg atggagccgc actccaagag aagctctgcg cgacatacaa actttgccat  240
cccgaggagc tcgtactgct cgggcacagc ttggggattc cctgggctcc tctctcgtcc  300
tgtccgtcgc aggctttgca gttggcaggg tgcctttccc agctccactc cggtttgttc  360
ttgtatcagg gactgctgca agcccttgag ggaatctcgc cagaattggg cccgacgctg  420
gacacgttgc agctcgacgt ggcggatttc gcaacaacca tctggcagca gatggaggaa  480
ctggggatgg cacccgcgct gcagcccacg caggggcaa  tgccggcctt tgcgtccgcg  540
tttcagcgca gggcgggtgg agtcctcgta gcgagccacc ttcaatcatt tttggaagtc  600
tcgtaccggg tgctgagaca tcttgcgcag ccgtgagcct tctgcggggc ttgccttctg  660
gccatgccct tcttctctcc cttgcacctg tacctcttgg tctttgaata aagcctgagt  720
aggaaggcgg ccgctcgagc atgcat                                       746

SEQ ID NO: 5           moltype = RNA  length = 854
FEATURE                Location/Qualifiers
source                 1..854
                       mol_type = mRNA
                       organism = Homo sapiens
SEQUENCE: 5
gggaaataag agagaaaaga agagtaagaa gaaatataag agccaccatg gtatccaagg  60
gggaggagga caacatggcg atcatcaagg agttcatgcg attcaaggtg cacatggaag  120
gttcggtcaa cggacacgaa tttgaaatcg aaggagaggg tgaaggaagg ccctatgaag  180
ggacacagac cgcgaaactc aaggtcacga aggggggacc acttcctttc gcctgggaca  240
ttctttcgcc ccagtttatg tacgggtcca aagcatatgt gaagcatccc gccgatattc  300
ctgactatct gaaactcagc tttcccgagg gattcaagtg ggagcgggtc atgaactttg  360
aggacggggg tgtagtcacc gtaacccaag actcaagcct ccaagacggc gagttcatct  420
acaaggtcaa actgcggggg actaactttc cgtcggatgg gccggtgatg cagaagaaaa  480
cgatgggatg ggaagcgtca tcggagagga tgtacccaga agatggtgca ttgaaggggg  540
agatcaagca gagactgaag ttgaaagatg gggacatta  tgatgccgag gtgaaaacga  600
catacaaagc gaaaaagccg gtgcagcttc ccggagcgta taatgtgaat atcaagttgg  660
atattacttc acacaatgag gactacacaa ttgtcgaaca gtacgaacgc gctgagggta  720
gacactcgac gggaggcatg gacgagttgt acaaatgata agctgccttc tgcggggctt  780
gccttctggc catgcccttc ttctctccct tgcacctgta cctcttggtc tttgaataaa  840
gcctgagtag gaag                                                    854

SEQ ID NO: 6           moltype = DNA  length = 924
FEATURE                Location/Qualifiers
source                 1..924
                       mol_type = other DNA
                       organism = Homo sapiens
SEQUENCE: 6
tcaagctttt ggaccctcgt acagaagcta atacgactca ctatagggaa ataagagaga  60
aaagaagagt aagaagaaat ataagagcca ccatggtatc caaggggggag gaggacaaca  120
tggcgatcat caaggagttc atgcgattca aggtgcacat ggaaggttcg gtcaacggac  180
acgaatttga aatcgaagga gagggtgaag gaaggcccta tgaagggaca cagaccgcga  240
aactcaaggt cacgaaaggg ggaccacttc ctttcgcctg ggacattctt tcgccccagt  300
ttatgtacgg gtccaaagca tatgtgaagc atcccgccga tattcctgac tatctgaaac  360
tcagctttcc cgagggattc aagtgggagc gggtcatgaa ctttgaggac gggggtgtag  420
tcaccgtaac ccaagactca agcctccaag acggcgagtt catctacaag gtcaaactgc  480
gggggactaa ctttccgtcg gatgggccgg tgatgcagaa gaaaacgatg ggatgggaag  540
cgtcatcgga gaggatgtac ccagaagatg gtgcattgaa gggggagatc aagcagagac  600
tgaagttgaa agatggggga cattatgatg ccgaggtgaa aacgacatac aaagcgaaaa  660
agccggtgca gcttcccgga gcgtataatg tgaatatcaa gttggatatt acttcacaca  720
atgaggacta cacaattgtc gaacagtacg aacgcgctga gggtagacac tcgacgggag  780
gcatggacga gttgtacaaa tgataagctg ccttctgcgg ggcttgcctt ctggccatgc  840
ccttcttctc tcccttgcac ctgtacctct tggtctttga ataaagcctg agtaggaagg  900
cggccgctcg agcatgcatc taga                                         924

SEQ ID NO: 7           moltype = RNA  length = 725
FEATURE                Location/Qualifiers
source                 1..725
                       mol_type = mRNA
```

```
                        organism = Homo sapiens
SEQUENCE: 7
gggaaataag agagaaaaga agagtaagaa gaaatataag agccaccatg ggagtgcacg  60
agtgtcccgc gtggttgtgg ttgctgctgt cgctcttgag cctcccactg ggactgcctg  120
tgctgggggc accacccaga ttgatctgcg actcacgggt acttgagagg taccttcttg  180
aagccaaaga agccgaaaac atcacaaccg gatgcgccga gcactgctcc ctcaatgaga  240
acattactgt accggataca aaggtcaatt tctatgcatg gaagagaatg gaagtaggac  300
agcaggccgt cgaagtgtgg caggggctcg cgcttttgtc ggaggcggtg ttgcggggtc  360
aggccctcct cgtcaactca tcacagccgt gggagcccct ccaacttcat gtcgataaag  420
cggtgtcggg gctccgcagc ttgacgacgt tgcttcgggc tctgggcgca caaaaggagg  480
ctatttcgcc gcctgacgcg gcctccgcgg cacccctccg aacgatcacc gcggacacgt  540
ttaggaagct ttttagagtg tacagcaatt tcctccgcgg aaagctgaaa ttgtatactg  600
gtgaagcgtg taggacaggg gatcgctgat aagctgcctt ctgcggggct tgccttctgg  660
ccatgccctt cttctctccc ttgcacctgt acctcttggt ctttgaataa agcctgagta  720
ggaag                                                              725

SEQ ID NO: 8            moltype = RNA  length = 1536
FEATURE                 Location/Qualifiers
source                  1..1536
                        mol_type = mRNA
                        organism = Homo sapiens
SEQUENCE: 8
gggaaataag agagaaaaga agagtaagaa gaaatataag agccaccaat gcagcgcgtc  60
aacatgatta tggccgaatc gccgggactc atcacaatct gcctcttggg ttatctcttg  120
tcggcagaat gtaccgtgtt cttggatcac gaaaacgcga acaaaattct taatcgcccg  180
aagcggtata actccgggaa acttgaggag tttgtgcagg gcaatcttga acgagagtgc  240
atggaggaga aatgctcctt tgaggaggcg agggaagtgt ttgaaaacac agagcgaaca  300
acggagtttt ggaagcaata cgtagatggg gaccagtgtg agtcgaatcc gtgcctcaat  360
gggggatcat gtaaagatga catcaatagc tatgaatgct ggtgcccgtt tgggtttgaa  420
gggaagaact gtgagctgga tgtgacgtgc aacatcaaaa acggacgctg tgagcagttt  480
tgtaagaact cggctgacaa taaggtagta tgctcgtgca cagagggata ccggctggcg  540
gagaaccaaa aatcgtgcga gcccgcagtc ccgttccctt gtgggagggt gagcgtgtca  600
cagactagca agttgacgag agcggagact gtattccccg acgtggacta cgtcaacagc  660
accgaagccg aaacaatcct cgataacatc acgcagagca ctcagtcctt caatgacttt  720
acgagggtcg taggtggtga ggacgcgaaa cccggtcagt tcccctggca ggtggtattg  780
aacggaaaag tcgatgcctt ttgtggaggt tccattgtca acgagaagtg gattgtcaca  840
gcggcacact gcgtagaaac aggagtgaaa atcacggtag tggcgggaga gcataacatt  900
gaagagacag agcacacgga acaaaagcga aatgtcatca gaatcattcc acaccataac  960
tataacgcgg caatcaataa gtacaatcac gacatcgcac ttttggagct tgacgaacct  1020
ttggtgctta attcgtacgt cacccctatt tgtattgccg acaaagagta tacaaacatc  1080
ttcttgaaat tcggctccgg gtacgtatcg ggctggggca gagtgttcca taagggtaga  1140
tccgcactgg tgttgcaata cctcagggtg cccctcgtgg atcgagccac ttgtctgcgg  1200
tccaccaaat tcacaatcta caacaatatg ttctgtgcgg gattccatga aggtgggaga  1260
gatagctgcc agggagactc agggggtccc cacgtgacgg aagtcgaggg gacgtcattt  1320
ctgacgggaa ttatctcatg gggagaggaa tgtgcgatga aggggaaata tggcatctac  1380
actaaagtgt cacggtatgt caattggatc aaggaaaaga cgaaactcac gtgatcagcc  1440
agcgctgcct tctgcggggc ttgccttctg gccatgccct tcttctctcc cttgcacctg  1500
tacctcttgg tctttgaata aagcctgagt aggaag                            1536

SEQ ID NO: 9            moltype = DNA  length = 794
FEATURE                 Location/Qualifiers
source                  1..794
                        mol_type = other DNA
                        organism = Homo sapiens
SEQUENCE: 9
caagcttttg gaccctcgta cagaagctaa tacgactcac tatagggaaa taagagagaa  60
aagaagagta agaagaaata taagagccac catgggagtg cacgagtgtc ccgcgtggtt  120
gtggttgctg ctgtcgctct tgagcctccc actgggactg cctgtgctgg gggcaccacc  180
cagattgatc tgcgactcac gggtacttga gaggtacctt cttgaagcca aagaagccga  240
aaacatcaca accggatgcg ccgagcactg ctccctcaat gagaacatta ctgtaccgga  300
tacaaaggtc aatttctatg catggaagag aatggaagta ggacagcagg ccgtcgaagt  360
gtggcagggg ctcgcgcttt tgtcggaggc ggtgttgcgg ggtcaggccc tcctcgtcaa  420
ctcatcacag ccgtgggagc ccctccaact tcatgtcgat aaagcggtgt cggggctccg  480
cagcttgacg acgttgcttc gggctctggg cgcacaaaag gaggctattt cgccgcctga  540
cgcggcctcc gcggcacccc tccgaacgat caccgcggac acgtttagga agctttttag  600
agtgtacagc aatttcctcc gcggaaagct gaaattgtat actggtgaag cgtgtaggac  660
aggggatcgc tgataagctg ccttctgcgg ggcttgcctt ctggccatgc ccttcttctc  720
tcccttgcac ctgtacctct tggtctttga ataaagcctg agtaggaagg cggccgctcg  780
agcatgcatc taga                                                    794

SEQ ID NO: 10           moltype = DNA  length = 1869
FEATURE                 Location/Qualifiers
source                  1..1869
                        mol_type = other DNA
                        organism = Homo sapiens
SEQUENCE: 10
agcttttgga ccctcgtaca gaagctaata cgactcacta tagggaaata agagagaaaa  60
gaagagtaag aagaaatata agagccacca tggaagatgc gaagaacatc aagaagggac  120
ctgccccgtt ttaccctttg gaggacggta cagcaggaga acagctccac aaggcgatga  180
```

-continued

```
aacgctacgc cctggtcccc ggaacgattg cgtttaccga tgcacatatt gaggtagaca  240
tcacatacgc agaatacttc gaaatgtcgg tgaggctggc ggaagcgatg aagagatatg  300
gtcttaacac taatcaccgc atcgtggtgt gttcggagaa ctcattgcag tttttcatgc  360
cggtccttgg agcacttttc atcggggtcg cagtcgcgcc agcgaacgac atctacaatg  420
agcgggaact cttgaatagc atgggaatct cccagccgac ggtcgtgttt gtctccaaaa  480
aggggctgca gaaaatcctc aacgtgcaga agaagctccc cattattcaa aagatcatca  540
ttatggatag caagacagat taccaagggt tccagtcgat gtataccttt gtgacatcgc  600
atttgccgcc agggtttaac gagtatgact tcgtccccga gtcatttgac agagataaaa  660
ccatcgcgct gattatgaat tcctcgggta gcaccggttt gccaaagggg gtggcgttgc  720
cccaccgcac tgcttgtgtg cggttctcgc acgctaggga tcctatcttt ggtaatcaga  780
tcattcccga cacagcaatc ctgtccgtgg tacctttttca tcacggtttt ggcatgttca  840
cgactctcgg ctatttgatt tgcggtttca gggtcgtact tatgtatcgg ttcgaggaag  900
aactgttttt gagatccttg caagattaca agatccagtc ggccctcctt gtgccaacgc  960
ttttctcatt ctttgcgaaa tcgacactta ttgataagta tgacctttcc aatctgcatg  1020
agattgcctc agggggagcg ccgcttagca aggaagtcgg ggaggcagtg gccaagcgct  1080
tccaccttcc cggaattcgg cagggatacg ggctcacgga gacaacatcc gcgatcctta  1140
tcacgcccga gggtgacgat aagccgggag ccgtcggaaa agtggtcccc ttctttgaag  1200
ccaaggtcgt agacctcgac acgggaaaaa ccctcggagt gaaccagagg ggcgagctct  1260
gcgtgagagg gccgatgatc atgtcaggtt acgtgaataa ccctgaagcg acgaatgcgc  1320
tgatcgacaa ggatgggtgg ttgcattcgg gagacattgc ctattgggat gaggatgagc  1380
acttctttat cgtagatcga cttaagagct tgatcaaata caaaggctat caggtagcgc  1440
ctgccgagct cgagtcaatc ctgctccagc accccaacat tttcgacgcc ggagtggccg  1500
ggttgcccga tgacgacgcg ggtgagctgc cagcggccgt ggtagtcctc gaacatggga  1560
aaacaatgac cgaaaaggag atcgtggact acgtagcatc acaagtgacg actgcgaaga  1620
aactgagggg aggggtagtc tttgtggacg aggtcccgaa aggcttgact gggaagcttg  1680
acgctcgcaa aatccgggaa atcctgatta aggcaaagaa aggcgggaaa atcgctgtct  1740
gataagctgc cttctgcggg gcttgccttc tggccatgcc cttcttctct cccttgcacc  1800
tgtacctctt ggtctttgaa taaagcctga gtaggaaggc ggccgctcga gcatgcatct  1860
agagggccc                                                         1869

SEQ ID NO: 11          moltype = DNA  length = 930
FEATURE                Location/Qualifiers
source                 1..930
                       mol_type = other DNA
                       organism = Homo sapiens
SEQUENCE: 11
tcaagctttt ggaccctcgt acagaagcta atacgactca ctatagggaa ataagagaga  60
aaagaagagt aagaagaaat ataagagcca ccatggtgag caagggcgag gagctgttca  120
ccggggtggt gcccatcctg gtcgagctgg acggcgacgt aaacggccac aagttcagcg  180
tgtccggcga gggcgagggc gatgccacct acggcaagct gaccctgaag ttcatctgca  240
ccaccggcaa gctgcccgtg ccctggccca ccctcgtgac caccctgacc tacggcgtgc  300
agtgcttcag ccgctacccc gaccacatga agcagcacga cttcttcaag tccgccatgc  360
ccgaaggcta cgtccaggag cgcaccatct tcttcaagga cgacggcaac tacaagaccc  420
gcgccgaggt gaagttcgag ggcgacaccc tggtgaaccg catcgagctg aagggcatcg  480
acttcaagga ggacggcaac atcctggggc acaagctgga gtacaactac aacagccaca  540
acgtctatat catggccgac aagcagaaga acggcatcaa ggtgaacttc aagatccgcc  600
acaacatcga ggacggcagc gtgcagctcg ccgaccacta ccagcagaac acccccatcg  660
gcgacggccc cgtgctgctg cccgacaacc actacctgag cacccagtcc gccctgagca  720
aagaccccaa cgagaagcgc gatcacatgg tcctgctgga gttcgtgacc gccgccggga  780
tcactctcgg catggacgag ctgtacaagt aagctgcctt ctgcggggct tgccttctgg  840
ccatgccctt cttctctccc ttgcacctgt acctcttggt ctttgaataa agcctgagta  900
ggaaggcggc cgctcgagca tgcatctaga                                  930

SEQ ID NO: 12          moltype = RNA  length = 716
FEATURE                Location/Qualifiers
source                 1..716
                       mol_type = mRNA
                       organism = Homo sapiens
SEQUENCE: 12
gggaaataag agagaaaaga agagtaagaa gaaatataag agccaccatg aactttctct  60
tgtcatgggt gcactggagc cttgcgctgc tgctgtatct tcatcacgct aagtggagcc  120
aggccgcacc catggcggag ggtggcggac agaatcacca cgaagtagtc aaattcatgg  180
acgtgtacca gaggtcgtat tgccatccga ttgaaactct tgtggatatc tttcaagaat  240
accccgatga aatcgagtac attttcaaac cgtcgtgtgt ccctctcatg aggtgcgggg  300
gatgctgcaa tgatgaaggg ttggagtgtg tccccacgga ggagtcgaat atcacaatgc  360
aaatcatgcg catcaaacca catcagggtc agcatattgg agagatgtcc tttctccagc  420
acaacaaatg tgagtgtaga ccgaagaagg accgagcccg acaggaaaac ccatgcggac  480
cgtgctccga gcggcgcaaa cacttgttcg tacaagaccc ccagacatgc aagtgctcat  540
gtaagaatac cgattcgcgg tgtaaggcga gacagctgga attgaacgag cgcacgtgta  600
ggtgcgacaa gcctagacgg tgagctgcct tctgcggggc ttgccttctg gccatgccct  660
tcttctctcc cttgcacctg tacctcttgg tctttgaata aagcctgagt aggaag      716

SEQ ID NO: 13          moltype = AA  length = 30
FEATURE                Location/Qualifiers
source                 1..30
                       mol_type = protein
                       organism = Homo sapiens
SEQUENCE: 13
MAGPATQSPM KLMALQLLLW HSALWTVQEA                                  30
```

-continued

```
SEQ ID NO: 14          moltype = AA  length = 25
FEATURE                Location/Qualifiers
source                 1..25
                       mol_type = protein
                       organism = Homo sapiens
SEQUENCE: 14
MMPSSVSWGI LLLAGLCCLV PVSLA                                        25

SEQ ID NO: 15          moltype = AA  length = 46
FEATURE                Location/Qualifiers
source                 1..46
                       mol_type = protein
                       organism = Homo sapiens
SEQUENCE: 15
MQRVNMIMAE SPSLITICLL GYLLSAECTV FLDHENANKI LNRPKR                 46

SEQ ID NO: 16          moltype = AA  length = 21
FEATURE                Location/Qualifiers
source                 1..21
                       mol_type = protein
                       organism = Homo sapiens
SEQUENCE: 16
MKGSLLLLLV SNLLLCQSVA P                                            21

SEQ ID NO: 17          moltype = AA  length = 24
FEATURE                Location/Qualifiers
source                 1..24
                       mol_type = protein
                       organism = Homo sapiens
SEQUENCE: 17
MKWVTFISLL FLFSSAYSRG VFRR                                         24
```

DELIVERY AND FORMULATION OF ENGINEERED NUCLEIC ACIDS

CROSS REFERENCE TO RELATED APPLICATIONS

This application is a continuation of U.S. patent application Ser. No. 18/417,715, filed Jan. 19, 2024, which is a continuation of U.S. patent application Ser. No. 17/141,753, filed Jan. 5, 2021, now issued U.S. Pat. No. 11,911,474, which is a continuation of U.S. patent application Ser. No. 15/927,730, filed Mar. 21, 2018, now issued U.S. Pat. No. 10,898,574, which is a continuation of U.S. patent application Ser. No. 15/379,284, filed Dec. 14, 2016, now issued U.S. Pat. No. 9,950,068, which is a division of U.S. patent application Ser. No. 14/337,513, filed Jul. 22, 2014, now issued U.S. Pat. No. 9,533,047, which is a continuation of U.S. patent application Ser. No. 13/897,362, filed May 18, 2013, which is a continuation of U.S. patent application Ser. No. 13/437,034, filed Apr. 2, 2012, now issued U.S. Pat. No. 8,710,200, which claims priority to U.S. Provisional Patent Application No. 61/470,451, filed Mar. 31, 2011, the contents of each is incorporated by reference in its entirety.

REFERENCE TO SEQUENCE LISTING

The present application is being filed along with a Sequence Listing in electronic format. The Sequence Listing file, entitled 50858-1010011_Sequence_Listing_8_15_24.xml, was created on Aug. 15, 2024, and is 26,831 bytes in size. The information in electronic format of the sequence listing is incorporated herein by reference in its entirety.

FIELD OF THE INVENTION

The invention relates to delivery methods. These methods are specifically useful in therapeutic delivery of modified nucleic acids such as modified mRNA (mmRNA).

BACKGROUND OF THE INVENTION

There are multiple problems with prior methodologies of delivering pharmaceutical compositions in order to achieve effective protein expression both for therapeutics and bioprocessing applications. For example, introduced DNA can integrate into host cell genomic DNA at some frequency, resulting in alterations and/or damage to the host cell genomic DNA. Alternatively, the heterologous deoxyribonucleic acid (DNA) introduced into a cell can be inherited by daughter cells (whether or not the heterologous DNA has integrated into the chromosome) or by offspring.

In addition, there are multiple steps which must occur after delivery but before the encoded protein is made which can effect protein expression. Once inside the cell, DNA must be transported into the nucleus where it is transcribed into RNA. The RNA transcribed from DNA must then enter the cytoplasm where it is translated into protein. Not only do the multiple processing steps from administered DNA to protein create lag times before the generation of the functional protein, each step represents an opportunity for error and damage to the cell. Further, it is known to be difficult to obtain DNA expression in cells as frequently DNA enters a cell but is not expressed or not expressed at reasonable rates or concentrations. This can be a particular problem when DNA is introduced into primary cells or modified cell lines.

Assuming the proper management of the foregoing, effective delivery and achievement of therapeutically relevant levels of proteins for a time sufficient to product clinical outcomes remains a significant hurdle.

Consequently, there is a need in the art for the delivery of biological modalities to address pitfalls surrounding the modulation of intracellular translation and processing of nucleic acids encoding polypeptides and therefore optimizing protein expression from the delivered modalities.

The present invention addresses this need by delivering pharmaceutical compositions which can contain modified nucleic acids such as modified mRNA (mmRNA) and may further include formulations to avoid the problems in the art.

SUMMARY OF THE INVENTION

Described herein are compositions and methods for delivery of biological moieties, such as modified nucleic acids, engineered messenger RNA and isolated polynucleotides into cells in order to modulate protein expression.

An isolated polynucleotide may comprise a sequence such as, but not limited to, SEQ ID NO: 4, 7, 8 and 12. The polynucleotide may further comprise a 5'Cap1 structure and a polyA tail of approximately 160 nucleotides in length. Further, the isolated polynucleotide may be formulated in a pharmaceutical composition. A polypeptide of interest may be produced in a cell, tissue or bodily fluid in a subject in need thereof by administering to the subject a pharmaceutical composition comprising a polynucleotide. The polynucleotide may comprise a sequence selected from the group consisting of SEQ ID NO: 4, 7, 8 and 12. The polynucleotide may further comprise a 5'Cap1 structure and a poly-A tail of approximately 160 nucleotides in length.

The pharmaceutical composition may be formulated where the formulation may be selected from, but is not limited to, saline or a lipid formulation. The pharmaceutical composition may be administered by any route of administration such as, but not limited to, intravenous, intramuscular, subcutaneous, and local administration. The lipid formulation may be selected from, but is not limited to, such as, but not limited to, liposomes, lipoplexes, copolymers such as PLGA and lipid nanoparticles The pharmaceutical composition may be administered at a total dose of about 0.1 mg/kg to about 40 mg/kg. The total dose may be administered by multiple administrations. The administration and/or the multiple administration may occur on a schedule such as, but not limited to, three time a day, twice a day, once a day, every other day, every third day, weekly, biweekly, every three weeks, every four weekly, and monthly.

The modified polypeptide may include a polynucleotide modification such as, but not limited to, a nucleoside modification. The nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

An increase in the level of a polypeptide of interest can be observed in tissue such as, but not limited to, the liver, spleen, kidney, lung, heart, peri-renal adipose tissue, thymus and muscle and/or in a bodily fluid such as, but not limited to, peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. The increased level can be observed in the tissue and/or bodily fluid of the subject within 2, 8 and/or 24 hours after administration. Further, the increased level can be determined from the level of a modified polypeptide in an exosome.

The details of various embodiments of the invention are set forth in the description below. Other features, objects, and advantages of the invention will be apparent from the description and the drawings, and from the claims.

BRIEF DESCRIPTION OF THE FIGURES

FIG. 3A shows the screening results in HEK293 cells and FIG. 3B shows the screening results in HepG2 cells.

FIG. 4A shows the screening results in HEK293 cells and FIG. 4B shows the screening results in HepG2 cells.

FIG. 5A shows the screening results of 98N15-2 in HEK293 cells, and FIGS. 5B and 5C shows the screening results of DLin-KC2-DMA in HEK293 cells.

FIG. 6A shows the mean fluorescence intensity of mCherry in HEK293 cells containing 60 ng of modified mCherry mRNA per well.

FIGS. 6B and 6C show the mean fluorescence intensity of mCherry in HEK293 cells which contained nanoparticles formulations having a concentration of 62.5 ng/well of modified mCherry mRNA. FIGS. 6D and 6E show the mean fluorescence intensity of mCherry in HepG2 cells which contained nanoparticle formulations having a concentration of 62.5 ng/well of modified mCherry mRNA.

FIG. 7A shows the concentration in pg/ml of human erythropoietin after intramuscular administration. FIG. 7B shows the concentration in pg/ml of human erythropoietin after subcutaneous administration.

FIG. 8A is a histogram of bioluminescence (photon/sec) from the intramuscular injection of 5 μg in the left hind leg. FIG. 8B is a histogram of bioluminescence from the intramuscular injection of 50 μg in the right hind leg. FIG. 8C is a histogram showing in vivo screening results from biophotoic imaging after a subcutaneous injection of 50 ug. FIG. 8D is a histogram showing in vivo screening results from biophotoic imaging after a administration of 50 ug intravenously.

FIG. 11A shows the concentration in pg/ml of human G-CSF in serum after the administration of modified G-CSF intramuscularly. FIG. 11B shows the concentration in pg/ml of human G-CSF in serum after the administration of modified G-CSF subcutaneously.

Figure 1:
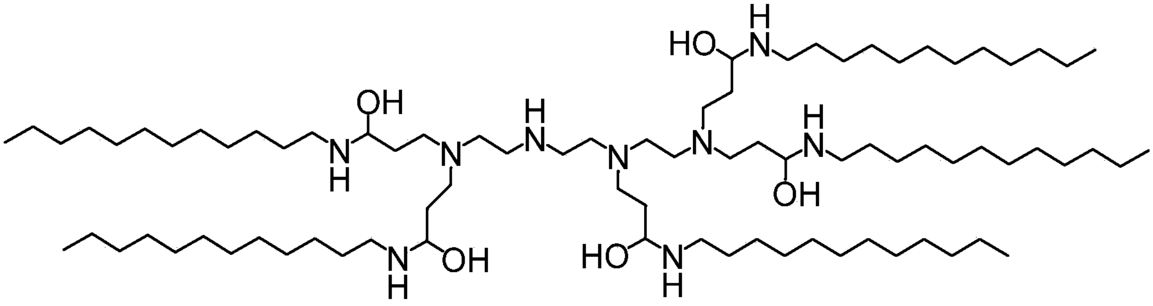
FIG. 1 illustrates lipid structures in the prior art useful in the present invention. Shown are the structures for 98N12-5 (TETA5-LAP), DLin-DMA, DLin-K-DMA (2,2-Dilinoleyl-4-dimethylaminomethyl-[1,3]-dioxolane), DLin-KC2-DMA, DLin-MC3-DMA and C12-200.
Figure 1:
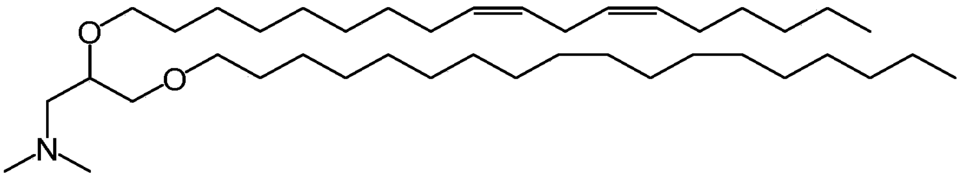
Figure 1:
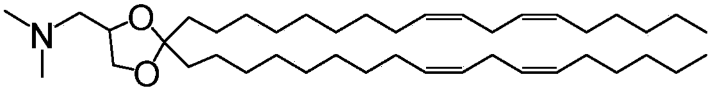
Figure 1:
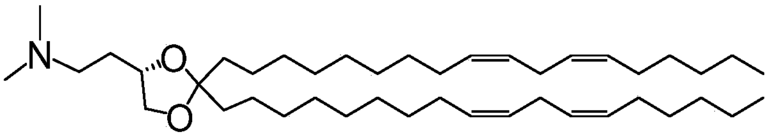
Figure 1:
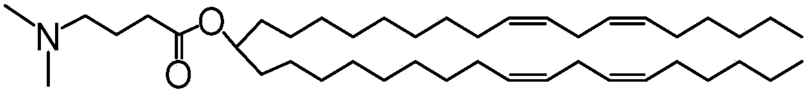
Figure 1:
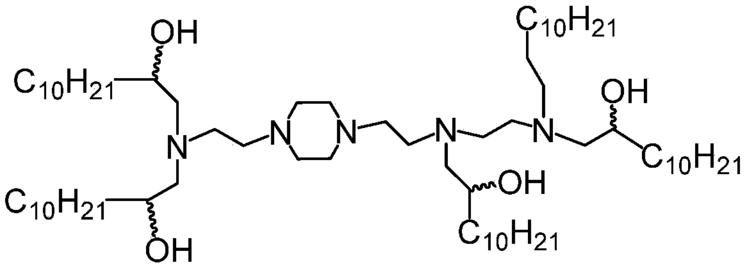

Unless defined otherwise, all technical and scientific terms used herein have the same meaning as those commonly understood to one of ordinary skill in the art to which this invention pertains.

DETAILED DESCRIPTION

Described herein are compositions and methods for the delivery of modified mRNA molecules in order to modulate protein expression.

As described herein and as in copending, co-owned applications International Application PCT/US2011/046861 filed Aug. 5, 2011 and PCT/US2011/054636 filed Oct. 3, 2011, the contents of which are incorporated by reference herein in their entirety, these modified nucleic acid molecules are capable of reducing the innate immune activity of a population of cells into which they are introduced, thus increasing the efficiency of protein production in that cell population.

Modified mRNAs (mmRNAs)

This invention provides nucleic acids, including RNAs, specifically mRNAs, that encode at least one polypeptide and contain one or more modified nucleosides (termed "modified nucleic acids" or "modified nucleic acid molecules" or "engineered nucleic acids"), which have useful properties including the lack of a substantial induction of the innate immune response of a cell into which the mRNA is introduced. Because these mmRNAs enhance the efficiency of protein production, intracellular retention of nucleic acids, and viability of contacted cells, as well as possess reduced immunogenicity, these nucleic acids having these properties are termed "enhanced" nucleic acids or modified RNAs herein.

The term "nucleic acid," in its broadest sense, includes any compound and/or substance that comprise a polymer of nucleotides linked via a phospohdiester bond. These polymers are often referred to as oligonucleotides.

Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or hybrids thereof. They may also include RNAi-inducing agents, RNAi agents, siRNAs, shRNAs, miRNAs, antisense RNAs, ribozymes, catalytic DNA, tRNA, RNAs that induce triple helix formation, aptamers, vectors, etc.

In preferred embodiments, the nucleic acid is one or more modified messenger RNAs (mmRNAs). As described herein, in some embodiments the mmRNAs of the invention do not substantially induce an innate immune response of a cell into which the mRNA is introduced.

The mmRNA of the present invention may encode one or more polypeptides. Generally the polypeptides of interest are those which are naturally occurring in the mammalian genome.

According to the present invention, the shortest length of a modified mRNA, herein "mmRNA," of the present disclosure can be the length of an mRNA sequence that may be sufficient to encode for a dipeptide. In another embodiment, the length of the mRNA sequence may be sufficient to encode for a tripeptide. In another embodiment, the length of an mRNA sequence may be sufficient to encode for a tetrapeptide. In another embodiment, the length of an mRNA sequence may be sufficient to encode for a pentapeptide. In another embodiment, the length of an mRNA sequence may be sufficient to encode for a hexapeptide. In another embodiment, the length of an mRNA sequence may be sufficient to encode for a heptapeptide. In another embodiment, the length of an mRNA sequence may be sufficient to encode for an octapeptide. In another embodiment, the length of an mRNA sequence may be sufficient to encode for a nonapeptide. In another embodiment, the length of an mRNA sequence may be sufficient to encode for a decapeptide.

Generally, the length of a modified mRNA of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the modified mRNA of the present invention includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

Polypeptide Variants

The mmRNA of the present invention may encode variant polypeptides, which have a certain identity with a reference polypeptide sequence, for example a wild type mRNA. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide.

Alternatively, the variant has an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this invention. For example, provided herein is any protein fragment of a reference protein (meaning a polypeptide sequence at least one amino acid residue shorter than a reference polypeptide sequence but otherwise identical) 10, 20, 30, 40, 50, 60, 70, 80, 90, 100 or greater than 100 amino acids in length In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a protein sequence to be utilized in accordance with the invention includes 2, 3, 4, 5, 6, 7, 8, 9, 10, or more mutations as shown in any of the sequences provided or referenced herein.

Targeting Moieties

In embodiments of the invention, mmRNAs are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides.

Cell Penetrating Peptides

The mmRNAs disclosed herein may encode a cell-penetrating polypeptide. As used herein, "cell-penetrating polypeptide" refers to a polypeptide which may facilitate the cellular uptake of molecules. It is known in the art that "CPP" refers to cell-penetration polypeptides and cell-penetrating peptides. When used herein, it will be clarified as to which of either cell-penetrating polypeptides or cell-penetrating peptides the abbreviation CPP refers to.

A cell-penetrating polypeptide of the present invention may contain one or more detectable labels. The polypeptides may be partially labeled or completely labeled throughout. The mmRNA may encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

Fusion Proteins

The modified nucleic acids and mmRNA may encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

Synthesis of Modified mRNAs

Nucleic acids for use in accordance with the invention may be prepared according to any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, DC: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

The modified nucleosides and nucleotides used in the synthesis of modified RNAs disclosed herein can be prepared from readily available starting materials using the following general methods and procedures. It is understood that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The manufacturing process herein can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

Modification of mRNAs

Provided are mmRNAs containing a translatable region and one, two, or more than two different modifications.

In some embodiments, the chemical modifications can be located on the nucleobase of the nucleotide.

In some embodiments, the chemical modifications can be located on the sugar moiety of the nucleotide.

In some embodiments, the chemical modifications can be located on the phosphate backbone of the nucleotide.

Preparation of modified nucleosides and nucleotides used in the manufacture or synthesis of modified RNAs of the present invention can involve the protection and deprotection of various chemical groups. The need for protection and deprotection, and the selection of appropriate protecting groups can be readily determined by one skilled in the art.

The chemistry of protecting groups can be found, for example, in Greene, et al., *Protective Groups in Organic Synthesis,* 2d. Ed., Wiley & Sons, 1991, which is incorporated herein by reference in its entirety.

Modified nucleosides and nucleotides can be prepared according to the synthetic methods described in Ogata et al. *Journal of Organic Chemistry* 74:2585-2588, 2009; Purmal et al. *Nucleic Acids Research* 22(1): 72-78, 1994; Fukuhara et al. *Biochemistry* 1(4): 563-568, 1962; and Xu et al. *Tetrahedron* 48(9): 1729-1740, 1992, each of which are incorporated by reference in their entirety.

Modified mRNAs need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least 50% modified nucleotides, at least 80% modified nucleotides, or at least 90% modified nucleotides.

For example, the mmRNAs may contain a modified pyrimidine such as uracil or cytosine. In some embodiments, at least 5%, at least 10%, at least 25%, at least 50%, at least 80%, at least 90% or 100% of the uracil in the nucleic acid may be replaced with a modified uracil. The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid may be replaced with a modified cytosine. The modified cytosine can be replaced by a compound having a single unique structure, or can be replaced by a plurality of compounds having different structures (e.g., 2, 3, 4 or more unique structures).

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

Further examples of modified nucleotides and modified nucleotide combinations are provided below in Table 1.

TABLE 1

| Modified Nucleotides | Modified Nucleotide Combinations |
|---|---|
| 6-aza-cytidine | α-thio-cytidine/5-iodo-uridine |
| 2-thio-cytidine | α-thio-cytidine/N1-methyl-pseudo-uridine |
| α-thio-cytidine | α-thio-cytidine/α-thio-uridine |
| Pseudo-iso-cytidine | α-thio-cytidine/5-methyl-uridine |
| 5-aminoallyl-uridine | α-thio-cytidine/pseudo-uridine |
| 5-iodo-uridine | Pseudo-iso-cytidine/5-iodo-uridine |
| N1-methyl-pseudouridine | Pseudo-iso-cytidine/N1-methyl-pseudo-uridine |
| 5,6-dihydrouridine | Pseudo-iso-cytidine/α-thio-uridine |
| α-thio-uridine | Pseudo-iso-cytidine/5-methyl-uridine |
| 4-thio-uridine | Pseudo-iso-cytidine/Pseudo-uridine |
| 6-aza-uridine | Pyrrolo-cytidine |
| 5-hydroxy-uridine | Pyrrolo-cytidine/5-iodo-uridine |
| Deoxy-thymidine | Pyrrolo-cytidine/N1-methyl-pseudo-uridine |
| Pseudo-uridine | Pyrrolo-cytidine/α-thio-uridine |
| Inosine | Pyrrolo-cytidine/5-methyl-uridine |
| α-thio-guanosine | Pyrrolo-cytidine/Pseudo-uridine |
| 8-oxo-guanosine | 5-methyl-cytidine/5-iodo-uridine |
| O6-methyl-guanosine | 5-methyl-cytidine/N1-methyl-pseudo-uridine |
| 7-deaza-guanosine | 5-methyl-cytidine/α-thio-uridine |
| No modification | 5-methyl-cytidine/5-methyl-uridine |
| N1-methyl-adenosine | 5-methyl-cytidine/Pseudo-uridine |
| 2-amino-6-Chloro-purine | 5-methyl-cytidine |
| N6-methyl-2-amino-purine | 25% Pseudo-iso-cytidine |
| 6-Chloro-purine | 25% N1-methyl-pseudo-uridine |
| N6-methyl-adenosine | 25% N1-Methyl-pseudo-uridine/75%-pseudo-uridine |
| α-thio-adenosine | 5-methyl-uridine |
| 8-azido-adenosine | 5-iodo-cytidine |
| 7-deaza-adenosine | |

In some embodiments, at least 25% of the cytosines are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines and 25% of the uracils are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

Other components of nucleic acid are optional, and are beneficial in some embodiments. For example, a 5' untranslated region (UTR) and/or a 3'UTR are provided, wherein either or both may independently contain one or more different nucleoside modifications. In such embodiments, nucleoside modifications may also be present in the translatable region. Also provided are nucleic acids containing a Kozak sequence.

Linkers and Payloads

The nucleobase of the nucleotide, which may be incorporated into a mmRNA, can be covalently linked at any chemically appropriate position to a payload, e.g. detectable agent or therapeutic agent. For example, the nucleobase can be deaza-adenosine or deaza-guanosine and the linker can be attached at the C-7 or C-8 positions of the deaza-adenosine or deaza-guanosine. In other embodiments, the nucleobase can be cytosine or uracil and the linker can be attached to the N-3 or C-5 positions of cytosine or uracil.

Linker

The term “linker” as used herein refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., detectable or therapeutic agent, at a second end. The linker may be of sufficient length as to not interfere with incorporation into a nucleic acid sequence.

Examples of chemical groups that can be incorporated into the linker include, but are not limited to, an alkyl, an alkene, an alkyne, an amido, an ether, a thioether or an ester group. The linker chain can also comprise part of a saturated, unsaturated or aromatic ring, including polycyclic and heteroaromatic rings wherein the heteroaromatic ring may be an aryl group containing one to four heteroatoms, N, O or S. Specific examples of linkers include, but are not limited to, unsaturated alkanes, polyethylene glycols, and dextran polymers.

For example, the linker can include, but is not limited to, ethylene or propylene glycol monomeric units, e.g., diethylene glycol, dipropylene glycol, triethylene glycol, tripropylene glycol, tetraethylene glycol, or tetraethylene glycol. In some embodiments, the linker can include, but is not limited to, a divalent alkyl, alkenyl, and/or alkynyl moiety. The linker can include an ester, amide, or ether moiety.

Other examples include, but are not limited to, cleavable moieties within the linker, such as, for example, a disulfide bond (—S—S—) or an azo bond (—N=N—), which can be cleaved using a reducing agent or photolysis. When a cleavable bond which has been incorporated into the linker and attached to a modified nucleotide, is cleaved, a short “scar” or chemical modification on the nucleotide may result. For example, after cleaving, the resulting scar on a nucleotide base, which formed part of the modified nucleotide, and is incorporated into a polynucleotide strand, is unreactive and does not need to be chemically neutralized. This increases the ease with which a subsequent nucleotide can be incorporated during sequencing of a nucleic acid polymer template. For example, conditions include the use of tris(2-carboxyethyl)phosphine (TCEP), dithiothreitol (DTT) and/or other reducing agents for cleavage of a disulfide bond. A selectively severable bond that includes an amido bond can be cleaved for example by the use of TCEP or other reducing agents, and/or photolysis. A selectively severable bond that includes an ester bond can be cleaved for example by acidic or basic hydrolysis.

Detectable Agents

The mmRNAs of the present invention may also be linked or conjugated to one or more detectable agents. Examples of detectable substances include, but are not limited to, various organic small molecules, inorganic compounds, nanoparticles, enzymes or enzyme substrates, fluorescent materials, luminescent materials, bioluminescent materials, chemiluminescent materials, radioactive materials, and contrast agents.

Labels, other than those described herein, are contemplated by the present disclosure, including, but not limited to, other optically-detectable labels. Labels can be attached to the modified nucleotide of the present disclosure at any position using standard chemistries such that the label can be removed from the incorporated base upon cleavage of the cleavable linker.

Terminal Architecture Modifications: 5'-Capping

Endogenous eukaryotic cellular messenger RNA (mRNA) molecules contain a 5'-cap structure on the 5'-end of a mature mRNA molecule. The 5'-cap contains a 5'-5'-triphosphate linkage between the 5'-most nucleotide and guanine nucleotide. The conjugated guanine nucleotide is methylated at the N7 position. Additional modifications include methylation of the ultimate and penultimate most 5'-nucleotides on the 2'-hydroxyl group. The 5'-cap structure is responsible for binding the mRNA Cap Binding Protein (CBP), which is responsibility for mRNA stability in the cell and translation competency.

Multiple distinct 5'-cap structures can be used to generate the 5'-cap of a synthetic mRNA molecule. Many chemical cap analogs are used to co-transcriptionally cap a synthetic mRNA molecule. For example, the Anti-Reverse Cap Analog (ARCA) cap contains a 5'-5'-triphosphate guanine-guanine linkage where one guanine contains an N7 methyl group as well as a 3'-O-methyl group. While chemical cap analogs allow for the concomitant capping of an RNA molecule, up 20% of transcripts remain uncapped and the synthetic cap analog is not identical to an endogenous 5'-cap structure of an authentic cellular mRNA. This may lead to reduced translationally-competency and reduced cellular stability.

Synthetic mRNA molecules may also be capped post-transcriptionally using enzymes responsible for generating a more authentic 5'-cap structure. As used herein the phrase “more authentic” refers to a feature that closely mirrors or mimics, either structurally or functionally an endogenous or wild type feature. More authentic 5'cap structures of the present invention are those which, among other things, have enhanced binding of cap binding proteins, increased half life, reduced susceptibility to 5' endonucleases and/or reduced 5'decapping. For example, recombinant Vaccinia Virus Capping Enzyme and recombinant 2'-O-methyltransferase enzyme can create a canonical 5'-5'-triphosphate linkage between the 5'-most nucleotide of an mRNA and a guanine nucleotide where the guanine contains an N7 methylation and the ultimate 5'-nucleotide contains a 2'-O-methyl generating the Cap1 structure. This results in a cap with higher translational-competency and cellular stability and reduced activation of cellular pro-inflammatory cytokines. Because the synthetic mRNA is caped post-transcriptionally, nearly 100% of the mRNA molecules are capped in contrast to ~80% of synthetic mRNAs containing a chemical cap analog.

Terminal Architecture Modifications: Poly-A Tails

During RNA processing, a long chain of adenine nucleotides (poly-A tail) is normally added to a messenger RNA (mRNA) molecules to increase the stability of the molecule.

Immediately after transcription, the 3' end of the transcript is cleaved to free a 3' hydroxyl. Then poly-A polymerase adds a chain of adenine nucleotides to the RNA. The process, called polyadenylation, adds a poly-A tail that is between 100 and 250 residues long.

It has been discovered that unique poly-A tail lengths provide certain advantages to the modified RNAs of the present invention.

Generally, the length of a poly-A tail of the present invention is greater than 30 nucleotides in length. In another embodiment, the poly-A tail is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides.

In one embodiment, the poly-A tail is designed relative to the length of the overall modified RNA molecule. This design may be based on the length of the coding region of the modified RNA, the length of a particular feature or region of the modified RNA (such as the mRNA), or based on the length of the ultimate product expressed from the modified RNA. In this context the poly-A tail may be 10, 20, 30, 40, 50, 60, 70, 80, 90 or 100% greater in length than the modified RNA or feature thereof. The poly-A tail may also be designed as a fraction of the modified RNA to which it belongs. In this context, the poly-A tail may be 10, 20, 30, 40, 50, 60, 70, 80, or 90% or more of the total length of the construct or the total length of the construct minus the poly-A tail.

Use of Modified mRNAs

The mmRNAs of the present invention may find uses in many areas of research, discovery, therapeutics, diagnostics and in kits and devices.

Therapeutics

The mmRNAs (modified RNAs) and the proteins translated from the mmRNAs described herein can be used as therapeutic agents. For example, an mmRNA described herein can be administered to a subject, wherein the mmRNA is translated in vivo to produce a therapeutic polypeptide in the subject. Provided are compositions, methods, kits, and reagents for treatment or prevention of disease or conditions in humans and other mammals. The active therapeutic agents of the invention include mmRNAs, cells containing mmRNAs or polypeptides translated from the mmRNAs, polypeptides translated from mmRNAs.

Provided herein are methods of inducing translation of a recombinant polypeptide in a cell population using the mmRNAs described herein. Such translation can be in vivo, ex vivo, in culture, or in vitro. The cell population is contacted with an effective amount of a composition containing a mmRNA that has at least one nucleoside modification, and a translatable region encoding the recombinant polypeptide. The population is contacted under conditions such that the mmRNA is localized into one or more cells of the cell population and the recombinant polypeptide is translated in the cell from the nucleic acid.

An effective amount of the composition is provided based, at least in part, on the target tissue, target cell type, means of administration, physical characteristics of the nucleic acid (e.g., size, and extent of modified nucleosides), and other determinants. In general, an effective amount of the composition provides efficient protein production in the cell, preferably more efficient than a composition containing a corresponding unmodified nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a mmRNA), or reduced innate immune response of the host cell.

Aspects of the invention are directed to methods of inducing in vivo translation of a recombinant polypeptide in a mammalian subject in need thereof. Therein, an effective amount of a composition containing a mmRNA that has at least one nucleoside modification and a translatable region encoding the recombinant polypeptide is administered to the subject using the delivery methods and split dosing regimens described herein. The mmRNA is provided in an amount and under other conditions such that the nucleic acid is localized into a cell of the subject and the recombinant polypeptide is translated in the cell from the mmRNA. The cell in which the mmRNA is localized, or the tissue in which the cell is present, may be targeted with one or more than one rounds of mmRNA administration.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered mmRNA directs production of one or more recombinant polypeptides that provide a functional activity which is substantially absent in the cell in which the recombinant polypeptide is translated. For example, the missing functional activity may be enzymatic, structural, or gene regulatory in nature. In related embodiments, the administered mmRNA directs production of one or more recombinant polypeptides that increases (e.g., synergistically) a functional activity which is present but substantially deficient in the cell in which the recombinant polypeptide is translated.

In other embodiments, the administered mmRNA directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In some embodiments, the recombinant polypeptide increases the level of an endogenous protein in the cell to a desirable level; such an increase may bring the level of the endogenous protein from a subnormal level to a normal level or from a normal level to a super-normal level.

Alternatively, the recombinant polypeptide functions to antagonize the activity of an endogenous protein present in, on the surface of, or secreted from the cell. Usually, the activity of the endogenous protein is deleterious to the subject; for example, do to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, a protein toxin such as shiga and tetanus toxins, or a small molecule toxin such as botulinum, cholera, and diphtheria toxins. Additionally, the antagonized biological molecule may be an endogenous protein that exhibits an undesirable activity, such as a cytotoxic or cytostatic activity.

The polypeptides encoded by the mmRNA described herein are engineered for localization within the cell, potentially within a specific compartment such as the nucleus, or are engineered for secretion from the cell or translocation to the plasma membrane of the cell.

In one embodiment of the invention are bifunctional mmRNA. As the name implies, bifunctional mmRNA are those having or capable of at least two functions.

The multiple functionalities of bifunctional mmRNAs may be encoded by the mRNA (the function may not manifest until the encoded product is translated) or may be a property of the RNA itself. It may be structural or chemical. Bifunctional modified RNAs may comprise a function that is covalently associated with the RNA or electrostatically associated.

In some embodiments, modified mRNAs and their encoded polypeptides in accordance with the present invention may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Avoidance of the Innate Immune Response

The term "innate immune response" includes a cellular response to exogenous single stranded nucleic acids, generally of viral or bacterial origin, which involves the induction of cytokine expression and release, particularly the interferons, and cell death. Protein synthesis is also reduced during the innate cellular immune response. While it is advantageous to eliminate the innate immune response in a cell, the invention provides modified mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unmodified nucleic acid. Such a reduction can be measured by expression or activity level of Type 1 interferons or the expression of interferon-regulated genes such as the toll-like receptors (e.g., TLR7 and TLR8). Reduction of innate immune response can also be measured by decreased cell death following one or more administrations of modified RNAs to a cell population; e.g., cell death is 10%, 25%, 50%, 75%, 85%, 90%, 95%, or over 95% less than the cell death frequency observed with a corresponding unmodified nucleic acid. Moreover, cell death may affect fewer than 50%, 40%, 30%, 20%, 10%, 5%, 1%, 0.1%, 0.01% or fewer than 0.01% of cells contacted with the mmRNAs.

The invention provides therapeutic methods for the repeated introduction (e.g., transfection) of mmRNAs into a target cell population, e.g., in vitro, ex vivo, or in vivo. The step of contacting the cell population may be repeated one or more times (such as two, three, four, five or more than five times). In some embodiments, the step of contacting the cell population with the mmRNAs is repeated a number of times sufficient such that a predetermined efficiency of protein translation in the cell population is achieved. Given the reduced cytotoxicity of the target cell population provided by the nucleic acid modifications, such repeated transfections are achievable in a diverse array of cell types.

Protein Production

The methods provided herein are useful for enhancing protein product yield in a cell culture process. In a cell culture containing a plurality of host cells, introduction of the modified mRNAs described herein results in increased protein production efficiency relative to a corresponding unmodified nucleic acid. Such increased protein production efficiency can be demonstrated, e.g., by showing increased cell transfection, increased protein translation from the nucleic acid, decreased nucleic acid degradation, and/or reduced innate immune response of the host cell. Protein production can be measured by ELISA, and protein activity can be measured by various functional assays known in the art. The protein production may be generated in a continuous or a fed-batch mammalian process.

Additionally, it is useful to optimize the expression of a specific polypeptide in a cell line or collection of cell lines of potential interest, particularly an engineered protein such as a protein variant of a reference protein having a known activity. In one embodiment, provided is a method of optimizing expression of an engineered protein in a target cell, by providing a plurality of target cell types, and independently contacting with each of the plurality of target cell types a modified mRNA encoding an engineered polypeptide. Additionally, culture conditions may be altered to increase protein production efficiency. Subsequently, the presence and/or level of the engineered polypeptide in the plurality of target cell types is detected and/or quantitated, allowing for the optimization of an engineered polypeptide's expression by selection of an efficient target cell and cell culture conditions relating thereto. Such methods are particularly useful when the engineered polypeptide contains one or more post-translational modifications or has substantial tertiary structure, situations which often complicate efficient protein production.

Gene Silencing

The modified mRNAs described herein are useful to silence (i.e., prevent or substantially reduce) expression of one or more target genes in a cell population. A modified mRNA encoding a polypeptide capable of directing sequence-specific histone H3 methylation is introduced into the cells in the population under conditions such that the polypeptide is translated and reduces gene transcription of a target gene via histone H3 methylation and subsequent heterochromatin formation. In some embodiments, the silencing mechanism is performed on a cell population present in a mammalian subject. By way of non-limiting example, a useful target gene is a mutated Janus Kinase-2 family member, wherein the mammalian subject expresses the mutant target gene suffers from a myeloproliferative disease resulting from aberrant kinase activity.

Co-administration of modified mRNAs and siRNAs are also provided herein. As demonstrated in yeast, sequence-specific trans silencing is an effective mechanism for altering cell function. Fission yeast require two RNAi complexes for siRNA-mediated heterochromatin assembly: the RNA-induced transcriptional silencing (RITS) complex and the RNA-directed RNA polymerase complex (RDRC) (Motamedi et al. Cell 2004, 119, 789-802). In fission yeast, the RITS complex contains the siRNA binding Argonaute family protein Ago1, a chromodomain protein Chp1, and Tas3. The fission yeast RDRC complex is composed of an RNA-dependent RNA Polymerase Rdp1, a putative RNA helicase Hrr1, and a polyA polymerase family protein Cid12. These two complexes require the Dicer ribonuclease and Clr4 histone H3 methyltransferase for activity. Together, Ago1 binds siRNA molecules generated through Dicer-mediated cleavage of Rdp1 co-transcriptionally generated dsRNA transcripts and allows for the sequence-specific direct association of Chp1, Tas3, Hrr1, and Clr4 to regions of DNA destined for methylation and histone modification and subsequent compaction into transcriptionally silenced heterochromatin. While this mechanism functions in cis- with centromeric regions of DNA, sequence-specific trans silencing is possible through co-transfection with double-stranded siRNAs for specific regions of DNA and concomitant RNAi-directed silencing of the siRNA ribonuclease Eri1 (Buhler et al. Cell 2006, 125, 873-886).

Modulation of Biological Pathways

The rapid translation of modified mRNAs introduced into cells provides a desirable mechanism of modulating target biological pathways. Such modulation includes antagonism or agonism of a given pathway. In one embodiment, a method is provided for antagonizing a biological pathway in a cell by contacting the cell with an effective amount of a composition comprising a modified nucleic acid encoding a recombinant polypeptide, under conditions such that the nucleic acid is localized into the cell and the recombinant polypeptide is capable of being translated in the cell from the nucleic acid, wherein the recombinant polypeptide inhibits the activity of a polypeptide functional in the biological pathway. Exemplary biological pathways are those defective in an autoimmune or inflammatory disorder such as multiple sclerosis, rheumatoid arthritis, psoriasis, lupus erythematosus, ankylosing spondylitis colitis, or Crohn's disease; in particular, antagonism of the IL-12 and IL-23 signaling pathways are of particular utility. (See Kikly K, Liu L, Na S, Sedgwick J D (2006) Curr. Opin. Immunol. 18 (6): 670-5).

Further, provided are modified nucleic acids encoding an antagonist for chemokine receptors; chemokine receptors CXCR-4 and CCR-5 are required for, e.g., HIV entry into host cells (et al, (1996) October 3; 383(6599):400).

Alternatively, provided are methods of agonizing a biological pathway in a cell by contacting the cell with an effective amount of a modified nucleic acid encoding a recombinant polypeptide under conditions such that the nucleic acid is localized into the cell and the recombinant polypeptide is capable of being translated in the cell from the nucleic acid, and the recombinant polypeptide induces the activity of a polypeptide functional in the biological pathway. Exemplary agonized biological pathways include pathways that modulate cell fate determination. Such agonization is reversible or, alternatively, irreversible.

Cellular Nucleic Acid Delivery

Methods of the present invention enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside modification and, optionally, a translatable region. The composition also generally contains a transfection reagent or other compound that increases the efficiency of enhanced nucleic acid uptake into the host cells. The enhanced nucleic acid exhibits enhanced retention in the cell population, relative to a corresponding unmodified nucleic acid. The retention of the enhanced nucleic acid is greater than the retention of the unmodified nucleic acid. In some embodiments, it is at least about 50%, 75%, 90%, 95%, 100%, 150%, 200% or more than 200% greater than the retention of the unmodified nucleic acid. Such retention advantage may be achieved by one round of transfection with the enhanced nucleic acid, or may be obtained following repeated rounds of transfection. In some embodiments, the enhanced nucleic acid is delivered to a target cell population with one or more additional nucleic acids. Such delivery may be at the same time, or the enhanced nucleic acid is delivered prior to delivery of the one or more additional nucleic acids. The additional one or more nucleic acids may be modified nucleic acids or unmodified nucleic acids. It is understood that the initial presence of the enhanced nucleic acids does not substantially induce an innate immune response of the cell population and, moreover, that the innate immune response will not be activated by the later presence of the unmodified nucleic acids. In this regard, the enhanced nucleic acid may not itself contain a translatable region, if the protein desired to be present in the target cell population is translated from the unmodified nucleic acids.

Expression of Ligand or Receptor on Cell Surface

In some aspects and embodiments of the aspects described herein, the modified RNAs can be used to express a ligand or ligand receptor on the surface of a cell (e.g., a homing moiety). A ligand or ligand receptor moiety attached to a cell surface can permit the cell to have a desired biological interaction with a tissue or an agent in vivo. A ligand can be an antibody, an antibody fragment, an aptamer, a peptide, a vitamin, a carbohydrate, a protein or polypeptide, a receptor, e.g., cell-surface receptor, an adhesion molecule, a glycoprotein, a sugar residue, a therapeutic agent, a drug, a glycosaminoglycan, or any combination thereof. For example, a ligand can be an antibody that recognizes a cancer-cell specific antigen, rendering the cell capable of preferentially interacting with tumor cells to permit tumor-specific localization of a modified cell. A ligand can confer the ability of a cell composition to accumulate in a tissue to be treated, since a preferred ligand may be capable of interacting with a target molecule on the external face of a tissue to be treated. Ligands having limited cross-reactivity to other tissues are generally preferred.

In some cases, a ligand can act as a homing moiety which permits the cell to target to a specific tissue or interact with a specific ligand. Such homing moieties can include, but are not limited to, any member of a specific binding pair, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((SCFV)2 fragments), diabodies, tribodies or tetrabodies, which typically are covalently linked or otherwise stabilized (i.e., leucine zipper or helix stabilized) scFv fragments; and other homing moieties include for example, aptamers, receptors, and fusion proteins.

In some embodiments, the homing moiety may be a surface-bound antibody, which can permit tuning of cell targeting specificity. This is especially useful since highly specific antibodies can be raised against an epitope of interest for the desired targeting site. In one embodiment, multiple antibodies are expressed on the surface of a cell, and each antibody can have a different specificity for a desired target. Such approaches can increase the avidity and specificity of homing interactions.

A skilled artisan can select any homing moiety based on the desired localization or function of the cell, for example an estrogen receptor ligand, such as tamoxifen, can target cells to estrogen-dependent breast cancer cells that have an increased number of estrogen receptors on the cell surface. Other non-limiting examples of ligand/receptor interactions include CCRI (e.g., for treatment of inflamed joint tissues or brain in rheumatoid arthritis, and/or multiple sclerosis), CCR7, CCR8 (e.g., targeting to lymph node tissue), CCR6, CCR9, CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), VLA-4/VCAM-1 (e.g., targeting to endothelium). In general, any receptor involved in targeting (e.g., cancer metastasis) can be harnessed for use in the methods and compositions described herein.

Mediators of Cell Death

In one embodiment, a modified nucleic acid molecule composition can be used to induce apoptosis in a cell (e.g., a cancer cell) by increasing the expression of a death receptor, a death receptor ligand or a combination thereof. This method can be used to induce cell death in any desired cell and has particular usefulness in the treatment of cancer where cells escape natural apoptotic signals.

Apoptosis can be induced by multiple independent signaling pathways that converge upon a final effector mechanism consisting of multiple interactions between several “death receptors” and their ligands, which belong to the tumor necrosis factor (TNF) receptor/ligand superfamily. The best-characterized death receptors are CD95 (“Fas”), TNFRI (p55), death receptor 3 (DR3 or Apo3/TRAMO), DR4 and DR5 (apo2-TRAIL-R2). The final effector mechanism of apoptosis may be the activation of a series of proteinases designated as caspases. The activation of these caspases results in the cleavage of a series of vital cellular proteins and cell death. The molecular mechanism of death receptors/ligands-induced apoptosis is well known in the art. For example, Fas/FasL-mediated apoptosis is induced by binding of three FasL molecules which induces trimerization of Fas receptor via C-terminus death domains (DDs), which in turn recruits an adapter protein FADD (Fas-associated protein with death domain) and Caspase-8. The oligomerization of this trimolecular complex, Fas/FAIDD/caspase-8, results in proteolytic cleavage of proenzyme caspase-8 into active caspase-8 that, in turn, initiates the apoptosis process by activating other downstream caspases through proteolysis, including caspase-3. Death ligands in general are apoptotic when formed into trimers or higher order of structures. As monomers, they may serve as antiapoptotic agents by competing with the trimers for binding to the death receptors.

In one embodiment, the modified nucleic acid molecule composition encodes for a death receptor (e.g., Fas, TRAIL, TRAMO, TNFR, TLR etc). Cells made to express a death receptor by transfection of modified RNA become susceptible to death induced by the ligand that activates that receptor. Similarly, cells made to express a death ligand, e.g., on their surface, will induce death of cells with the receptor when the transfected cell contacts the target cell. In another embodiment, the modified RNA composition encodes for a death receptor ligand (e.g., FasL, TNF, etc). In another embodiment, the modified RNA composition encodes a caspase (e.g., caspase 3, caspase 8, caspase 9 etc). Where cancer cells often exhibit a failure to properly differentiate to a non-proliferative or controlled proliferative form, in another embodiment, the synthetic, modified RNA composition encodes for both a death receptor and its appropriate activating ligand. In another embodiment, the synthetic, modified RNA composition encodes for a differentiation factor that when expressed in the cancer cell, such as a cancer stem cell, will induce the cell to differentiate to a non-pathogenic or nonself-renewing phenotype (e.g., reduced cell growth rate, reduced cell division etc) or to induce the cell to enter a dormant cell phase (e.g., Go resting phase).

One of skill in the art will appreciate that the use of apoptosis-inducing techniques may require that the modified nucleic acid molecules are appropriately targeted to e.g., tumor cells to prevent unwanted wide-spread cell death. Thus, one can use a delivery mechanism (e.g., attached ligand or antibody, targeted liposome etc) that recognizes a cancer antigen such that the modified nucleic acid molecules are expressed only in cancer cells.

Formulations of Modified mRNAs

Provided herein are formulations containing an effective amount of an mmRNA.

In certain embodiments, the formulations include one or more cell penetration agents, e.g., transfection agents. In one specific embodiment, an mmRNA is mixed or admixed with a transfection agent (or mixture thereof) and the resulting mixture is employed to transfect cells. Preferred transfection agents are cationic lipid compositions, particularly monovalent and polyvalent cationic lipid compositions, more particularly LIPOFECTIN®, LIPOFECTACE®, LIPOFECTAMINE™, CELLFECTIN®, DMRIE-C, DMRIE, DOTAP, DOSPA, and DOSPER, and dendrimer compositions, particularly G5-G10 dendrimers, including dense star dendrimers, PAMAM dendrimers, grafted dendrimers, and dendrimers known as dendrigrafts and SUPERFECT®.

In a second specific transfection method, a ribonucleic acid is conjugated to a nucleic acid-binding group, for example a polyamine and more particularly a spermine, which is then introduced into the cell or admixed with a transfection agent (or mixture thereof) and the resulting mixture is employed to transfect cells. In a third specific embodiment, a mixture of one or more transfection-enhancing peptides, proteins, or protein fragments, including fusagenic peptides or proteins, transport or trafficking peptides or proteins, receptor-ligand peptides or proteins, or nuclear localization peptides or proteins and/or their modified analogs (e.g., spermine modified peptides or proteins) or combinations thereof are mixed with and complexed with a ribonucleic acid to be introduced into a cell, optionally being admixed with transfection agent and the resulting mixture is employed to transfect cells. Further, a component of a transfection agent (e.g., lipids, cationic lipids or dendrimers) is covalently conjugated to selected peptides, proteins, or protein fragments directly or via a linking or spacer group. Of particular interest in this embodiment are peptides or proteins that are fusagenic, membrane-permeabilizing, transport or trafficking, or which function for cell-targeting. The peptide- or protein-transfection agent complex is combined with a ribonucleic acid and employed for transfection.

In certain embodiments, the formulations include a pharmaceutically acceptable carrier that causes the effective amount of mmRNA to be substantially retained in a target tissue containing the cell.

In certain embodiments, the formulation may include at least an mmRNA and a delivery agent. In some embodiments, the delivery agent may comprise lipidoid-based formulations allowed for localized and systemic delivery of mmRNA.

Also provided are compositions for generation of an in vivo depot containing an engineered ribonucleotide. For example, the composition contains a bioerodible, biocompatible polymer, a solvent present in an amount effective to plasticize the polymer and form a gel therewith, and an engineered ribonucleic acid. In certain embodiments the composition also includes a cell penetration agent as described herein. In other embodiments, the composition also contains a thixotropic amount of a thixotropic agent mixable with the polymer so as to be effective to form a thixotropic composition. Further compositions include a stabilizing agent, a bulking agent, a chelating agent, or a buffering agent.

In other embodiments, provided are sustained-release delivery depots, such as for administration of a mmRNA to an environment (meaning an organ or tissue site) in a patient. Such depots generally contain a mmRNA and a flexible chain polymer where both the mmRNA and the flexible chain polymer are entrapped within a porous matrix of a crosslinked matrix protein. Usually, the pore size is less than 1 mm, such as 900 nm, 800 nm, 700 nm, 600 nm, 500 nm, 400 nm, 300 nm, 200 nm, 100 nm, or less than 100 nm. Usually the flexible chain polymer is hydrophilic. Usually the flexible chain polymer has a molecular weight of at least 50 kDa, such as 75 kDa, 100 kDa, 150 kDa, 200 kDa, 250 kDa, 300 kDa, 400 kDa, 500 kDa, or greater than 500 kDa. Usually the flexible chain polymer has a persistence length of less than 10%, such as 9, 8, 7, 6, 5, 4, 3, 2, 1 or less than 1% of the persistence length of the matrix protein. Usually the flexible chain polymer has a charge similar to that of the matrix protein. In some embodiments, the flexible chain polymer alters the effective pore size of a matrix of cross-linked matrix protein to a size capable of sustaining the diffusion of the mmRNA from the matrix into a surrounding tissue comprising a cell into which the mmRNA is capable of entering.

Formulation Using Lipidoids

The pharmaceutical compositions described herein include lipidoid-based formulations allowing for localized and systemic delivery of mmRNA. The synthesis of lipidoids has been extensively described and formulations containing these compounds are particularly suited for delivery of polynucleotides (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein by reference in their entireties).

According to the present invention, complexes, micelles, liposomes or particles can be prepared containing these lipidoids and therefore, result in an effective delivery of mmRNA, as judged by the production of an encoded protein, following the injection of an mmRNA-formulated lipidoids via localized and systemic routes of administration. Modified mRNA-lipidoid complexes can be administered by various means disclosed herein.

The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879 herein incorporated by reference), use of lipidoid oligonucleotides to deliver the formulation to other cells types including, but not limited to, endothelial cells, myeloid cells, and muscle cells may not be similarly size-limited.

In one aspect, effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of the mmRNA molecule for delivery to different cell types including, but not limited to, hepatocytes, myeloid cells, muscle cells, etc. For example, the component molar ratio may include, but is not limited to, 50% lipid, 10% disteroylphosphatidyl choline, 38.5% cholesterol, and %1.5 PEG. The lipid may be selected from, but is not limited to, DLin-DMA, DLin-K-DMA, DLin-KC2-DMA, 98N12-5, C12-200 (including variants and derivatives), DLin-MC3-DMA and analogs thereof. The use of lipidoid formulations for the localized delivery of nucleic acids to cells (such as, but not limited to, adipose cells and muscle cells) via either subcutaneous or intramuscular delivery, may also not require all of the formulation components which may be required for systemic delivery, and as such may comprise the lipidoid and the mmRNA.

In a further embodiment, combinations of different lipidoids may be used to improve the efficacy of mmRNA-directed protein.

According to the present invention, modified mRNA may be formulated by mixing the mmRNA with the lipidoid at a set ratio prior to addition to cells. In vivo formulations may require the addition of extra ingredients to facilitate circulation throughout the body. To test the ability of these lipidoids to form particles suitable for in vivo work, a standard formulation process used for siRNA-lipidoid formulations may be used as a starting point. Initial mmRNA-lipidoid formulations consist of particles composed of 42% lipidoid, 48% cholesterol and 10% PEG, with further optimization of ratios possible. After formation of the particle, mmRNA is added and allowed to integrate with the complex. The encapsulation efficiency is determined using a standard dye exclusion assays.

In vivo delivery of nucleic acids may be affected by many parameters, including, but not limited to, the formulation composition, nature of particle PEGylation, degree of loading, oligonucleotide to lipid ratio, and biophysical parameters such as particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010)), C12-200 (including derivatives and variants), MD1, DLin-DMA, DLin-K-DMA, DLin-KC2-DMA and DLin-MC3-DMA (see FIG. 1), can be tested for in vivo activity.

The lipidoid referred to herein as "98N12-5" is disclosed by Akinc et al., Mol Ther. 2009 17:872-879 and is incorporated by reference in its entirety. (See FIG. 1)

The lipidoid referred to herein as "C12-200" is disclosed by Love et al., Proc Natl Acad Sci USA. 2010 107:1864-1869 (see FIG. 1) and Liu and Huang, Molecular Therapy. 2010 669-670 (see FIG. 1); both of which are herein incorporated by reference in their entirety. The lipidoid formulations can include particles comprising either 3 or 4 or more components in addition to polynucleotide, primary construct, or mmRNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

The ratio of mmRNA to lipidoid used to test for in vitro transfection is tested empirically at different lipidoid:mmRNA ratios. Previous work using siRNA and lipidoids have utilized 2.5:1, 5:1, 10:1, and 15:1 lipidoid:siRNA wt:wt ratios. Given the longer length of mmRNA relative to siRNA, a lower wt:wt ratio of lipidoid to mmRNA is likely to be effective. In addition, for comparison mmRNA are also formulated using RNAiMax (Invitrogen, Carlsbad, CA) or TRANSIT-mRNA (Mirus Bio, Madison WI) cationic lipid delivery vehicles.

The ability of lipidoid-formulated mmRNA to express the desired protein product can be confirmed by luminescence for luciferase expression, flow cytometry for expression, and by ELISA for secretion.

The expression of mmRNA-encoded proteins can be assessed both within the muscle or subcutaneous tissue and systemically in blood and other organs and fluids such as the liver and spleen, urine, saliva, etc.

For example, single dose studies allow an assessment of the magnitude, dose responsiveness, and longevity of expression of the desired product. After formulation of mmRNA with the lipidoid formulations, as described previously, animals are divided into groups receiving either a saline formulation, or a lipidoid-formulation containing one of several different mmRNA. Prior to injection, mmRNA-containing lipidoid formulations are diluted in PBS and animals administered a single intramuscular dose of formulated mmRNA ranging from 50 mg/kg to doses as low as 1 ng/kg with a preferred range to be 10 mg/kg to 100 ng/kg. If the animal tested is a mouse the maximum dose can be roughly 1 mg mmRNA or as low as 0.02 ng mmRNA if administered once into the hind limb. Likewise for subcutaneous administration, mmRNA-containing lipidoid formulations are diluted in PBS before the animals are administered a single subcutaneous dose of formulated mmRNA ranging from 400 mg/kg- to doses as low as 1 ng/kg. A preferred dosage range comprises 80 mg/kg to 100 ng/kg. If the animal tested is a mouse, the maximum dose administered can be roughly 8 mg mmRNA or as low as 0.02 ng mmRNA if the dose is administered once subcutaneously.

It is preferred that the volume of a single intramuscular injection is maximally 0.025 ml and of a single subcutaneous injection is maximally 0.2 ml for a 20 gram mouse. The dose of the mmRNA administered to the animal is calculated depending on the body weight of the animal. At various points in time points following the administration of the mmRNA-lipidoid, serum, tissues, and tissue lysates can be obtained and the level of the mmRNA-encoded product determined. The ability of lipidoid-formulated mmRNA to express the desired protein product can be confirmed by luminescence for luciferase expression, flow cytometry, and by ELISA.

Additional studies for a multi-dose regimen can also be performed to determine the maximal expression using mmRNA, to evaluate the saturability of the mmRNA-driven expression (achieved by giving a control and active mmRNA formulation in parallel or in sequence), and to determine the feasibility of repeat drug administration (by giving mmRNA in doses separated by weeks or months and then determining whether expression level is affected by factors such as immunogenicity).

Administration

The present invention provides methods comprising administering modified mRNAs and or complexes in accordance with the invention to a subject in need thereof. mmRNA or complexes, or pharmaceutical, imaging, diagnostic, or prophylactic compositions thereof, may be administered to a subject using any amount and any route of administration which may be effective for preventing, treating, diagnosing, or imaging a disease, disorder, and/or condition (e.g., a disease, disorder, and/or condition relating to working memory deficits). The exact amount required will vary from subject to subject, depending on factors such as, but not limited to, the species, age, and general condition of the subject, the severity of the disease, the particular composition, its mode of administration, its mode of activity, and the like.

mmRNA to be delivered and/or pharmaceutical, prophylactic, diagnostic, or imaging compositions thereof may be administered to animals, such as mammals (e.g., humans, domesticated animals, cats, dogs, mice, rats, etc.). In some embodiments, pharmaceutical, prophylactic, diagnostic, or imaging compositions thereof are administered to humans.

mmRNA may be administered by any route. In some embodiments, mmRNA are administered by one or more of a variety of routes, including, but not limited to, local, oral, intravenous, intramuscular, intra-arterial, intramedullary, intrathecal, subcutaneous, intraventricular, transdermal, interdermal, rectal, intravaginal, intraperitoneal, topical (e.g. by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter.

In some embodiments, mmRNA are administered by systemic intravenous injection. In specific embodiments, mmRNA may be administered intravenously and/or orally. In specific embodiments, mmRNA may be administered in a way which allows the mmRNA to cross the blood-brain barrier, vascular barrier, or other epithelial barrier.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Dosage forms for local, topical and/or transdermal administration of a composition may include ointments, pastes, creams, lotions, gels, powders, solutions, sprays, inhalants and/or patches. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

In general the most appropriate route of administration will depend upon a variety of factors including the nature of the mmRNA to be delivered (e.g., its stability in the environment of the gastrointestinal tract, bloodstream, etc.), the condition of the patient (e.g., whether the patient is able to tolerate particular routes of administration), etc. The invention encompasses the delivery of the mmRNA by any appropriate route taking into consideration likely advances in the sciences of drug delivery.

In certain embodiments, compositions in accordance with the present invention may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administration is employed, split dosing regimens such as those described herein may be used.

According to the present invention, it has been discovered that administration of mmRNA in split-dose regimens produce higher levels of proteins in mammalian subjects. As used herein, a "split dose" is the division of single unit dose or total daily dose into two or more doses. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the mmRNA of the present invention are administered to a subject in split doses. The mmRNA may be formulated in buffer only or in a formulation described herein.

Modified nucleic acid molecules or complexes may be used or administered in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually. In one embodiment, the combinations, each or together may be administered according to the split dosing regimens described herein.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer in accordance with the invention may be administered concurrently with a chemotherapeutic agent), or they may achieve different effects (e.g., control of any adverse effects).

Compositions containing mmRNAs are formulated for administration intramuscularly, transarterially, intraocularly, vaginally, rectally, intraperitoneally, intravenously, intranasally, subcutaneously, endoscopically, transdermally, intramuscularly, intraventricularly, intradermally, intrathecally, topically (e.g. by powders, ointments, creams, gels, lotions, and/or drops), mucosally, nasal, enterally, intratumorally, by intratracheal instillation, bronchial instillation, and/or inhalation; nasal spray and/or aerosol, and/or through a portal vein catheter.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like. In some embodiments, the composition is formulated for extended release. In specific embodiments, mmRNA molecules or complexes, and/or pharmaceutical, prophylactic, diagnostic, or imaging compositions thereof, may be administered in a way which allows the mmRNA molecules or complex to cross the blood-brain barrier, vascular barrier, or other epithelial barrier.

In some aspects of the invention, the nucleic acids (particularly ribonucleic acids encoding polypeptides) are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a ribonucleic acid and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. The composition contains an effective amount of a ribonucleic acid engineered to avoid an innate immune response of a cell into which the ribonucleic acid enters, where the ribonucleic acid contains a nucleotide sequence encoding a polypeptide of interest, under conditions such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains a ribonucleic acid that is engineered to avoid an innate immune response of a cell into which the ribonucleic acid enters and encodes the polypeptide of interest and the composition is characterized in that a unit quantity of composition has been determined to produce the polypeptide of interest in a substantial percentage of cells contained within a predetermined volume of the target tissue. In some embodiments, the composition includes a plurality of different ribonucleic acids, where one or more than one of the ribonucleic acids is engineered to avoid an innate immune response of a cell into which the ribonucleic acid enters, and where one or more than one of the ribonucleic acids encodes a polypeptide of interest. Optionally, the composition also contains a cell penetration agent to assist in the intracellular delivery of the ribonucleic acid. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

Formulations which may be administered intramuscularly and/or subcutaneously may include, but are not limited to, polymers, copolymers, and gels. The polymers, copolymers and/or gels may further be adjusted to modify release kinetics by adjusting factors such as, but not limited to, molecular weight, particle size, payload and/or ratio of the monomers. As a non-limiting example, formulations administered intramuscularly and/or subcutaneously may include a copolymer such as poly(lactic-co-glycolic acid).

Localized delivery of the compositions described herein may be administered by methods such as, but not limited to, topical delivery, ocular delivery, transdermal delivery, and the like. The composition may also be administered locally to a part of the body not normally available for localized delivery such as, but not limited to, when a subject's body is open to the environment during treatment. The composition may further be delivered by bathing, soaking and/or surrounding the body part with the composition.

However, the present disclosure encompasses the delivery of mmRNA molecules or complexes, and/or pharmaceutical, prophylactic, diagnostic, or imaging compositions thereof, by any appropriate route taking into consideration likely advances in the sciences of drug delivery.

The level or concentration of a mmRNA may be characterized using exosomes. A level or concentration of the mmRNA in exosomes can represent an expression level, presence, absence, truncation or alteration of the mmRNA. The level or concentration may be determined by a method such as, but not limited to, an assay using construct specific probes, cytometry, qRT-PCR, realtime PCR, PCR, flow cytometry, electrophoresis, mass spectrometry, or combinations thereof. Further, the level or concentration may be associated with a clinical phenotype. For analysis, the exosome may be isolated by a method such as, but not limited to, immunohistochemical methods such as enzyme linked immunosorbent assay (ELISA) methods, size exclusion chromatography, density gradient centrifugation, differential centrifugation, nanomembrane ultrafiltration, immunoabsorbent capture, affinity purification, microfluidic separation, or combinations thereof.

Pharmaceutical Compositions

When administered to a subject the pharmaceutical compositions described herein may provide proteins which have been generated from modified mRNAs. Pharmaceutical compositions may optionally comprise one or more additional therapeutically active substances. In accordance with some embodiments, a method of administering pharmaceutical compositions comprising one or more proteins to be delivered to a subject in need thereof is provided. In some embodiments, compositions are administered to human subjects. In a further embodiment, the compositions are administered to a subject who is a patient.

Pharmaceutical compositions may optionally comprise one or more additional therapeutically active substances.

In some embodiments, compositions are administered to humans. For the purposes of the present disclosure, the phrase “active ingredient” generally refers to a mmRNA to be delivered as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a “unit dose” is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy,* $21^{st}$ Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use.

In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly (vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL®115, GERMABEN®II, NEOLONE™ KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

General considerations in the formulation and/or manufacture of pharmaceutical agents may be found, for example, in *Remington: The Science and Practice of Pharmacy* 21st ed., Lippincott Williams & Wilkins, 2005 (incorporated herein by reference).

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient. Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 m to 500 m. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein Properties of the Pharmaceutical Compositions The pharmaceutical compositions described herein can be characterized by one or more of the following properties:

Bioavailability

The mmRNA molecules, when formulated into a composition with a delivery agent as described herein, can exhibit an increase in bioavailability as compared to a composition lacking a delivery agent as described herein. As used herein, the term "bioavailability" refers to the systemic availability of a given amount of a mmRNA molecule administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a first mmRNA molecule, measured as AUC, $C_{max}$, or $C_{min}$ in a mammal is greater, when co-administered with a delivery agent as described herein, than when such co-administration does not take place. In some embodiments, the bioavailability of the mmRNA molecule can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

The mmRNA molecules, when formulated into a composition as described herein, can exhibit an increase in the therapeutic window of the administered mmRNA molecule composition as compared to the therapeutic window of the administered mmRNA molecule composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the mmRNA molecule when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

The mmRNA molecules, when formulated into a composition as described herein, can exhibit an improved volume of distribution ($V_{dist}$). The volume of distribution ($V_{dist}$) relates the amount of the drug in the body to the concentration of the drug in the blood or plasma. As used herein, the term "volume of distribution" refers to the fluid volume that would be required to contain the total amount of the drug in the body at the same concentration as in the blood or plasma: $V_{dist}$ equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, the volume of distribution of the mmRNA molecule when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Devices and Methods for Multi-Administration

Methods and devices for multi-administration may be employed to deliver the mmRNA of the present invention according to the split dosing regimens taught herein. Such methods and devices are described below.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices may be utilized to deliver the split doses contemplated herein.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

A method for delivering therapeutic agents to a solid tissue has been described by Bahrami et al and is taught for example in US Patent Publication 20110230839, the contents of which are incorporated herein by reference in their entirety. According to Bahrami, an array of needles is incorporated into a device which delivers a substantially equal amount of fluid at any location in said solid tissue along each needle's length.

A device for delivery of biological material across the biological tissue has been described by Kodgule et al and is taught for example in US Patent Publication 20110172610, the contents of which are incorporated herein by reference in their entirety. According to Kodgule, multiple hollow micro-needles made of one or more metals and having outer diameters from about 200 microns to about 350 microns and lengths of at least 100 microns are incorporated into the device which delivers peptides, proteins, carbohydrates, nucleic acid molecules, lipids and other pharmaceutically active ingredients or combinations thereof.

A delivery probe for delivering a therapeutic agent to a tissue has been described by Gunday et al and is taught for example in US Patent Publication 20110270184, the contents of which are incorporated herein by reference in their entirety. According to Gunday, multiple needles are incorporated into the device which moves the attached capsules between an activated position and an inactivated position to force the agent out of the capsules through the needles.

A multiple-injection medical apparatus has been described by Assaf and is taught for example in US Patent Publication 20110218497, the contents of which are incorporated herein by reference in their entirety. According to Assaf, multiple needles are incorporated into the device which has a chamber connected to one or more of said needles and a means for continuously refilling the chamber with the medical fluid after each injection.

An at least partially implantable system for injecting a substance into a patient's body, in particular a penis erection stimulation system has been described by Forsell and is taught for example in US Patent Publication 20110196198, the contents of which are incorporated herein by reference in their entirety. According to Forsell, multiple needles are incorporated into the device which is implanted along with one or more housings adjacent the patient's left and right corpora cavernosa. A reservoir and a pump are also implanted to supply drugs through the needles.

A method for the transdermal delivery of a therapeutic effective amount of iron has been described by Berenson and is taught for example in US Patent Publication 20100130910, the contents of which are incorporated herein by reference in their entirety. According to Berenson, multiple needles may be used to create multiple micro channels in stratum corneum to enhance transdermal delivery of the ionic iron on an iontophoretic patch.

A method for delivery of biological material across the biological tissue has been described by Kodgule et al and is taught for example in US Patent Publication 20110196308, the contents of which are incorporated herein by reference in their entirety. According to Kodgule, multiple biodegradable microneedles containing a therapeutic active ingredient are incorporated in a device which delivers proteins, carbohydrates, nucleic acid molecules, lipids and other pharmaceutically active ingredients or combinations thereof.

A transdermal patch comprising a botulinum toxin composition has been described by Donovan and is taught for example in US Patent Publication 20080220020, the contents of which are incorporated herein by reference in their entirety. According to Donovan, multiple needles are incorporated into the patch which delivers botulinum toxin under stratum corneum through said needles which project through the stratum corneum of the skin without rupturing a blood vessel.

A cryoprobe for administration of an active agent to a location of cryogenic treatment has been described by Toubia and is taught for example in US Patent Publication 20080140061, the contents of which are incorporated herein by reference in their entirety. According to Toubia, multiple needles are incorporated into the probe which receives the active agent into a chamber and administers the agent to the tissue.

A method for treating or preventing inflammation or promoting healthy joints has been described by Stock et al and is taught for example in US Patent Publication 20090155186, the contents of which are incorporated herein by reference in their entirety. According to Stock, multiple needles are incorporated in a device which administers compositions containing signal transduction modulator compounds.

A multi-site injection system has been described by Kimmell et al and is taught for example in US Patent Publication 20100256594, the contents of which are incorporated herein by reference in their entirety. According to Kimmell, multiple needles are incorporated into a device which delivers a medication into a stratum corneum through the needles.

A method for delivering interferons to the intradermal compartment has been described by Dekker et al and is taught for example in US Patent Publication 20050181033, the contents of which are incorporated herein by reference in their entirety. According to Dekker, multiple needles having an outlet with an exposed height between 0 and 1 mm are incorporated into a device which improves pharmacokinetics and bioavailability by delivering the substance at a depth between 0.3 mm and 2 mm.

A method for delivering genes, enzymes and biological agents to tissue cells has described by Desai and is taught for example in US Patent Publication 20030073908, the contents of which are incorporated herein by reference in their entirety. According to Desai, multiple needles are incorporated into a device which is inserted into a body and delivers a medication fluid through said needles.

A method for treating cardiac arrhythmias with fibroblast cells has been described by Lee et al and is taught for example in US Patent Publication 20040005295, the contents of which are incorporated herein by reference in their entirety. According to Lee, multiple needles are incorporated into the device which delivers fibroblast cells into the local region of the tissue.

A method using a magnetically controlled pump for treating a brain tumor has been described by Shachar et al and is taught for example in U.S. Pat. No. 7,799,012 (method) and 7,799,016 (device), the contents of which are incorporated herein by reference in their entirety. According Shachar, multiple needles were incorporated into the pump which pushes a medicating agent through the needles at a controlled rate.

Methods of treating functional disorders of the bladder in mammalian females have been described by Versi et al and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A micro-needle transdermal transport device has been described by Angel et al and is taught for example in U.S. Pat. No. 7,364,568, the contents of which are incorporated herein by reference in their entirety. According to Angel, multiple needles are incorporated into the device which transports a substance into a body surface through the needles which are inserted into the surface from different directions.

A device for subcutaneous infusion has been described by Dalton et al and is taught for example in U.S. Pat. No. 7,150,726, the contents of which are incorporated herein by reference in their entirety. According to Dalton, multiple needles are incorporated into the device which delivers fluid through the needles into a subcutaneous tissue.

A device and a method for intradermal delivery of vaccines and gene therapeutic agents through microcannula have been described by Mikszta et al and are taught for example in U.S. Pat. No. 7,473,247, the contents of which are incorporated herein by reference in their entirety. According to Mitszta, at least one hollow micro-needle is incorporated into the device which delivers the vaccines to the subject's skin to a depth of between 0.025 mm and 2 mm.

A method of delivering insulin has been described by Pettis et al and is taught for example in U.S. Pat. No. 7,722,595, the contents of which are incorporated herein by reference in their entirety. According to Pettis, two needles are incorporated into a device wherein both needles insert essentially simultaneously into the skin with the first at a depth of less than 2.5 mm to deliver insulin to intradermal compartment and the second at a depth of greater than 2.5 mm and less than 5.0 mm to deliver insulin to subcutaneous compartment.

Cutaneous injection delivery under suction has been described by Kochamba et al and is taught for example in U.S. Pat. No. 6,896,666, the contents of which are incorporated herein by reference in their entirety. According to Kochamba, multiple needles in relative adjacency with each other are incorporated into a device which injects a fluid below the cutaneous layer.

A device for withdrawing or delivering a substance through the skin has been described by Down et al and is taught for example in U.S. Pat. No. 6,607,513, the contents of which are incorporated herein by reference in their entirety. According to Down, multiple skin penetrating members which are incorporated into the device have lengths of about 100 microns to about 2000 microns and are about 30 to 50 gauge.

A device for delivering a substance to the skin has been described by Palmer et al and is taught for example in U.S. Pat. No. 6,537,242, the contents of which are incorporated herein by reference in their entirety. According to Palmer, an array of micro-needles is incorporated into the device which uses a stretching assembly to enhance the contact of the needles with the skin and provides a more uniform delivery of the substance.

A perfusion device for localized drug delivery has been described by Zamoyski and is taught for example in U.S. Pat. No. 6,468,247, the contents of which are incorporated herein by reference in their entirety. According to Zamoyski, multiple hypodermic needles are incorporated into the device which injects the contents of the hypodermics into a tissue as said hypodermics are being retracted.

A method for enhanced transport of drugs and biological molecules across tissue by improving the interaction between micro-needles and human skin has been described by Prausnitz et al and is taught for example in U.S. Pat. No. 6,743,211, the contents of which are incorporated herein by reference in their entirety. According to Prausnitz, multiple micro-needles are incorporated into a device which is able to present a more rigid and less deformable surface to which the micro-needles are applied.

A device for intraorgan administration of medicinal agents has been described by Ting et al and is taught for example in U.S. Pat. No. 6,077,251, the contents of which are incorporated herein by reference in their entirety. According to Ting, multiple needles having side openings for enhanced administration are incorporated into a device which by extending and retracting said needles from and into the needle chamber forces a medicinal agent from a reservoir into said needles and injects said medicinal agent into a target organ.

A multiple needle holder and a subcutaneous multiple channel infusion port has been described by Brown and is taught for example in U.S. Pat. No. 4,695,273, the contents of which are incorporated herein by reference in their entirety. According to Brown, multiple needles on the needle holder are inserted through the septum of the infusion port and communicate with isolated chambers in said infusion port.

A dual hypodermic syringe has been described by Horn and is taught for example in U.S. Pat. No. 3,552,394, the contents of which are incorporated herein by reference in their entirety. According to Horn, two needles incorporated into the device are spaced apart less than 68 mm and may be of different styles and lengths, thus enabling injections to be made to different depths.

A syringe with multiple needles and multiple fluid compartments has been described by Hershberg and is taught for example in U.S. Pat. No. 3,572,336, the contents of which are incorporated herein by reference in their entirety. According to Hershberg, multiple needles are incorporated into the syringe which has multiple fluid compartments and is capable of simultaneously administering incompatible drugs which are not able to be mixed for one injection.

A surgical instrument for intradermal injection of fluids has been described by Eliscu et al and is taught for example in U.S. Pat. No. 2,588,623, the contents of which are incorporated herein by reference in their entirety. According to Eliscu, multiple needles are incorporated into the instrument which injects fluids intradermally with a wider disperse.

An apparatus for simultaneous delivery of a substance to multiple breast milk ducts has been described by Hung and is taught for example in EP 1818017, the contents of which are incorporated herein by reference in their entirety. According to Hung, multiple lumens are incorporated into the device which inserts though the orifices of the ductal networks and delivers a fluid to the ductal networks.

A catheter for introduction of medications to the tissue of a heart or other organs has been described by Tkebuchava and is taught for example in WO2006138109, the contents of which are incorporated herein by reference in their entirety. According to Tkebuchava, two curved needles are incorporated which enter the organ wall in a flattened trajectory.

Devices for delivering medical agents have been described by Mckay et al and are taught for example in WO2006118804, the content of which are incorporated herein by reference in their entirety. According to Mckay, multiple needles with multiple orifices on each needle are incorporated into the devices to facilitate regional delivery to a tissue, such as the interior disc space of a spinal disc.

A method for directly delivering an immunomodulatory substance into an intradermal space within a mammalian skin has been described by Pettis and is taught for example in WO2004020014, the contents of which are incorporated herein by reference in their entirety. According to Pettis, multiple needles are incorporated into a device which delivers the substance through the needles to a depth between 0.3 mm and 2 mm.

Methods and devices for administration of substances into at least two compartments in skin for systemic absorption and improved pharmacokinetics have been described by Pettis et al and are taught for example in WO2003094995, the contents of which are incorporated herein by reference in their entirety. According to Pettis, multiple needles having lengths between about 300 μm and about 5 mm are incorporated into a device which delivers to intradermal and subcutaneous tissue compartments simultaneously.

A drug delivery device with needles and a roller has been described by Zimmerman et al and is taught for example in WO2012006259, the contents of which are incorporated herein by reference in their entirety. According to Zimmerman, multiple hollow needles positioned in a roller are incorporated into the device which delivers the content in a reservoir through the needles as the roller rotates.

Methods and Devices Utilizing Catheters and/or Lumens

Methods and devices using catheters and lumens may be employed to administer the mmRNA of the present invention on a split dosing schedule. Such methods and devices are described below.

A catheter-based delivery of skeletal myoblasts to the myocardium of damaged hearts has been described by Jacoby et al and is taught for example in US Patent Publication 20060263338, the contents of which are incorporated herein by reference in their entirety. According to Jacoby, multiple needles are incorporated into the device at least part of which is inserted into a blood vessel and delivers the cell composition through the needles into the localized region of the subject's heart.

An apparatus for treating asthma using neurotoxin has been described by Deem et al and is taught for example in US Patent Publication 20060225742, the contents of which are incorporated herein by reference in their entirety. According to Deem, multiple needles are incorporated into the device which delivers neurotoxin through the needles into the bronchial tissue.

A method for administering multiple-component therapies has been described by Nayak and is taught for example in U.S. Pat. No. 7,699,803, the contents of which are incorporated herein by reference in their entirety. According to Nayak, multiple injection cannulas may be incorporated into a device wherein depth slots may be included for controlling the depth at which the therapeutic substance is delivered within the tissue.

A surgical device for ablating a channel and delivering at least one therapeutic agent into a desired region of the tissue has been described by McIntyre et al and is taught for example in U.S. Pat. No. 8,012,096, the contents of which are incorporated herein by reference in their entirety. According to McIntyre, multiple needles are incorporated into the device which dispenses a therapeutic agent into a region of tissue surrounding the channel and is particularly well suited for transmyocardial revascularization operations.

Methods of treating functional disorders of the bladder in mammalian females have been described by Versi et al and are taught for example in U.S. Pat. No. 8,029,496, the contents of which are incorporated herein by reference in their entirety. According to Versi, an array of micro-needles is incorporated into a device which delivers a therapeutic agent through the needles directly into the trigone of the bladder.

A device and a method for delivering fluid into a flexible biological barrier have been described by Yeshurun et al and are taught for example in U.S. Pat. No. 7,998,119 (device) and 8,007,466 (method), the contents of which are incorporated herein by reference in their entirety. According to Yeshurun, the micro-needles on the device penetrate and extend into the flexible biological barrier and fluid is injected through the bore of the hollow micro-needles.

A method for epicardially injecting a substance into an area of tissue of a heart having an epicardial surface and disposed within a torso has been described by Bonner et al and is taught for example in U.S. Pat. No. 7,628,780, the contents of which are incorporated herein by reference in their entirety. According to Bonner, the devices have elongate shafts and distal injection heads for driving needles into tissue and injecting medical agents into the tissue through the needles.

A device for sealing a puncture has been described by Nielsen et al and is taught for example in U.S. Pat. No. 7,972,358, the contents of which are incorporated herein by reference in their entirety. According to Nielsen, multiple needles are incorporated into the device which delivers a closure agent into the tissue surrounding the puncture tract.

A method for myogenesis and angiogenesis has been described by Chiu et al and is taught for example in U.S. Pat. No. 6,551,338, the contents of which are incorporated herein by reference in their entirety. According to Chiu, 5 to 15 needles having a maximum diameter of at least 1.25 mm and a length effective to provide a puncture depth of 6 to 20 mm are incorporated into a device which inserts into proximity with a myocardium and supplies an exogeneous angiogenic or myogenic factor to said myocardium through the conduits which are in at least some of said needles.

A method for the treatment of prostate tissue has been described by Bolmsj et al and is taught for example in U.S. Pat. No. 6,524,270, the contents of which are incorporated herein by reference in their entirety. According to Bolmsj, a device comprising a catheter which is inserted through the urethra has at least one hollow tip extendible into the surrounding prostate tissue. An astringent and analgesic medicine is administered through said tip into said prostate tissue.

A method for infusing fluids to an intraosseous site has been described by Findlay et al and is taught for example in U.S. Pat. No. 6,761,726, the contents of which are incorporated herein by reference in their entirety. According to Findlay, multiple needles are incorporated into a device which is capable of penetrating a hard shell of material covered by a layer of soft material and delivers a fluid at a predetermined distance below said hard shell of material.

A device for injecting medications into a vessel wall has been described by Vigil et al and is taught for example in U.S. Pat. No. 5,713,863, the contents of which are incorporated herein by reference in their entirety. According to Vigil, multiple injectors are mounted on each of the flexible tubes in the device which introduces a medication fluid through a multi-lumen catheter, into said flexible tubes and out of said injectors for infusion into the vessel wall.

A catheter for delivering therapeutic and/or diagnostic agents to the tissue surrounding a bodily passageway has been described by Faxon et al and is taught for example in U.S. Pat. No. 5,464,395, the contents of which are incorporated herein by reference in their entirety. According to Faxon, at least one needle cannula is incorporated into the catheter which delivers the desired agents to the tissue through said needles which project outboard of the catheter.

Balloon catheters for delivering therapeutic agents have been described by Orr and are taught for example in WO2010024871, the contents of which are incorporated herein by reference in their entirety. According to Orr, multiple needles are incorporated into the devices which deliver the therapeutic agents to different depths within the tissue.

Methods and Devices Utilizing Electrical Current

Methods and devices utilizing electric current may be employed to deliver the mmRNA of the present invention according to the split dosing regimens taught herein. Such methods and devices are described below.

An electro collagen induction therapy device has been described by Marquez and is taught for example in US Patent Publication 20090137945, the contents of which are incorporated herein by reference in their entirety. According to Marquez, multiple needles are incorporated into the device which repeatedly pierce the skin and draw in the skin a portion of the substance which is applied to the skin first.

An electrokinetic system has been described by Etheredge et al and is taught for example in US Patent Publication 20070185432, the contents of which are incorporated herein by reference in their entirety. According to Etheredge, micro-needles are incorporated into a device which drives by an electrical current the medication through the needles into the targeted treatment site.

An iontophoresis device has been described by Matsumura et al and is taught for example in U.S. Pat. No. 7,437,189, the contents of which are incorporated herein by reference in their entirety. According to Matsumura, multiple needles are incorporated into the device which is capable of delivering ionizable drug into a living body at higher speed or with higher efficiency.

Intradermal delivery of biologically active agents by needle-free injection and electroporation has been described by Hoffmann et al and is taught for example in U.S. Pat. No. 7,171,264, the contents of which are incorporated herein by reference in their entirety. According to Hoffmann, one or more needle-free injectors are incorporated into an electroporation device and the combination of needle-free injection and electroporation is sufficient to introduce the agent into cells in skin, muscle or mucosa.

A method for electropermeabilization-mediated intracellular delivery has been described by Lundkvist et al and is taught for example in U.S. Pat. No. 6,625,486, the contents of which are incorporated herein by reference in their entirety. According to Lundkvist, a pair of needle electrodes is incorporated into a catheter. Said catheter is positioned into a body lumen followed by extending said needle electrodes to penetrate into the tissue surrounding said lumen. Then the device introduces an agent through at least one of said needle electrodes and applies electric field by said pair of needle electrodes to allow said agent pass through the cell membranes into the cells at the treatment site.

A delivery system for transdermal immunization has been described by Levin et al and is taught for example in WO2006003659, the contents of which are incorporated herein by reference in their entirety. According to Levin, multiple electrodes are incorporated into the device which applies electrical energy between the electrodes to generate micro channels in the skin to facilitate transdermal delivery.

A method for delivering RF energy into skin has been described by Schomacker and is taught for example in WO2011163264, the contents of which are incorporated herein by reference in their entirety. According to Schomacker, multiple needles are incorporated into a device which applies vacuum to draw skin into contact with a plate so that needles insert into skin through the holes on the plate and deliver RF energy.

Devices and Kits

Devices may also be used in conjunction with the present invention. In one embodiment, a device is used to assess levels of a protein which has been administered in the form of a modified mRNA. The device may comprise a blood, urine or other biofluidic test. It may be as large as to include an automated central lab platform or a small decentralized bench top device. It may be point of care or a handheld device. The device may be useful in drug discovery efforts as a companion diagnostic.

In some embodiments the device is self-contained, and is optionally capable of wireless remote access to obtain instructions for synthesis and/or analysis of the generated nucleic acid. The device is capable of mobile synthesis of at least one nucleic acid, and preferably an unlimited number of different nucleic acid sequences. In certain embodiments, the device is capable of being transported by one or a small number of individuals. In other embodiments, the device is scaled to fit on a benchtop or desk. In other embodiments, the device is scaled to fit into a suitcase, backpack or similarly sized object. In further embodiments, the device is scaled to fit into a vehicle, such as a car, truck or ambulance, or a military vehicle such as a tank or personnel carrier. The information necessary to generate a modified mRNA encoding protein of interest is present within a computer readable medium present in the device.

In some embodiments, the device is capable of communication (e.g., wireless communication) with a database of nucleic acid and polypeptide sequences. The device contains at least one sample block for insertion of one or more sample vessels. Such sample vessels are capable of accepting in liquid or other form any number of materials such as template DNA, nucleotides, enzymes, buffers, and other reagents. The sample vessels are also capable of being heated and cooled by contact with the sample block. The sample block is generally in communication with a device base with one or more electronic control units for the at least one sample block. The sample block preferably contains a heating module, such heating molecule capable of heating and/or cooling the sample vessels and contents thereof to temperatures between about −20 C and above +100 C. The device base is in communication with a voltage supply such as a battery or external voltage supply. The device also contains means for storing and distributing the materials for RNA synthesis.

Optionally, the sample block contains a module for separating the synthesized nucleic acids. Alternatively, the device contains a separation module operably linked to the sample block. Preferably the device contains a means for analysis of the synthesized nucleic acid. Such analysis includes sequence identity (demonstrated such as by hybridization), absence of non-desired sequences, measurement of integrity of synthesized mRNA (such has by microfluidic viscometry combined with spectrophotometry), and concentration and/orpotency of modified RNA (such as by spectrophotometry).

In certain embodiments, the device is combined with a means for detection of pathogens present in a biological material obtained from a subject, e.g., the IBIS PLEX-ID system (Abbott) for microbial identification.

The present invention provides for devices which incorporate mmRNA that encode proteins of interest. These devices may be implantable in an animal subject or may supply mmRNA formulations via a catheter or lumen. The device may be connected to or incorporate a pump. Such devices include those which can deliver therapeutics to areas of the body not readily accessible such as the CNS or across the blood brain barrier. In this embodiment the split dosing regimen can be implemented using a regulated pump.

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits for protein production, comprising a first isolated nucleic acid comprising a translatable region and a nucleic acid modification, wherein the nucleic acid may be capable of evading an innate immune response of a cell into which the first isolated nucleic acid may be introduced, and packaging and instructions. The kit may further comprise a delivery agent to form a formulation composition. The delivery composition may comprise a lipidoid. The lipoid may be selected from, but is not limited to, C12-200, 98N12-5, MD1, DLin-DMA, DLin-K-DMA, DLin-KC2-DMA, DLin-MC3-DMA and analogs thereof.

In one aspect, the present invention provides kits for protein production, comprising a first isolated nucleic acid comprising a translatable region and a nucleoside modification, wherein the nucleic acid exhibits reduced degradation by a cellular nuclease, and packaging and instructions.

In one aspect, the present invention provides kits for protein production, comprising a first isolated nucleic acid comprising a translatable region and at least two different nucleoside modifications, wherein the nucleic acid exhibits reduced degradation by a cellular nuclease, and packaging and instructions.

In some embodiments, kits would provide split doses or instructions for the administration of split dosages of the mmRNA of the kit.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may effect the same outcome or a different outcome. The structure that produces the function may be the same or different. For example, bifunctional modified RNAs of the present invention may encode a cytotoxic peptide (a first function) while those nucleosides which comprise the encoding RNA are, in and of themselves, cytotoxic (second function). In this example, delivery of the bifunctional modified RNA to a cancer cell would produce not only a peptide or protein molecule which may ameliorate or treat the cancer but would also deliver a cytotoxic payload of nucleosides to the cell should degradation, instead of translation of the modified RNA, occur.

Biologically active: As used herein, the phrase "biologically active" refers to a characteristic of any substance that has activity in a biological system and/or organism. For instance, a substance that, when administered to an organism, has a biological affect on that organism, is considered to be biologically active. In particular embodiments, a nucleic acid molecule of the present invention may be considered biologically active if even a portion of the nucleic acid molecule is biologically active or mimics an activity considered biologically relevant.

Chemical terms: As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkoxy" refers to an —O-alkyl group. Example alkoxy groups include methoxy, ethoxy, propoxy (e.g., n-propoxy and isopropoxy), t-butoxy, and the like.

As used herein, "alkenyl" refers to an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, "alkynyl" refers to an alkyl group having one or more triple carbon-carbon bonds. Example alkynyl groups include ethynyl, propynyl, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "halo" or "halogen" includes fluoro, chloro, bromo, and iodo.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a nucleic acid molecule to targeted cells.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, strepavidin and haptens, quantum dots, and the like. Detectable labels may be located at any position in the peptides or proteins disclosed herein. They may be within the amino acids, the peptides, or proteins, or located at the N- or C-termini.

Distal: As used herein "distal" means farther from center mass or line of symmetry of subject or reference point. For limbs, it is farther from body.

Dosing regimen: As used herein, a "dosing regimen" is a schedule of administration or physician determined regimen of treatment, prophylaxis, or palliative care.

Dose splitting factor (DSF)-ratio of PUD of dose split treatment divided by PUD of total daily dose or single unit dose. The value is derived from comparison of dosing regimens groups.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Formulation: As used herein, a "formulation" includes at least a modified nucleic acid molecule and a delivery agent.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (polynucleotide or polypeptide sequences).

In accordance with the invention, two polynucleotide sequences are considered to be homologous if the polypeptides they encode are at least about 50% identical, at least about 60% identical, at least about 70% identical, at least about 80% identical, or at least about 90% identical for at least one stretch of at least about 20 amino acids.

In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Atschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Modified: As used herein "modified" refers to a changed state or structure of a molecule of the invention. Molecules may be modified in many ways including chemically, structurally, and functionally. In one embodiment, the mRNA molecules of the present invention are modified by the introduction of non-natural nucleosides and/or nucleotides. Modified, as it pertains to a modified mRNA may also mean any alteration which is different from the wild type.

Naturally occurring: As used herein, "naturally occurring" means existing in nature without artificial aid.

Patient: As used herein, "patient" refers to a subject who may seek or be in need of treatment, requires treatment, is receiving treatment, will receive treatment, or a subject who is under care by a trained professional for a particular disease or condition.

Peptide: As used herein, "peptide" is less than or equal to 50 amino acids long, e.g., about 5, 10, 15, 20, 25, 30, 35, 40, 45, or 50 amino acids long.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestested in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, $17^{th}$ ed., Mack Publishing Company, Easton, Pa., 1985, p. 1418 and *Journal of Pharmaceutical Science*, 66, 2 (1977), each of which is incorporated herein by reference in its entirety.

Polypeptide: As used herein, "polypeptide" means a polymer of amino acid residues linked together by peptide bonds. The term, as used herein, refers to proteins, polypeptides, and peptides of any size, structure, or function. Typically, however, a polypeptide will be at least 50 amino acids long. In some instances the polypeptide encoded is smaller than about 50 amino acids and the polypeptide is termed a peptide. If the polypeptide is a peptide, it will be at least about 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. The term polypeptide may also apply to amino acid polymers in which one or more amino acid residues are an artificial chemical analogue of a corresponding naturally occurring amino acid.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc divided by the measure in the body fluid.

Proximal: As used herein, "proximal" means closer to center mass or line of symmetry of subject or reference point. For limbs, it is closer to body.

Sample: As used herein, the term "sample" refers to a subset of its tissues, cells or component parts (e.g. body fluids, including but not limited to peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Stable: As used herein "stable" refers to a compound that is sufficiently robust to survive isolation to a useful degree of purity from a reaction mixture, and preferably capable of formulation into an efficacious therapeutic agent.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Simultaneously: As used herein, "simultaneously" means within scientific reproducibility, at same time.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Synthetic: The term "synthetic" means produced, prepared, and/or manufactured by the hand of man. Synthesis of polynucleotides or polypeptides or other molecules of the present invention may be chemical or enzymatic.

Single unit dose: As used herein, a "single unit dose" is a dose of any therapeutic administered in one dose/at one time/single route/single point of contact, i.e., single administration event.

Total daily dose: As used herein, a "total daily dose" is an amount given or prescribed in 24 hr period. It may be administered as a single unit dose.

Split dose: As used herein, a "split dose" is the division of single unit dose or total daily dose into two or more doses.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents, oligonucleotide sequences identified by gene identification numbers, and other publications identified herein are expressly incorporated by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1. Modified mRNA Production

Modified mRNAs (mmRNA) according to the invention may be made using standard laboratory methods and materials. The open reading frame (ORF) of the gene of interest may be flanked by a 5' untranslated region (UTR) which may contain a strong Kozak translational initiation signal and/or an alpha-globin 3' UTR which may include an oligo(dT) sequence for templated addition of a poly-A tail. The modified mRNAs may be modified to reduce the cellular innate immune response. The modifications to reduce the cellular response may include pseudouridine (Ψ) and 5-methyl-cytidine (5meC or $m^5C$). (see, Kariko K et al. Immunity 23:165-75 (2005), Kariko K et al. Mol Ther 16:1833-40 (2008), Anderson B R et al. NAR (2010); herein incorporated by reference).

The ORF may also include various upstream or downstream additions (such as, but not limited to, β-globin, tags, etc.) may be ordered from an optimization service such as, but limited to, DNA2.0 (Menlo Park, CA) and may contain multiple cloning sites which may have XbaI recognition. Upon receipt of the construct, it may be reconstituted and transformed into chemically competent *E. coli.*

For the present invention, NEB DH5-alpha Competent *E. coli* are used. Transformations are performed according to NEB instructions using 100 ng of plasmid. The protocol is as follows:

1. Thaw a tube of NEB 5-alpha Competent *E. coli* cells on ice for 10 minutes.
2. Add 1-5 μl containing 1 pg-100 ng of plasmid DNA to the cell mixture. Carefully flick the tube 4-5 times to mix cells and DNA. Do not vortex.
3. Place the mixture on ice for 30 minutes. Do not mix.
4. Heat shock at 42° C. for exactly 30 seconds. Do not mix.
5. Place on ice for 5 minutes. Do not mix.
6. Pipette 950 μl of room temperature SOC into the mixture.
7. Place at 37° C. for 60 minutes. Shake vigorously (250 rpm) or rotate.
8. Warm selection plates to 37° C.
9. Mix the cells thoroughly by flicking the tube and inverting.
10. Spread 50-100 μl of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 pg), a maxi prep is performed using the Invitrogen PURELINK™ HiPure Maxiprep Kit (Carlsbad, CA), following the manufacturer's instructions.

Figure 2:
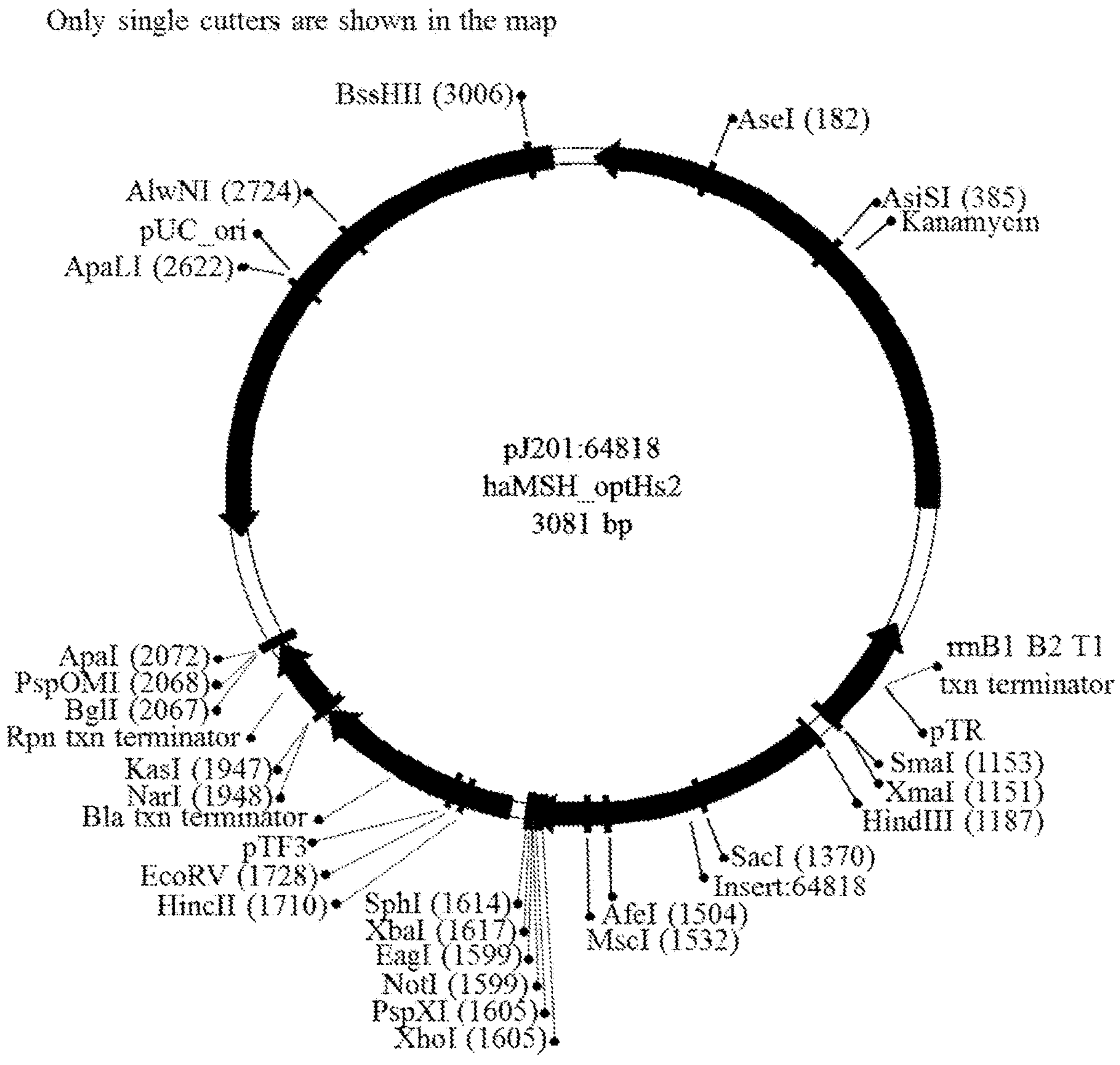
FIG. 2 is a representative plasmid useful in the IVT reactions taught herein. The plasmid contains Insert 64818, designed by the instant inventors.

In order to generate cDNA for In Vitro Transcription (IVT), the plasmid (an Example of which is shown in FIG. 2) is first linearized using a restriction enzyme such as XbaI. A typical restriction digest with XbaI will comprise the following: Plasmid 1.0 pg; 10× Buffer 1.0 μl; XbaI 1.5 μl; $dH_2O$ up to 10 μl; incubated at 37° C. for 1 hr. If performing at lab scale (<5 pg), the reaction is cleaned up using Invitrogen's PURELINK™ PCR Micro Kit (Carlsbad, CA) per manufacturer's instructions. Larger scale purifications may need to be done with a product that has a larger load capacity such as Invitrogen's standard PURELINK™ PCR Kit (Carlsbad, CA). Following the cleanup, the linearized vector is quantified using the NanoDrop and analyzed to confirm linearization using agarose gel electrophoresis.

As a non-limiting example, G-CSF may represent the polypeptide of interest. Sequences used in the steps outlined in Examples 1-5 are shown in Table 2. It should be noted that the start codon (ATG) has been underlined in each sequence of Table 2.

TABLE 2

G-CSF Sequences

| SEQ ID NO | Description |
|---|---|
| 1 | cDNAsequence:<br>ATGGCTGGACCTGCCACCCAGAGCCCCATGAAGCTGATGGCCC<br>TGCAGCTGCTGCTGTGGCACAGTGCACTCTGGACAGTGCAGGA<br>AGCCACCCCCCTGGGCCCTGCCAGCTCCCTGCCCCAGAGCTTC<br>CTGCTCAAGTGCTTAGAGCAAGTGAGGAAGATCCAGGGCGATG<br>GCGCAGCGCTCCAGGAGAAGCTGGTGAGTGAGTGTGCCACCTA<br>CAAGCTGTGCCACCCCGAGGAGCTGGTGCTGCTCGGACACTCT<br>CTGGGCATCCCCTGGGCTCCCCTGAGCAGCTGCCCCAGCCAGG<br>CCCTGCAGCTGGCAGGCTGCTTGAGCCAACTCCATAGCGGCCT<br>TTTCCTCTACCAGGGGCTCCTGCAGGCCCTGGAAGGGATCTCC<br>CCCGAGTTGGGTCCCACCTTGGACACACTGCAGCTGGACGTCG<br>CCGACTTTGCCACCACCATCTGGCAGCAGATGGAAGAACTGGG<br>AATGGCCCCTGCCCTGCAGCCCACCCAGGGTGCCATGCCGGCC<br>TTCGCCTCTGCTTTCCAGCGCCGGGCAGGAGGGGTCCTGGTTG<br>CCTCCCATCTGCAGAGCTTCCTGGAGGTGTCGTACCGCGTTCT<br>ACGCCACCTTGCCCAGCCCTGA |
| 2 | cDNA having T7 polymerase site and Xba restriction site:<br>TTGGACCCTCGTACAGAAGCTAATACGACTCACTATAGGGAAA<br>TAAGAGAGAAAAGAAGAGTAAGAAGAAATATAAGAGCCACCAT<br>GGCTGGACCTGCCACCCAGAGCCCCATGAAGCTGATGGCCCTG<br>CAGCTGCTGCTGTGGCACAGTGCACTCTGGACAGTGCAGGAAG<br>CCACCCCCCTGGGCCCTGCCAGCTCCCTGCCCCAGAGCTTCCT<br>GCTCAAGTGCTTAGAGCAAGTGAGGAAGATCCAGGGCGATGGC<br>GCAGCGCTCCAGGAGAAGCTGGTGAGTGAGTGTGCCACCTACA<br>AGCTGTGCCACCCCGAGGAGCTGGTGCTGCTCGGACACTCTCT<br>GGGCATCCCCTGGGCTCCCCTGAGCAGCTGCCCCAGCCAGGCC<br>CTGCAGCTGGCAGGCTGCTTGAGCCAACTCCATAGCGGCCTTT<br>TCCTCTACCAGGGGCTCCTGCAGGCCCTGGAAGGGATCTCCCC<br>CGAGTTGGGTCCCACCTTGGACACACTGCAGCTGGACGTCGCC<br>GACTTTGCCACCACCATCTGGCAGCAGATGGAAGAACTGGGAA<br>TGGCCCCTGCCCTGCAGCCCACCCAGGGTGCCATGCCGGCCTT<br>CGCCTCTGCTTTCCAGCGCCGGGCAGGAGGGGTCCTGGTTGCC<br>TCCCATCTGCAGAGCTTCCTGGAGGTGTCGTACCGCGTTCTAC<br>GCCACCTTGCCCAGCCCTGAAGCGCTGCCTTCTGCGGGGCTTG<br>CCTTCTGGCCATGCCCTTCTTCTCTCCCTTGCACCTGTACCTC<br>TTGGTCTTTGAATAAAGCCTGAGTAGGAAGGCGGCCGCTCGAG<br>CATGCATCTAGA |
| 3 | Optimized sequence; containing T7 polymerase site and Xba restriction site<br>TTGGACCCTCGTACAGAAGCTAATACGACTCACTATAGGGAAA<br>TAAGAGAGAAAAGAAGAGTAAGAAGAAATATAAGAGCCACCAT<br>GGCCCTGCAGTTGCTGCTTTGGCACTCGGCCCTCTGGACAGTC<br>CAAGAAGCGACTCCTCTCGGACCTGCCTCATCGTTGCCGCAGT<br>CATTCCTTTTGAAGTGTCTGGAGCAGGTGCGAAAGATTCAGGG<br>CGATGGAGCCGCACTCCAAGAGAAGCTCTGCGCGACATACAAA<br>CTTTGCCATCCCGAGGAGCTCGTACTGCTCGGGCACAGCTTGG<br>GGATTCCCTGGGCTCCTCTCTCGTCCTGTCCGTCGCAGGCTTT<br>GCAGTTGGCAGGGTGCCTTTCCCAGCTCCACTCCGGTTTGTTC<br>TTGTATCAGGGACTGCTGCAAGCCCTTGAGGGAATCTCGCCAG<br>AATTGGGCCCGACGCTGGACACGTTGCAGCTCGACGTGGCGGA<br>TTTCGCAACAACCATCTGGCAGCAGATGGAGGAACTGGGGATG<br>GCACCCGCGCTGCAGCCCACGCAGGGGGCAATGCCGGCCTTTG<br>CGTCCGCGTTTCAGCGCAGGGCGGGTGGAGTCCTCGTAGCGAG<br>CCACCTTCAATCATTTTTGGAAGTCTCGTACCGGGTGCTGAGA<br>CATCTTGCGCAGCCGTGAGCCTTCTGCGGGGCTTGCCTTCTGG<br>CCATGCCCTTCTTCTCTCCCTTGCACCTGTACCTCTTGGTCTT<br>TGAATAAAGCCTGAGTAGGAAGGCGGCCGCTCGAGCATGCA |
| 4 | mRNA sequence (transcribed)<br>CUCACUAUAGGGAAAUAAGAGAGAAAAGAAGAGUAAGAAGAAA<br>UAUAAGAGCCACCAAUGGCCCUGCAGUUGCUGCUUUGGCACUC<br>GGCCCUCUGGACAGUCCAAGAAGCGACUCCUCUCGGACCUGCC<br>UCAUCGUUGCCGCAGUCAUUCCUUUUGAAGUGUCUGGAGCAGG<br>UGCGAAAGAUUCAGGGCGAUGGAGCCGCACUCCAAGAGAAGCU<br>CUGCGCGACAUACAAACUUUGCCAUCCCGAGGAGCUCGUACUG<br>CUCGGGCACAGCUUGGGGAUUCCCUGGGCUCCUCUCUCGUCCU<br>GUCCGUCGCAGGCUUUGCAGUUGGCAGGGUGCCUUUCCCAGCU<br>CCACUCCGGUUUGUUCUUGUAUCAGGGACUGCUGCAAGCCCUU<br>GAGGGAAUCUCGCCAGAAUUGGGCCCGACGCUGGACACGUUGC<br>AGCUCGACGUGGCGGAUUUCGCAACAACCAUCUGGCAGCAGAU<br>GGAGGAACUGGGGAUGGCACCCGCGCUGCAGCCCACGCAGGGG<br>GCAAUGCCGGCCUUUGCGUCCGCGUUUCAGCGCAGGGCGGGUG<br>GAGUCCUCGUAGCGAGCCACCUUCAAUCAUUUUUGGAAGUCUC<br>GUACCGGGUGCUGAGACAUCUUGCGCAGCCGUGAGCCUUCUGC<br>GGGGCUUGCCUUCUGGCCAUGCCCUUCUUCUCUCCCUUGCACC<br>UGUACCUCUUGGUCUUUGAAUAAAGCCUGAGUAGGAAGGCGGC<br>CGCUCGAGCAUGCAU |

Example 2: PCR for cDNA Production

PCR procedures for the preparation of cDNA are performed using 2×KAPA HIFI™ HotStart ReadyMix by Kapa Biosystems (Woburn, MA). This system includes 2×KAPA ReadyMix12.5 μl; Forward Primer (10 uM) 0.75 μl; Reverse Primer (10 uM) 0.75 μl; Template cDNA 100 ng; and $dH_2O$ diluted to 25.0 μl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention incorporates a poly-$T_{120}$ for a poly-$A_{120}$ in the mRNA. Other reverse primers with longer or shorter poly(T) tracts can be used to adjust the length of the poly(A) tail in the mRNA.

The reaction is cleaned up using Invitrogen's PURELINK™ PCR Micro Kit (Carlsbad, CA) per manufacturer's instructions (up to 5 pg). Larger reactions will require a cleanup using a product with a larger capacity. Following the cleanup, the cDNA is quantified using the NanoDrop and analyzed by agarose gel electrophoresis to confirm the cDNA is the expected size. The cDNA is then submitted for sequencing analysis before proceeding to the in vitro transcription reaction.

Example 3. In Vitro Transcription (IVT)

The in vitro transcription reaction generates mRNA containing modified nucleotides or modified RNA. The input nucleotide triphosphate (NTP) mix is made in-house using natural and un-natural NTPs.

A typical in vitro transcription reaction includes the following:

| | | |
|---|---|---|
| 1. | Template cDNA | 1.0 μg |
| 2. | 10x transcription buffer (400 mM Tris-HCl pH 8.0, 190 mM $MgCl_2$, 50 mM DTT, 10 mM Spermidine) | 2.0 μl |
| 3. | Custom NTPs (25 mM each) | 7.2 μl |
| 4. | RNase Inhibitor | 20 U |
| 5. | T7 RNA polymerase | 3000 U |
| 6. | $dH_20$ | Up to 20.0 μl. and |
| 7. | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, TX) following the manufacturer's instructions. This kit can purify up to 500 μg of RNA. Following the cleanup, the RNA is quantified using the NanoDrop and analyzed by agarose gel electrophoresis to confirm the RNA is the proper size and that no degradation of the RNA has occurred.

Example 4. Enzymatic Capping of mRNA

Capping of the mRNA is performed as follows where the mixture includes: IVT RNA 60 μg-180 μg and $dH_2O$ up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400 U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The mRNA is then purified using Ambion's MEGACLEAR™ Kit (Austin, TX) following the manufacturer's instructions. Following the cleanup, the RNA is quantified using the NANODROP™ (ThermoFisher, Waltham, MA) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 5. PolyA Tailing Reaction

Without a poly-T in the cDNA, a poly-A tailing reaction must be performed before cleaning the final product. This is done by mixing Capped IVT RNA (100 μl); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubation at 37° C. for 30 min. If the poly-A tail is already in the transcript, then the tailing reaction may be skipped and proceed directly to cleanup with Ambion's MEGACLEAR™ kit (Austin, TX) (up to 500 μg). Poly-A Polymerase is preferably a recombinant enzyme expressed in yeast.

For studies performed and described herein, the poly-A tail is encoded in the IVT template to comprise 160 nucleotides in length. However, it should be understood that the processivity or integrity of the Poly-A tailing reaction may not always result in exactly 160 nucleotides. Hence Poly-A tails of approximately 160 nucleotides, e.g, about 150-165, 155, 156, 157, 158, 159, 160, 161, 162, 163, 164 or 165 are within the scope of the invention.

Example 6. Formulation of Modified mRNA Using Lipidoids

5'-capping of modified RNA may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 7. Capping

A. Protein Expression Assay

Synthetic mRNAs encoding human G-CSF (cDNA shown in SEQ ID NO: 1) containing the ARCA (3' O-Me-m7G(5')ppp(5')G) cap analog or the Cap1 structure can be transfected into human primary keratinocytes at equal concentrations. 6, 12, 24 and 36 hours post-transfection the amount of G-CSF secreted into the culture medium can be assayed by ELISA. Synthetic mRNAs that secrete higher levels of G-CSF into the medium would correspond to a synthetic mRNA with a higher translationally-competent Cap structure.

B. Purity Analysis Synthesis mRNAs encoding human G-CSF (cDNA shown in SEQ ID NO: 1) containing the ARCA cap analog or the Cap1 structure crude synthesis products can be compared for purity using denaturing Agarose-Urea gel electrophoresis or HPLC analysis. Synthetic mRNAs with a single, consolidated band by electrophoresis correspond to the higher purity product compared to a synthetic mRNA with multiple bands or streaking bands. Synthetic mRNAs with a single HPLC peak would also correspond to a higher purity product. The capping reaction with a higher efficiency would provide a more pure mRNA population.

C. Cytokine Analysis

Synthetic mRNAs encoding human G-CSF (cDNA shown in SEQ ID NO: 1) containing the ARCA cap analog or the Cap1 structure can be transfected into human primary keratinocytes at multiple concentrations. 6, 12, 24 and 36 hours post-transfection the amount of pro-inflammatory cytokines such as TNF-alpha and IFN-beta secreted into the culture medium can be assayed by ELISA. Synthetic mRNAs that secrete higher levels of pro-inflammatory cytokines into the medium would correspond to a synthetic mRNA containing an immune-activating cap structure.

D. Capping Reaction Efficiency

Synthetic mRNAs encoding human G-CSF (cDNA shown in SEQ ID NO: 1) containing the ARCA cap analog or the Cap1 structure can be analyzed for capping reaction efficiency by LC-MS after capped mRNA nuclease treatment. Nuclease treatment of capped mRNAs would yield a mixture of free nucleotides and the capped 5'-5-triphosphate cap structure detectable by LC-MS. The amount of capped product on the LC-MS spectra can be expressed as a percent of total mRNA from the reaction and would correspond to capping reaction efficiency. The cap structure with a higher capping reaction efficiency would have a higher amount of capped product by LC-MS.

Example 8. Formulation of Modified mRNA Using Lipidoids

Modified mRNAs (mmRNA) are formulated for in vitro experiments by mixing the mmRNA with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations was used as a starting point. Initial mmRNA-lipidoid formulations may consist of particles composed of 42% lipidoid, 48% cholesterol and 10% PEG, with further optimization of ratios possible. After formation of the particle, mmRNA is added and allowed to integrate with the complex. The encapsulation efficiency is determined using a standard dye exclusion assays.

Materials and Methods for Examples 9-13

A. Lipid Synthesis

Six lipids, DLin-DMA, DLin-K-DMA, DLin-KC2-DMA, 98N12-5, C12-200 and DLin-MC3-DMA, were synthesized by methods outlined in the art in order to be formulated with modified RNA. DLin-DMA and precursors were synthesized as described in Heyes et. al, J. Control Release, 2005, 107, 276-287. DLin-K-DMA and DLin-KC2-DMA and precursors were synthesized as described in Semple et. al, *Nature Biotechnology,* 2010, 28, 172-176. 98N12-5 and precursor were synthesized as described in Akinc et. al, *Nature Biotechnology,* 2008, 26, 561-569.

C12-200 and precursors were synthesized according to the method outlined in Love et. al, PNAS, 2010, 107, 1864-1869. 2-epoxydodecane (5.10 g, 27.7 mmol, 8.2 eq) was added to a vial containing Amine 200 (0.723 g, 3.36 mmol, 1 eq) and a stirring bar. The vial was sealed and warmed to 80° C. The reaction was stirred for 4 days at 80° C. Then the mixture was purified by silica gel chromatography using a gradient from pure dichloromethane (DCM) to DCM:MeOH 98:2. The target compound was further purified by RP-HPLC to afford the desired compound.

DLin-MC3-DMA and precursors were synthesized according to procedures described in WO 2010054401 herein incorporated by reference in its entirety. A mixture of dilinoleyl methanol (1.5 g, 2.8 mmol, 1 eq), N,N-dimethyl-aminobutyric acid (1.5 g, 2.8 mmol, 1 eq), DIPEA (0.73 mL, 4.2 mmol, 1.5 eq) and TBTU (1.35 g, 4.2 mmol, 1.5 eq) in 10 mL of DMF was stirred for 10 h at room temperature. Then the reaction mixture was diluted in ether and washed with water. The organic layer was dried over anhydrous sodium sulfate, filtrated and concentrated under reduced pressure. The crude product was purified by silica gel chromatography using a gradient DCM to DCM:MeOH 98:2. Subsequently the target compound was subjected to an additional RP-HPLC purification which was done using a YMC—Pack C4 column to afford the target compound.

B. Formulation of Modified RNA Nanoparticles

Solutions of synthesized lipid, 1,2-distearoyl-3-phosphatidylcholine (DSPC) (Avanti Polar Lipids, Alabaster, AL), cholesterol (Sigma-Aldrich, Taufkirchen, Germany), and α-[3'-(1,2-dimyristoyl-3-propanoxy)-carboxamide-propyl]-ω-methoxy-polyoxyethylene (PEG-c-DOMG) (NOF, Bouwelven, Belgium) were prepared at concentrations of 50 mM in ethanol and stored at −20° C. The lipids were combined to yield molar ratio of 50:10:38.5:1.5 (Lipid: DSPC:Cholesterol:PEG-c-DOMG) and diluted with ethanol to a final lipid concentration of 25 mM. Solutions of modified mRNA at a concentration of 1-2 mg/mL in water were diluted in 50 mM sodium citrate buffer at a pH of 3 to form a stock modified mRNA solution. Formulations of the lipid and modified mRNA were prepared by combining the synthesized lipid solution with the modified mRNA solution at total lipid to modified mRNA weight ratio of 10:1, 15:1, 20:1 and 30:1. The lipid ethanolic solution was rapidly injected into aqueous modified mRNA solution to afford a suspension containing 33% ethanol. The solutions were injected either manually (MI) or by the aid of a syringe pump (SP) (Harvard Pump 33 Dual Syringe Pump Harvard Apparatus Holliston, MA).

To remove the ethanol and to achieve the buffer exchange, the formulations were dialyzed twice against phosphate buffered saline (PBS), pH 7.4 at volumes 200-times of the primary product using a Slide-A-Lyzer cassettes (Thermo Fisher Scientific Inc. Rockford, IL) with a molecular weight cutoff (MWCO) of 10 kD. The first dialysis was carried at room temperature for 3 hours and then the formulations were dialyzed overnight at 4° C. The resulting nanoparticle suspension was filtered through 0.2 μm sterile filter (Sarstedt, Numbrecht, Germany) into glass vials and sealed with a crimp closure.

C. Characterization of Formulations

A Zetasizer Nano ZS (Malvern Instruments Ltd, Malvern, Worcestershire, UK) was used to determine the particle size, the polydispersity index (PDI) and the zeta potential of the modified mRNA nanoparticles in 1×PBS in determining particle size and 15 mM PBS in determining zeta potential.

Ultraviolet-visible spectroscopy was used to determine the concentration of modified mRNA nanoparticle formulation. 100 μL of the diluted formulation in 1×PBS was added to 900 μL of a 4:1 (v/v) mixture of methanol and chloroform. After mixing, the absorbance spectrum of the solution was recorded between 230 nm and 330 nm on a DU 800 spectrophotometer (Beckman Coulter, Beckman Coulter, Inc., Brea, CA). The modified RNA concentration in the nanoparticle formulation was calculated based on the extinction coefficient of the modified RNA used in the formulation and on the difference between the absorbance at a wavelength of 260 nm and the baseline value at a wavelength of 330 nm.

QUANT-IT™ RIBOGREEN® RNA assay (Invitrogen Corporation Carlsbad, CA) was used to evaluate the encapsulation of modified RNA by the nanoparticle. The samples were diluted to a concentration of approximately 5 μg/mL in TE buffer (10 mM Tris-HCl, 1 mM EDTA, pH 7.5). 50 μL of the diluted samples were transferred to a polystyrene 96 well plate, then either 50 μL of TE buffer or 50 μL of a 2% Triton X-100 solution was added. The plate was incubated at a temperature of 37° C. for 15 minutes. The RIBOGREEN® reagent was diluted 1:100 in TE buffer, 100 μL of this solution was added to each well. The fluorescence intensity was measured using a fluorescence plate reader (Wallac Victor 1420 Multilablel Counter; Perkin Elmer, Waltham, MA) at an excitation wavelength of ~480 nm and an emission wavelength of ~520 nm. The fluorescence values of the reagent blank were subtracted from that of each of the samples and the percentage of free modified RNA was determined by dividing the fluorescence intensity of the intact sample (without addition of Triton X-100) by the fluorescence value of the disrupted sample (caused by the addition of Triton X-100).

D. In Vitro Incubation

Human embryonic kidney epithelial (HEK293) and hepatocellular carcinoma epithelial (HepG2) cells (LGC standards GmbH, Wesel, Germany) were seeded on 96-well plates (Greiner Bio-one GmbH, Frickenhausen, Germany) and plates for HEK293 cells were precoated with collagen type1. HEK293 were seeded at a density of 30,000 and HepG2 were seeded at a density of 35,000 cells per well in 100 μl cell culture medium. For HEK293 the cell culture medium was DMEM, 10% FCS, adding 2 mM L-Glutamine, 1 mM Sodiumpyruvate and 1× non-essential amino acids (Biochrom AG, Berlin, Germany) and 1.2 mg/ml Sodiumbicarbonate (Sigma-Aldrich, Munich, Germany) and for HepG2 the culture medium was MEM (Gibco Life Technologies, Darmstadt, Germany), 10% FCS adding 2 mM L-Glutamine, 1 mM Sodiumpyruvate and 1× non-essential amino acids (Biochrom AG, Berlin, Germany. Formulations containing mCherry mRNA (mRNA sequence shown in SEQ ID NO: 5; poly-A tail of approximately 160 nucleotides not shown in sequence; 5' cap, Cap1) were added in quadruplicates directly after seeding the cells and incubated. The mCherry cDNA with the T7 promoter, 5'untranslated region (UTR) and 3' UTR used in in vitro transcription (IVT) is given in SEQ ID NO: 6.

Cells were harvested by transferring the culture media supernatants to a 96-well Pro-Bind U-bottom plate (Beckton Dickinson GmbH, Heidelberg, Germany). Cells were trypsinized with ½ volume Trypsin/EDTA (Biochrom AG, Berlin, Germany), pooled with respective supernatants and fixed by adding one volume PBS/2% FCS (both Biochrom AG, Berlin, Germany)/0.5% formaldehyde (Merck, Darmstadt, Germany). Samples then were submitted to a flow cytometer measurement with a 532 nm excitation laser and the 610/20 filter for PE-Texas Red in a LSRII cytometer (Beckton Dickinson GmbH, Heidelberg, Germany). The mean fluorescence intensity (MFI) of all events and the standard deviation of four independent wells are presented in for samples analyzed.

Example 9. Purification on Nanoparticle Formulations

Figure 3A:
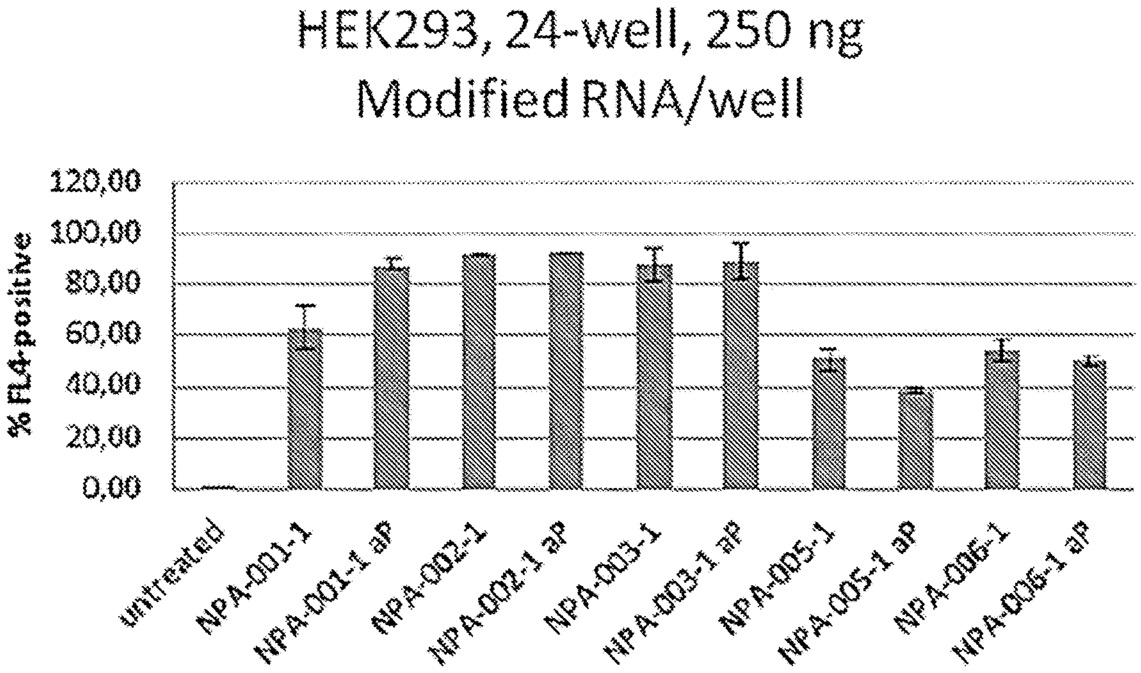
FIGS. 3A and 3B are histograms showing in vitro screening results for nanoparticle formulations of DLin-KC2-DMA and 98N12-15 (before and after purification) that contain mCherry mmRNA.
Figure 3B:
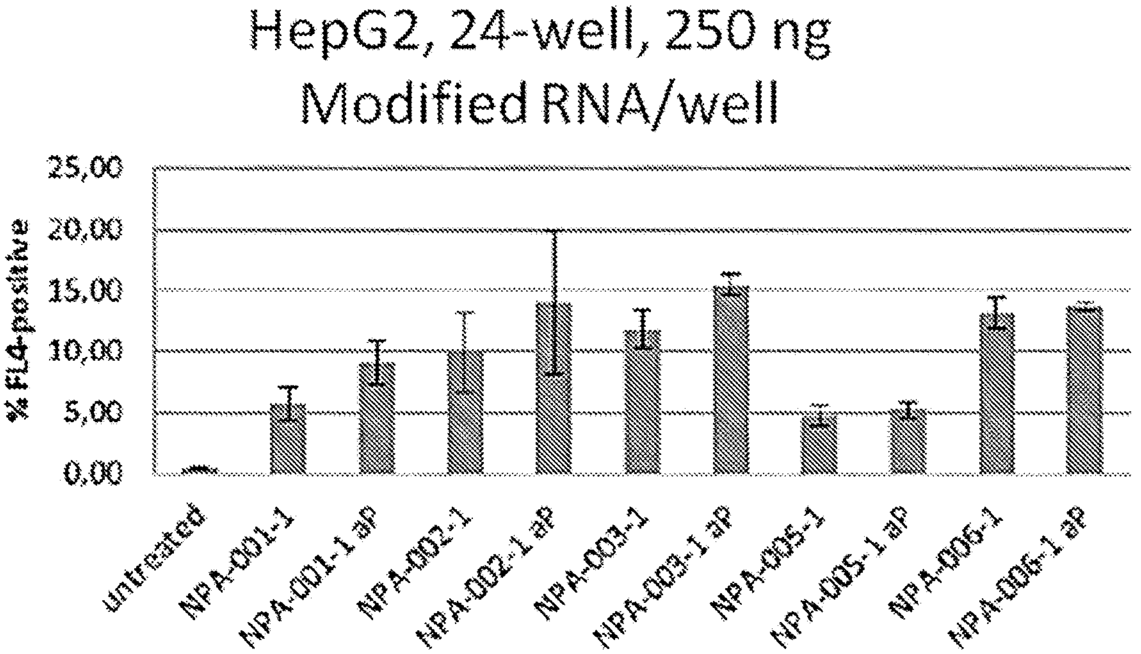
Figure 4A:
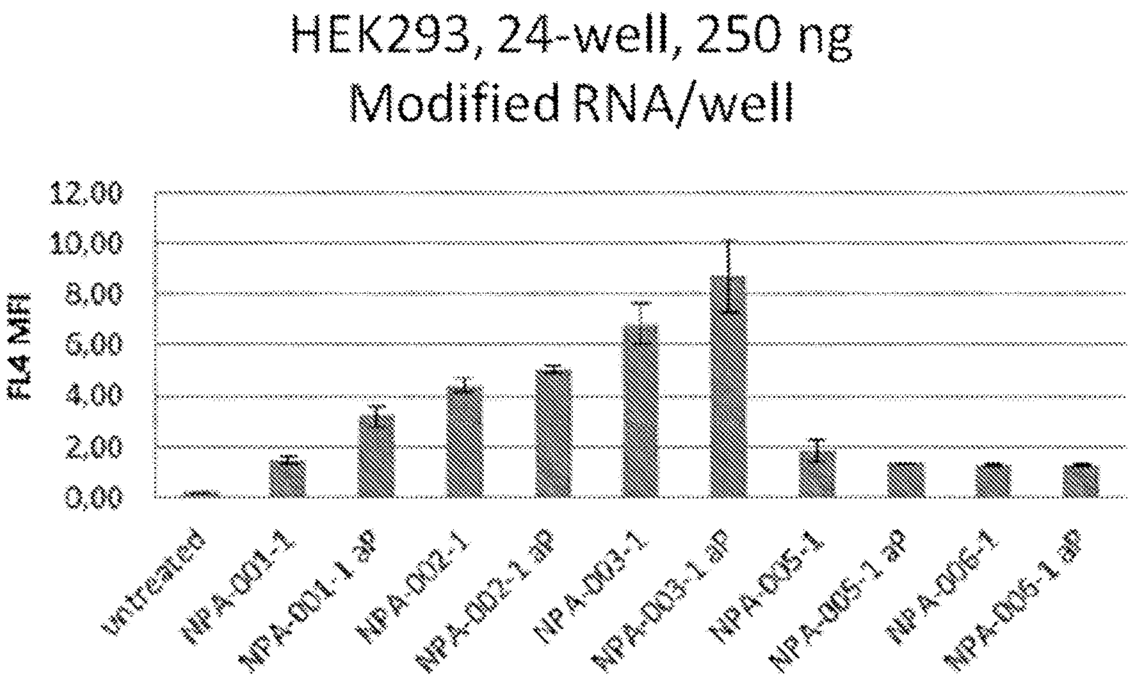
FIGS. 4A and 4B are histograms showing in vitro screening results for mean fluorescence intensity for nanoparticle formulations of DLin-KC2-DMA and 98N12-15 (before and after purification) that contain mCherry mmRNA.
Figure 4B:
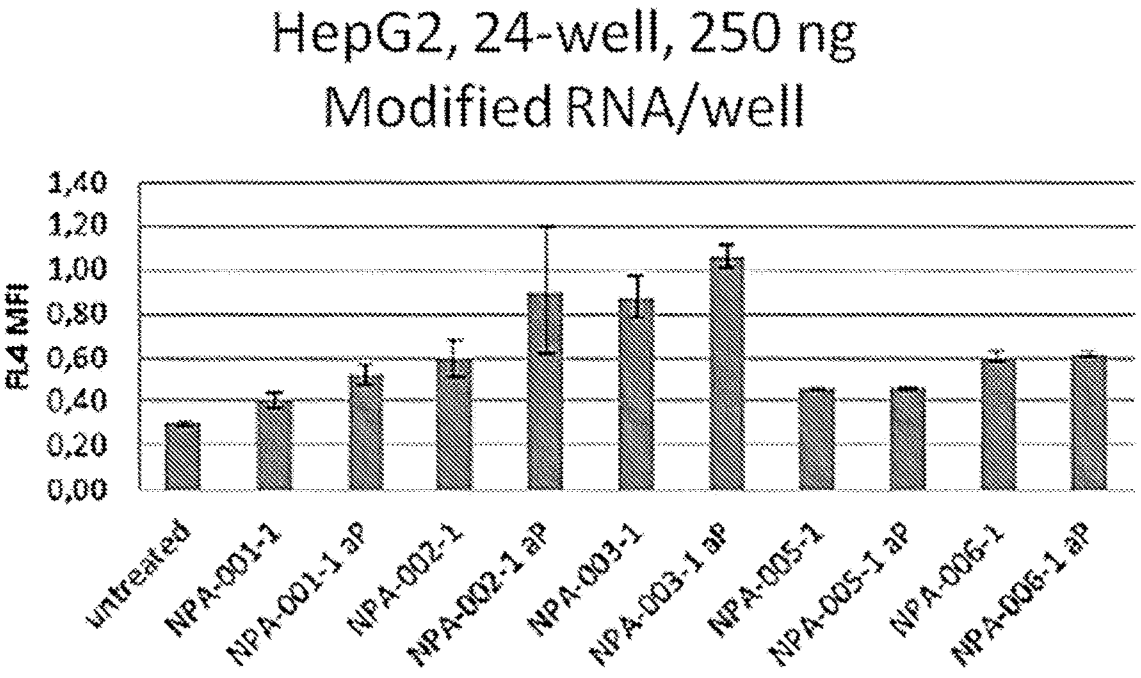

Nanoparticle formulations of DLin-KC2-DMA and 98N12-5 in HEK293 and HepG2 were tested to determine if the mean fluorescent intensity (MFI) was dependent on the lipid to modified RNA ratio and/or purification. Three formulations of DLin-KC2-DMA and two formulations of 98N12-5 were produced using a syringe pump to the specifications described in Table 3. Purified samples were purified by SEPHADEX™ G-25 DNA grade (GE Healthcare, Sweden). Each formulation before and after purification (aP) were tested at concentration of 250 ng modified RNA per well in a 24 well plate. The percentage of cells that are positive for the marker for FL4 channel (% FL4-positive) when analyzed by the flow cytometer for each formulation and the background sample are shown in FIGS. 3A and 3B, and the MFI of the marker for the FL4 channel for each formulation and the background sample are shown in FIGS. 4A and 4B. The formulations which had been purified had a slightly higher MFI than those formulations tested before purification.

TABLE 3

| Formulations | | | |
|---|---|---|---|
| Formulation # | Lipid | Lipid/RNA wt/wt | Mean size (nm) |
| NPA-001-1 | DLin-KC2-DMA | 10 | 155 nm PDI: 0.08 |
| NPA-001-1 aP | DLin-KC2-DMA | 10 | 141 nm PDI: 0.14 |
| NPA-002-1 | DLin-KC2-DMA | 15 | 140 nm PDI: 0.11 |
| NPA-002-1 aP | DLin-KC2-DMA | 15 | 125 nm PDI: 0.12 |
| NPA-003-1 | DLin-KC2-DMA | 20 | 114 nm PDI: 0.08 |
| NPA-003-1 aP | DLin-KC2-DMA | 20 | 104 nm PDI: 0.06 |
| NPA-005-1 | 98N12-5 | 15 | 127 nm PDI: 0.12 |
| NPA-005-1 aP | 98N12-5 | 15 | 134 nm PDI: 0.17 |
| NPA-006-1 | 98N12 | 20 | 126 nm PDI: 0.08 |
| NPA-006-1 aP | 98N12 | 20 | 118 nm PDI: 0.13 |

Example 10. Concentration Response Curve

Figure 5A:
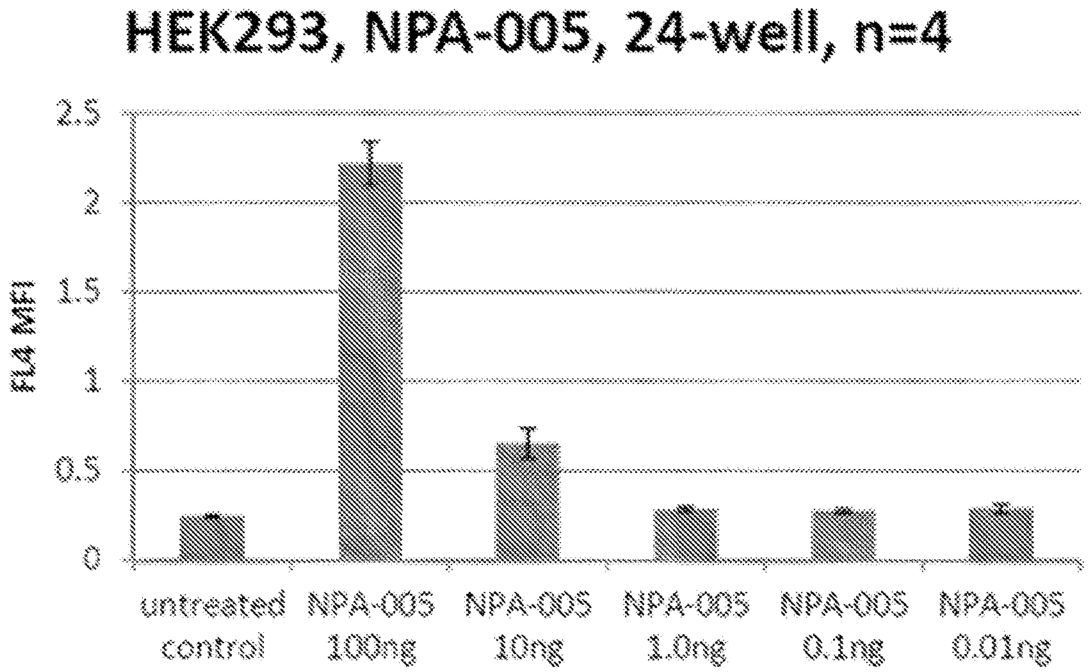
FIGS. 5A, 5B, and 5C are histograms showing in vitro screening results for nanoparticle formulations of DLin-KC2-DMA and 98N12-15 before and after purification.
Figure 5B:
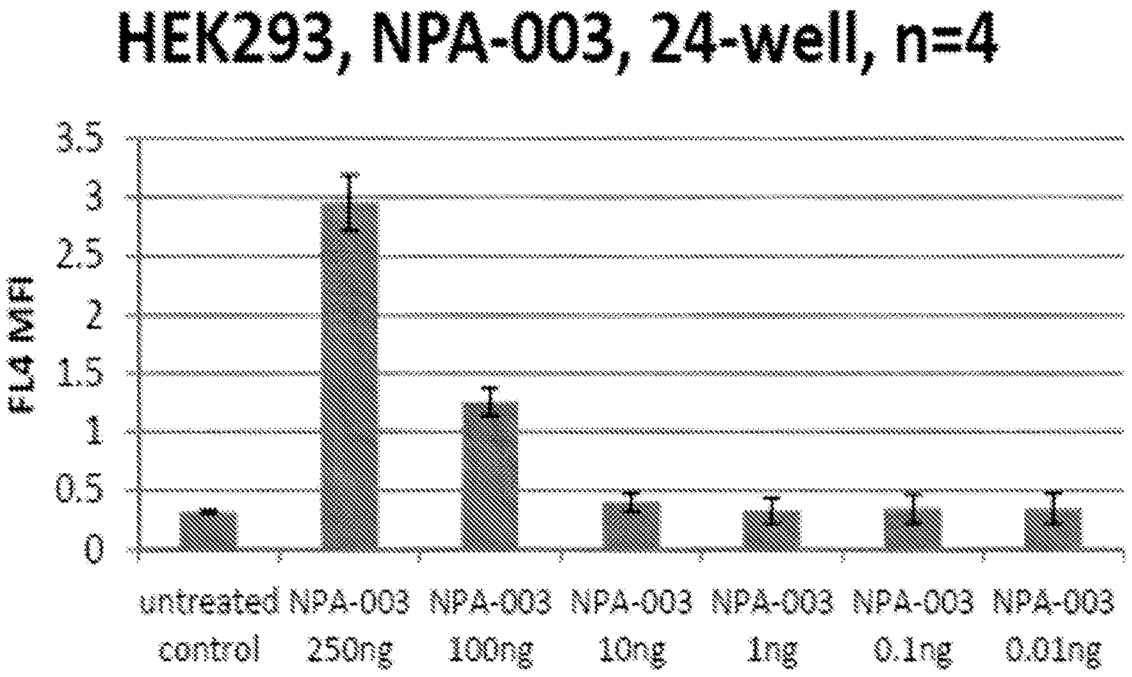
Figure 5C:
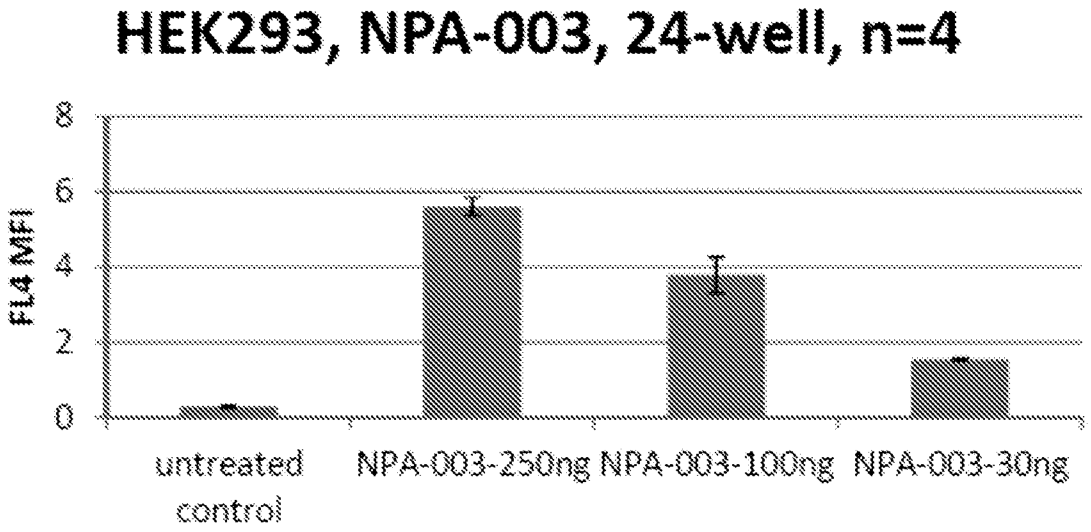

Nanoparticle formulations of 98N12-5 (NPA-005) and DLin-KC2-DMA (NPA-003) were tested at varying concentrations to determine the MFI of FL4 or mCherry (mRNA sequence shown in SEQ ID NO: 5; poly-A tail of approximately 160 nucleotides not shown in sequence; 5' cap, Cap 1) over a range of doses. The formulations tested are outlined in Table 4. To determine the optimal concentration of nanoparticle formulations of 98N12-5, varying concentrations of formulated modified RNA (100 ng, 10 ng, 1.0 ng, 0.1 ng and 0.01 ng per well) were tested in a 24-well plate of HEK293, and the results of the FL4 MFI of each dose are shown in FIG. 5A. Likewise, to determine the optimal concentration of nanoparticle formulations of DLin-KC2-DMA, varying concentrations of formulated modified RNA (250 ng 100 ng, 10 ng, 1.0 ng, 0.1 ng and 0.01 ng per well) were tested in a 24-well plate of HEK293, and the results of the FL4 MFI of each dose are shown in FIG. 5B. Nanoparticle formulations of DLin-KC2-DMA were also tested at varying concentrations of formulated modified RNA (250 ng, 100 ng and 30 ng per well) in a 24 well plate of HEK293, and the results of the FL4 MFI of each dose are shown in FIG. 5C. A dose of 1 ng/well for 98N12-5 and a dose of 10 ng/well for DLin-K2-DMA were found to resemble the FL4 MFI of the background.

To determine how close the concentrations resembled the background, we utilized a flow cytometer with optimized filter sets for detection of mCherry expression, and were able to obtain results with increased sensitivity relative to background levels. Doses of 25 ng/well, 0.25 ng/well, 0.025 ng/well and 0.0025 ng/well were analyzed for 98N12-5 (NPA-005) and DLin-K2-DMA (NPA-003) to determine the MFI of mCherry. As shown in Table 5, the concentration of 0.025 ng/well and lesser concentrations are similar to the background MFI level of mCherry which is about 386.125.

TABLE 4

| Formulations | | |
|---|---|---|
| Formulation # | NPA-003 | NPA-005 |
| Lipid | DLin-KC2-DMA | 98N12-5 |
| Lipid/RNA wt/wt | 20 | 15 |
| Mean size | 114 nm<br>PDI: 0.08 | 106 nm<br>PDI: 0.12 |

TABLE 5

| Concentration and MFI | | |
|---|---|---|
| | MFI mCherry | |
| Formulation | NPA-003 | NPA-005 |
| 25 ng/well | 11963.25 | 12256.75 |
| 0.25 ng/well | 1349.75 | 2572.75 |
| 0.025 ng/well | 459.50 | 534.75 |
| 0.0025 ng/well | 310.75 | 471.75 |

Example 11. Manual Injection and Syringe Pump Formulations

Two formulations of DLin-KC2-DMA and 98N12-5 were prepared by manual injection (MI) and syringe pump injection (SP) and analyzed along with a background sample to compare the MFI of mCherry (mRNA shown in SEQ ID NO: 5; poly-A tail of approximately 160 nucleotides not shown in sequence; 5' cap, Cap1) of the different formulations. Table 5 shows that the syringe pump formulations had a higher MFI as compared to the manual injection formulations of the same lipid and lipid/RNA ratio.

TABLE 5

| Formulations and MFI | | | | | |
|---|---|---|---|---|---|
| Formulation # | Lipid | Lipid/ RNA wt/wt | Mean size (nm) | Method of formulation | MFI |
| Untreated Control | N/A | N/A | N/A | N/A | 674.67 |
| NPA-002 | DLin-KC2-DMA | 15 | 140 nm<br>PDI: 0.11 | MI | 10318.25 |
| NPA-002-2 | DLin-KC2-DMA | 15 | 105 nm<br>PDI: 0.04 | SP | 37054.75 |
| NPA-003 | DLin-KC2-DMA | 20 | 114 nm<br>PDI: 0.08 | MI | 22037.5 |
| NPA-003-2 | DLin-KC2-DMA | 20 | 95 nm<br>PDI: 0.02 | SP | 37868.75 |
| NPA-005 | 98N12-5 | 15 | 127 nm<br>PDI: 0.12 | MI | 11504.75 |
| NPA-005-2 | 98N12-5 | 15 | 106 nm<br>PDI: 0.07 | SP | 9343.75 |
| NPA-006 | 98N12-5 | 20 | 126 nm<br>PDI: 0.08 | MI | 11182.25 |
| NPA-006-2 | 98N12-5 | 20 | 93 nm<br>PDI: 0.08 | SP | 5167 |

Example 12. mCherry Fluorescence of Formulations

Figure 6A:
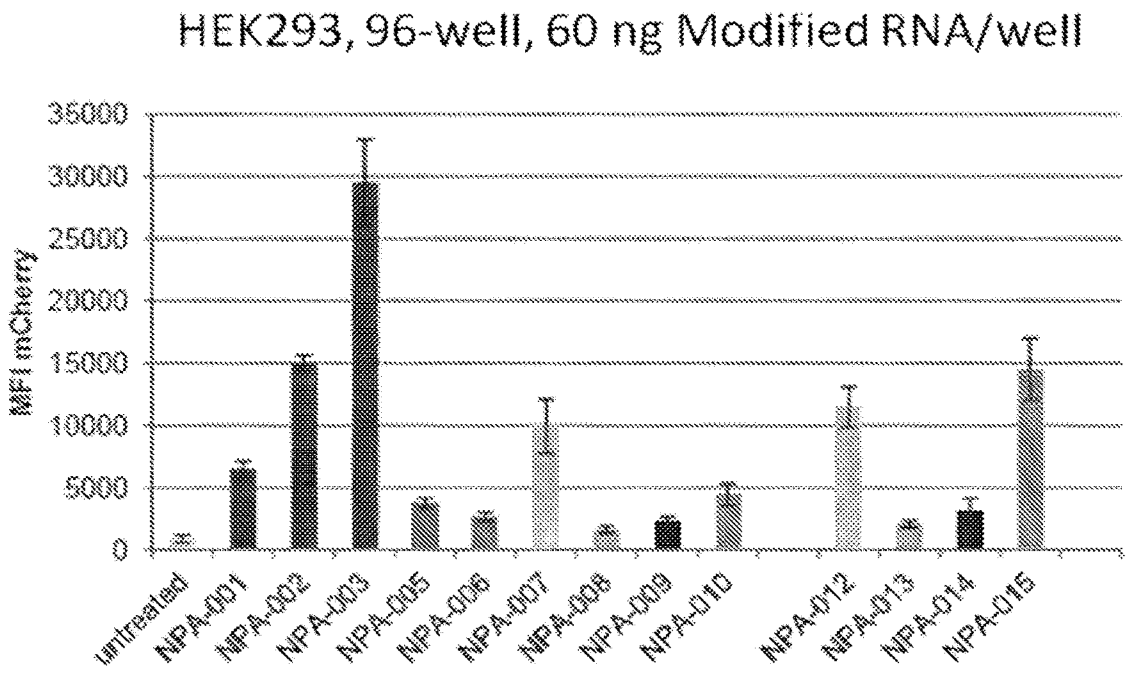
FIGS. 6A, 6B, 6C, 6D, and 6E are histograms showing in vitro screening results for nanoparticle formulations of DLin-DMA, DLin-K-DMA, DLin-KC2-DMA, 98N12-5, C12-200 and DLin-MC3-DMA that contain mCherry mmRNA.
Figure 6B:
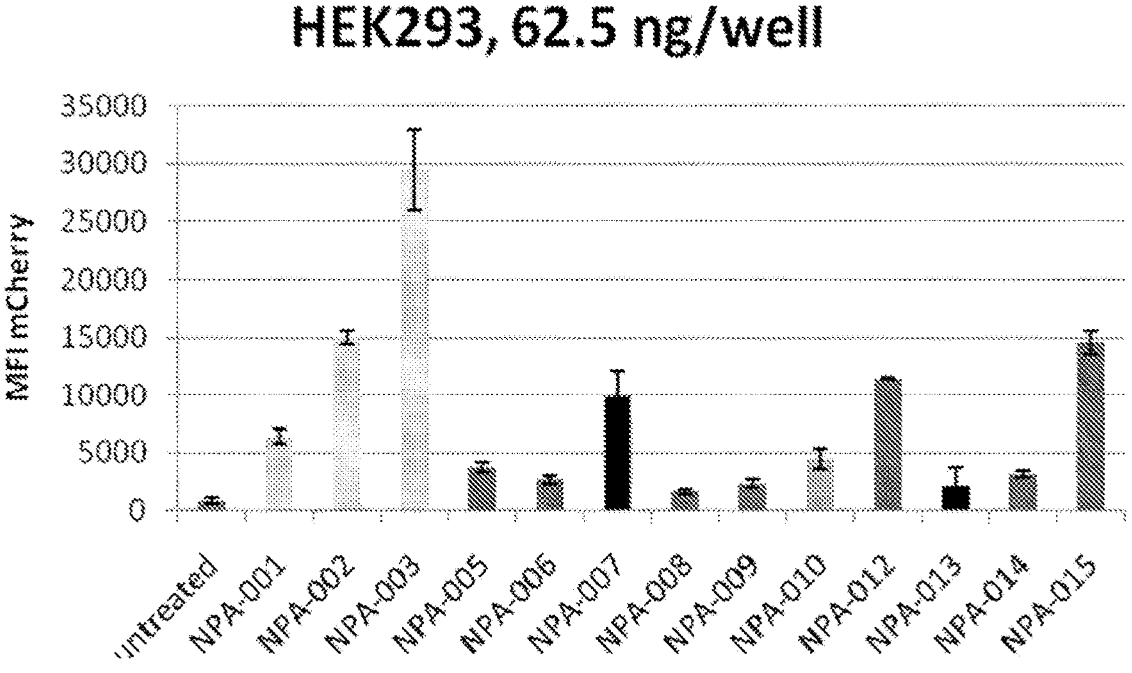
Figure 6C:
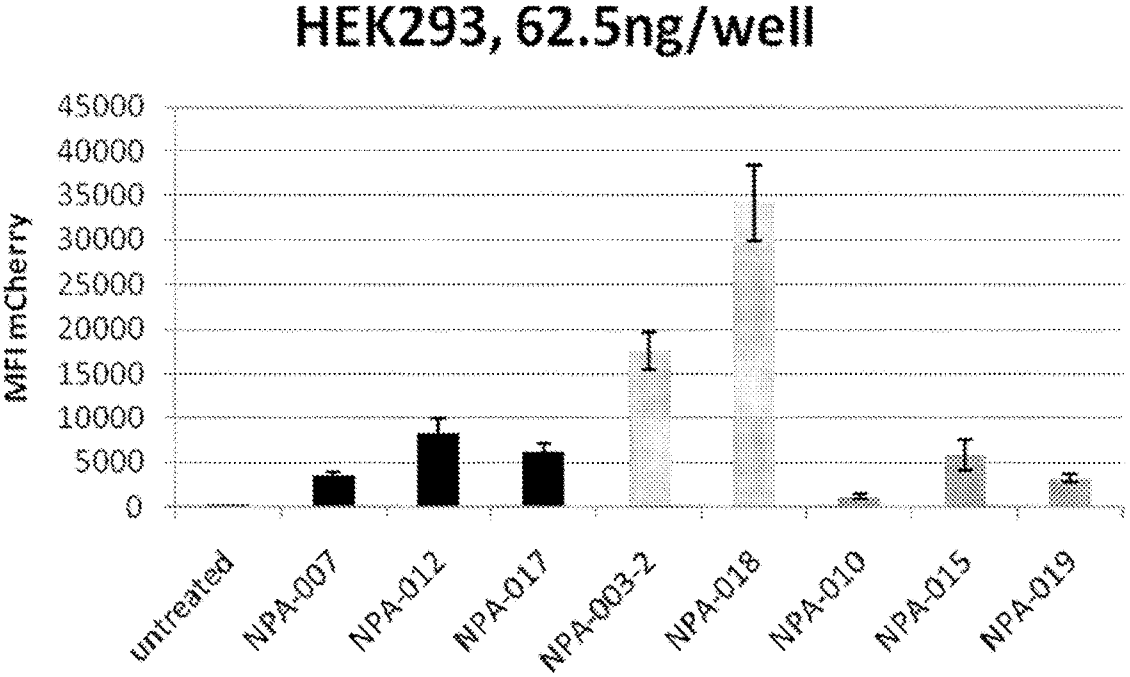
Figure 6D:
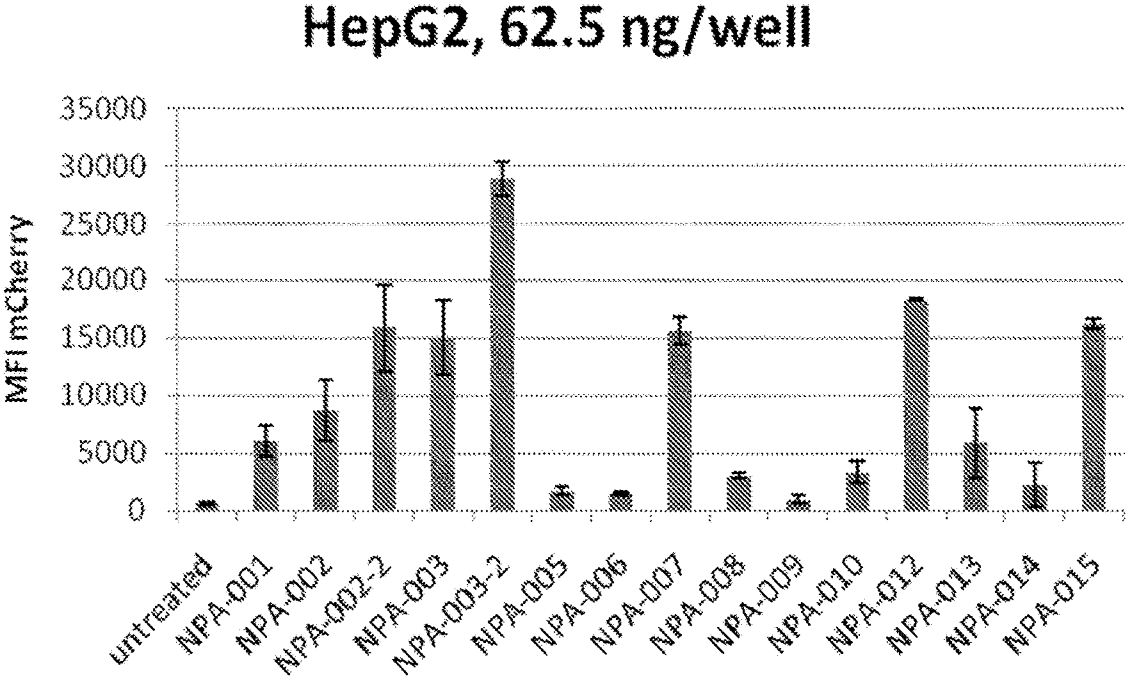
Figure 6E:
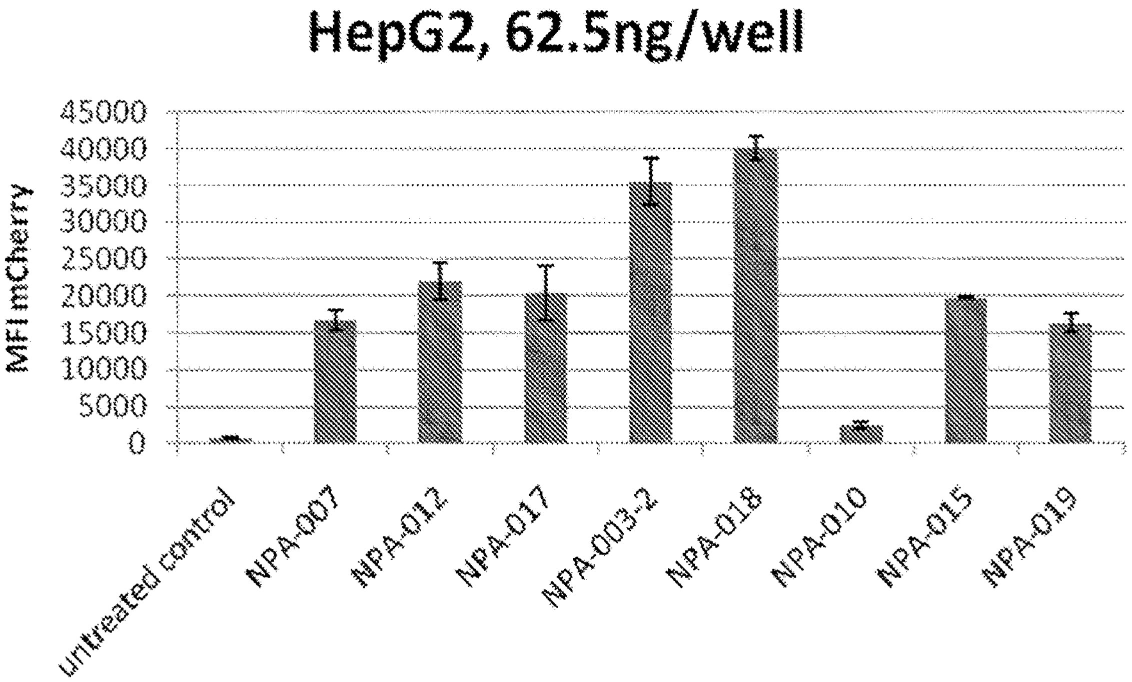

Formulations of DLin-DMA, DLin-K-DMA, DLin-KC2-DMA, 98N12-5, C12-200 and DLin-MC3-DMA were incubated at a concentration of 60 ng/well or 62.5 ng/well in a plate of HEK293 and 62.5 ng/well in a plate of HepG2 cells for 24 hours to determine the MFI of mCherry (mRNA shown in SEQ ID NO: 5; poly-A tail of approximately 160 nucleotides not shown in sequence; 5' cap, Cap 1) for each formulation. The formulations tested are outlined in Table 6 below. As shown in FIG. 6A for the 60 ng/well and FIGS. 6B, 6C, 6D, and 6E for the 62.5 ng/well, the formulation of NPA-003 and NPA-018 have the highest mCherry MFI and the formulations of NPA-008, NPA-010 and NPA-013 are most the similar to the background sample mCherry MFI value.

TABLE 6

| Formulations | | | |
|---|---|---|---|
| Formulation # | Lipid | Lipid/RNA wt/wt | Mean size (nm) |
| NPA-001 | DLin-KC2-DMA | 10 | 155 nm<br>PDI: 0.08 |
| NPA-002 | DLin-KC2-DMA | 15 | 140 nm<br>PDI: 0.11 |
| NPA-002-2 | DLin-KC2-DMA | 15 | 105 nm<br>PDI: 0.04 |
| NPA-003 | DLin-KC2-DMA | 20 | 114 nm<br>PDI: 0.08 |
| NPA-003-2 | DLin-KC2-DMA | 20 | 95 nm<br>PDI: 0.02 |
| NPA-005 | 98N12-5 | 15 | 127 nm<br>PDI: 0.12 |
| NPA-006 | 98N12-5 | 20 | 126 nm<br>PDI: 0.08 |
| NPA-007 | DLin-DMA | 15 | 148 nm<br>PDI: 0.09 |
| NPA-008 | DLin-K-DMA | 15 | 121 nm<br>PDI: 0.08 |
| NPA-009 | C12-200 | 15 | 138 nm<br>PDI: 0.15 |
| NPA-010 | DLin-MC3-DMA | 15 | 126 nm<br>PDI: 0.09 |
| NPA-012 | DLin-DMA | 20 | 86 nm<br>PDI: 0.08 |
| NPA-013 | DLin-K-DMA | 20 | 104 nm<br>PDI: 0.03 |
| NPA-014 | C12-200 | 20 | 101 nm<br>PDI: 0.06 |
| NPA-015 | DLin-MC3-DMA | 20 | 109 nm<br>PDI: 0.07 |

Example 13. In Vivo Formulation Studies

Mice (n=5) are administered intravenously a single dose of a formulation containing a modified mRNA and a lipid. The modified mRNA administered to the mice is selected from G-CSF (mRNA shown in SEQ ID NO: 4; poly-A tail of approximately 160 nucleotides not shown in sequence; 5' cap, Cap 1), erythropoietin (EPO) (mRNA shown in SEQ ID NO: 7; poly-A tail of approximately 160 nucleotides not shown in sequence; 5' cap, Cap1), Factor IX (mRNA shown in SEQ ID NO: 8; poly-A tail of approximately 160 nucleotides not shown in sequence; 5' cap, Cap 1) or mCherry (mRNA sequence shown in SEQ ID NO: 5; poly-A tail of approximately 160 nucleotides not shown in sequence; 5' cap, Cap1). The erythropoietin cDNA with the T7 promoter, 5'untranslated region (UTR) and 3' UTR used in in vitro transcription (IVT) is given in SEQ ID NO: 9.

Each formulation also contains a lipid which is selected from one of DLin-DMA, DLin-K-DMA, DLin-KC2-DMA, 98N12-5, C12-200 or DLin-MC3-DMA. The mice are injected with 100 ug, 10 μg or 1 μg of the formulated modified mRNA and are sacrificed 8 hours after they are administered the formulation. Serum from the mice administered formulations containing human G-CSF modified mRNA are measured by specific G-CSF ELISA and serum from mice administered human Factor IX modified RNA is analyzed by specific Factor IX ELISA or chromogenic assay. The liver and spleen from the mice administered with mCherry modified mRNA are analyzed by immunohistochemistry (IHC) or fluorescence-activated cell sorting (FACS). As a control, a group of mice are not injected with any formulation and their serum and tissue are collected analyzed by ELISA, FACS and/or IHC.

Example 14. In Vitro and In Vivo Expression

A. A. In Vitro Expression in Human Cells Using Lipidoid Formulations

The ratio of mmRNA to lipidoid used to test for in vitro transfection is tested empirically at different lipidoid: mmRNA ratios. Previous work using siRNA and lipidoids have utilized 2.5:1, 5:1, 10:1, and 15:1 lipidoid:siRNA wt:wt ratios. Given the longer length of mmRNA relative to siRNA, a lower wt:wt ratio of lipidoid to mmRNA may be effective. In addition, for comparison mmRNA were also formulated using RNAIMAX™ (Invitrogen, Carlsbad, CA) or TRANSIT-mRNA (Mirus Bio, Madison, WI) cationic lipid delivery vehicles. The ability of lipidoid-formulated Luciferase (IVT cDNA sequence as shown in SEQ ID NO: 10), green fluorescent protein (GFP) (IVT cDNA sequence as shown in SEQ ID NO: 11), G-CSF (mRNA sequence shown in SEQ ID NO: 4; poly-A tail of approximately 160 nucleotides not shown in sequence; 5' cap, Cap 1), and EPO mmRNA (mRNA sequence shown in SEQ ID NO: 7; poly-A tail of approximately 160 nucleotides not shown in sequence; 5' cap, Cap1) to express the desired protein product can be confirmed by luminescence for luciferase expression, flow cytometry for GFP expression, and by ELISA for G-CSF and Erythropoietin (EPO) secretion.

B. In Vivo Expression Following Intravenous Injection

Systemic intravenous administration of the formulations are created using various different lipidoids including, but not limited to, 98N12-5, C12-200, and MD1.

Lipidoid formulations containing mmRNA are injected intravenously into animals. The expression of the modified mRNA (mmRNA)-encoded proteins are assessed in blood and/or other organs samples such as, but not limited to, the liver and spleen collected from the animal. Conducting single dose intravenous studies will also allow an assessment of the magnitude, dose responsiveness, and longevity of expression of the desired product.

In one embodiment, lipidoid based formulations of 98N12-5, C12-200, MD1 and other lipidoids, are used to deliver luciferase, green fluorescent protein (GFP), mCherry fluorescent protein, secreted alkaline phosphatase (sAP), human G-CSF, human Factor IX, or human Erythropoietin (EPO) mmRNA into the animal. After formulating mmRNA with a lipid, as described previously, animals are divided into groups to receive either a saline formulation, or a lipidoid-formulation which contains one of a different mmRNA selected from luciferase, GFP, mCherry, sAP, human G-CSF, human Factor IX, and human EPO. Prior to injection into the animal, mmRNA-containing lipidoid formulations are diluted in PBS. Animals are then administered a single dose of formulated mmRNA ranging from a dose of 10 mg/kg to doses as low as 1 ng/kg, with a preferred range to be 10 mg/kg to 100 ng/kg, where the dose of mmRNA depends on the animal body weight such as a 20 gram mouse receiving a maximum formulation of 0.2 ml (dosing is based no mmRNA per kg body weight). After the administration of the mmRNA-lipidoid formulation, serum, tissues, and/or tissue lysates are obtained and the level of the mmRNA-encoded product is determined at a single and/or a range of time intervals. The ability of lipidoid-formulated Luciferase, GFP, mCherry, sAP, G-CSF, Factor IX, and EPO mmRNA to express the desired protein product is confirmed by luminescence for the expression of Luciferase, flow cytometry for the expression of GFP and mCherry expression, by enzymatic activity for sAP, or by ELISA for the section of G-CSF, Factor IX and/or EPO.

Further studies for a multi-dose regimen are also performed to determine the maximal expression of mmRNA, to evaluate the saturability of the mmRNA-driven expression (by giving a control and active mmRNA formulation in parallel or in sequence), and to determine the feasibility of repeat drug administration (by giving mmRNA in doses separated by weeks or months and then determining whether expression level is affected by factors such as immunogenicity). An assessment of the physiological function of proteins such as G-CSF and EPO are also determined through analyzing samples from the animal tested and detecting increases in granulocyte and red blood cell counts, respectively. Activity of an expressed protein product such as Factor IX, in animals can also be assessed through analysis of Factor IX enzymatic activity (such as an activated partial thromboplastin time assay) and effect of clotting times.

C. In Vitro Expression Following Intramuscular and/or Subcutaneous Injection

The use of lipidoid formulations to deliver oligonucleotides, including mRNA, via an intramuscular route or a subcutaneous route of injection needs to be evaluated as it has not been previously reported. Intramuscular and/or subcutaneous injection of mmRNA are evaluated to determine if mmRNA-containing lipidoid formulations are capable to produce both localized and systemic expression of a desired portions.

Lipidoid formulations of 98N12-5, C12-200, and MD1 containing mmRNA selected from luciferase, green fluorescent protein (GFP), mCherry fluorescent protein, secreted alkaline phosphatase (sAP), human G-CSF, human factor IX, or human Erythropoietin (EPO) mmRNA are injected intramuscularly and/or subcutaneously into animals. The expression of mmRNA-encoded proteins are assessed both within the muscle or subcutaneous tissue and systemically in blood and other organs such as the liver and spleen. Single dose studies allow an assessment of the magnitude, dose responsiveness, and longevity of expression of the desired product.

Animals are divided into groups to receive either a saline formulation or a formulation containing modified mRNA. Prior to injection mmRNA-containing lipidoid formulations are diluted in PBS. Animals are administered a single intramuscular dose of formulated mmRNA ranging from 50 mg/kg to doses as low as 1 ng/kg with a preferred range to be 10 mg/kg to 100 ng/kg. A maximum dose for intramuscular administration, for a mouse, is roughly 1 mg mmRNA or as low as 0.02 ng mmRNA for an intramuscular injection into the hind limb of the mouse. For subcutaneous administration, the animals are administered a single subcutaneous dose of formulated mmRNA ranging from 400 mg/kg to doses as low as 1 ng/kg with a preferred range to be 80 mg/kg to 100 ng/kg. A maximum dose for subcutaneous administration, for a mouse, is roughly 8 mg mmRNA or as low as 0.02 ng mmRNA.

For a 20 gram mouse the volume of a single intramuscular injection is maximally 0.025 ml and a single subcutaneous injection is maximally 0.2 ml. The optimal dose of mmRNA administered is calculated from the body weight of the animal. At various points in time points following the administration of the mmRNA-lipidoid, serum, tissues, and tissue lysates is obtained and the level of the mmRNA-encoded product is determined. The ability of lipidoid-formulated luciferase, green fluorescent protein (GFP), mCherry fluorescent protein, secreted alkaline phosphatase (sAP), human G-CSF, human factor IX, or human Erythropoietin (EPO) mmRNA to express the desired protein product is confirmed by luminescence for luciferase expression, flow cytometry for GFP and mCherry expression, by enzymatic activity for sAP, and by ELISA for G-CSF, Factor IX and Erythropoietin (EPO) secretion.

Additional studies for a multi-dose regimen are also performed to determine the maximal expression using mmRNA, to evaluate the saturability of the mmRNA-driven expression (achieved by giving a control and active mmRNA formulation in parallel or in sequence), and to determine the feasibility of repeat drug administration (by giving mmRNA in doses separated by weeks or months and then determining whether expression level is affected by factors such as immunogenicity). Studies utilizing multiple subcutaneous or intramuscular injection sites at one time point, are also utilized to further increase mmRNA drug exposure and improve protein production. An assessment of the physiological function of proteins, such as GFP, mCherry, sAP, human G-CSF, human factor IX, and human EPO, are determined through analyzing samples from the tested animals and detecting a change in granulocyte and/or red blood cell counts. Activity of an expressed protein product such as Factor IX, in animals can also be assessed through analysis of Factor IX enzymatic activity (such as an activated partial thromboplastin time assay) and effect of clotting times.

Example 15. Split Dose Studies

Studies utilizing multiple subcutaneous or intramuscular injection sites at one time point were designed and performed to investigate ways to increase mmRNA drug exposure and improve protein production. In addition to detection of the expressed protein product, an assessment of the physiological function of proteins was also determined through analyzing samples from the animal tested.

Surprisingly, it has been determined that split dosing of mmRNA produces greater protein production and phenotypic responses than those produced by single unit dosing or multi-dosing schemes.

The design of a single unit dose, multi-dose and split dose experiment involved using human erythropoietin (EPO) mmRNA (mRNA sequence shown in SEQ ID NO: 7; poly-A tail of approximately 160 nucleotides not shown in sequence; 5' cap, Cap 1) administered in buffer alone. The dosing vehicle (F. buffer) consisted of 150 mM NaCl, 2 mM $CaCl_2$, 2 mM $Na^+$-phosphate (1.4 mM monobasic sodium phosphate; 0.6 mM dibasic sodium phosphate), and 0.5 mM EDTA, pH 6.5. The pH was adjusted using sodium hydroxide and the final solution was filter sterilized. The mmRNA was modified with 5meC at each cytosine and pseudouridine replacement at each uridine site.

Animals (n=5) were injected IM (intramuscular) for the single unit dose of 100 ug. For multi-dosing, two schedules were used, 3 doses of 100 μg and 6 doses of 100 ug. For the split dosing scheme, two schedules were used, 3 doses at 33.3 ug and 6 doses of 16.5 ug mmRNA. Control dosing involved use of buffer only at 6 doses. Control mmRNA involved the use of luciferase mmRNA (IVT cDNA sequence shown in SEQ ID NO: 10) dosed 6 times at 100 ug. Blood and muscle tissue were evaluated 13 hrs post injection.

Human EPO protein was measured in mouse serum 13 h post I.M. single, multi- or split dosing of the EPO mmRNA in buffer. Seven groups of mice (n=5 mice per group) were treated and evaluated. The results are shown in Table 7.

TABLE 7

Split dose study

| Group | Treatment | Dose of mmRNA | Total Dose | Avg. pmol/mL human EPO | Polypeptide per unit drug (pmol/ug) | Dose Splitting Factor |
|---|---|---|---|---|---|---|
| 1 | Human EPO mmRNA | 1 × 100 ug | 100 ug | 14.3 | .14 | 1 |
| 2 | Human EPO mmRNA | 3 × 100 ug | 300 ug | 82.5 | .28 | 2 |
| 3 | Human EPO mmRNA | 6 × 100 ug | 600 ug | 273.0 | .46 | 3.3 |
| 4 | Human EPO mmRNA | 3 × 33.3 ug | 100 ug | 104.7 | 1.1 | 7.9 |
| 5 | Human EPO mmRNA | 6 × 16.5 ug | 100 ug | 127.9 | 1.3 | 9.3 |
| 6 | Luciferase mmRNA | 6 × 100 ug | 600 ug | 0 | — | — |
| 7 | Buffer Alone | — | — | 0 | — | — |

The splitting factor is defined as the product per unit drug divided by the single dose product per unit drug (PUD). For example for treatment group 2 the value 0.28 or product (EPO) per unit drug (mmRNA) is divided by the single dose product per unit drug of 0.14. The result is 2. Likewise, for treatment group 4, the value 1.1 or product (EPO) per unit drug (mmRNA) is divided by the single dose product per unit drug of 0.14. The result is 7.9. Consequently, the dose splitting factor (DSF) may be used as an indicator of the efficacy of a split dose regimen. For any single administration of a total daily dose, the DSF should be equal to 1. Therefore any DSF greater than this value in a split dose regimen is an indication of increased efficacy.

To determine the dose response trends, impact of injection site and impact of injection timing, studies are performed. In these studies, varied doses of 1 ug, 5 ug, 10 ug, 25 ug, 50 ug, and values in between are used to determine dose response outcomes. Split dosing for a 100 ug total dose includes three or six doses of 1.6 ug, 4.2 ug, 8.3 ug, 16.6 ug, or values and total doses equal to administration of the total dose selected.

Injection sites are chosen from the limbs or any body surface presenting enough area suitable for injection. This may also include a selection of injection depth to target the dermis (Intradermal), epidermis (Epidermal), subcutaneous tissue (SC) or muscle (IM). Injection angle will vary based on targeted delivery site with injections targeting the intradermal site to be 10-15 degree angles from the plane of the surface of the skin, between 20-45 degrees from the plane of the surface of the skin for subcutaneous injections and angles of between 60-90 degrees for injections substantially into the muscle.

Example 16: Dose Response and Injection Site Selection and Timing

To determine the dose response trends, impact of injection site and impact of injection timing, studies are performed following the protocol outlined in Example 15. In these studies, varied doses of 1 ug, 5 ug, 10 ug, 25 ug, 50 ug, and values in between are used to determine dose response outcomes. Split dosing for a 100 ug total dose includes three or six doses of 1.6 ug, 4.2 ug, 8.3 ug, 16.6 ug, or values and total doses equal to administration of the total dose selected.

Injection sites are chosen from the limbs or any body surface presenting enough area suitable for injection. This may also include a selection of injection depth to target the dermis (Intradermal), epidermis (Epidermal), subcutaneous tissue (SC) or muscle (IM). Injection angle will vary based on targeted delivery site with injections targeting the intradermal site to be 10-15 degree angles from the plane of the surface of the skin, between 20-45 degrees from the plane of the surface of the skin for subcutaneous injections and angles of between 60-90 degrees for injections substantially into the muscle. RNAIMAX™

Example 17. Routes of Administration

Figure 7A:
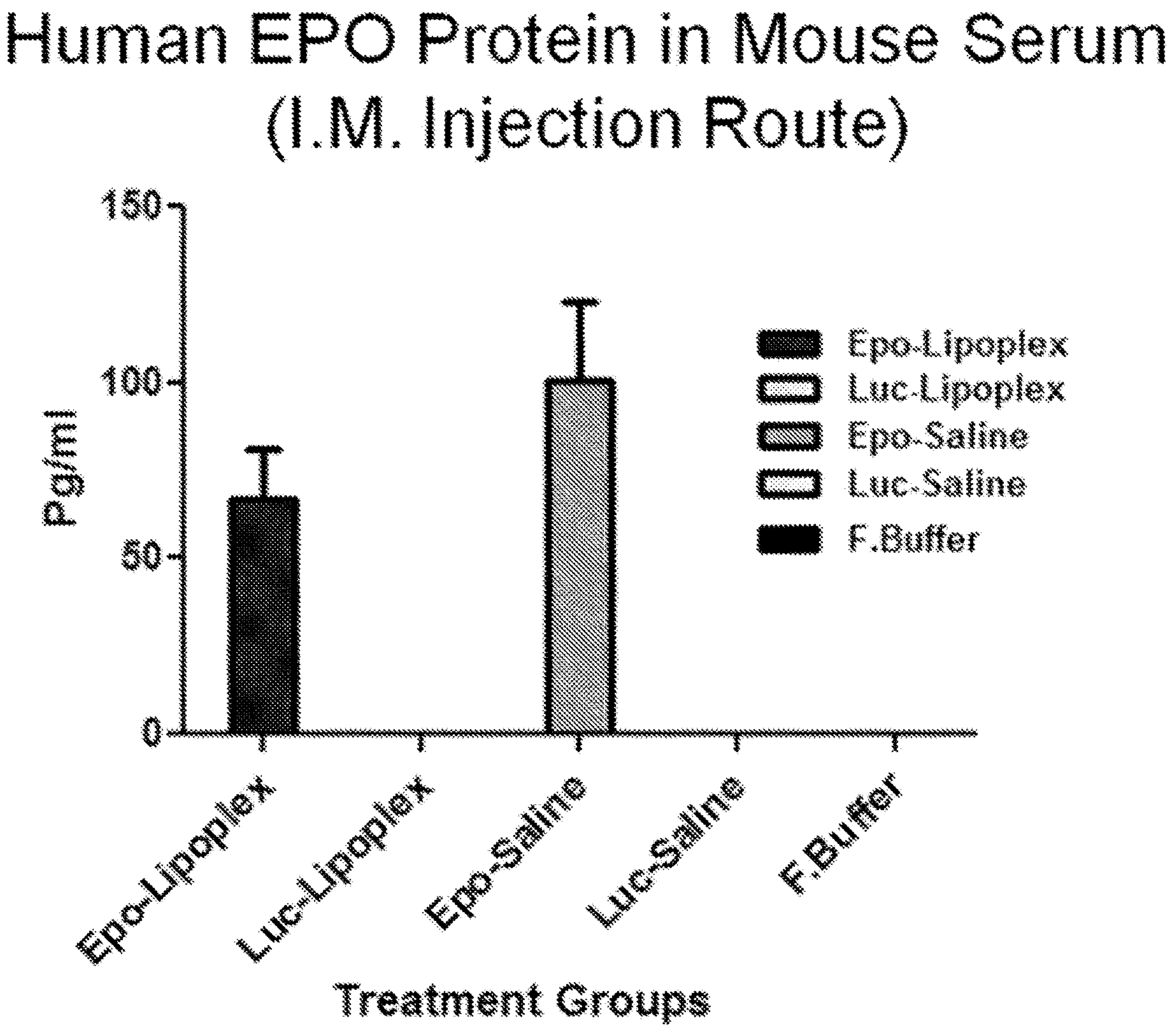
FIGS. 7A and 7B are histograms showing in vivo screening results of human erythropoietin in serum after the administration of modified human erythropoietin mmRNA or luciferase mmRNA in mice.
Figure 7B:
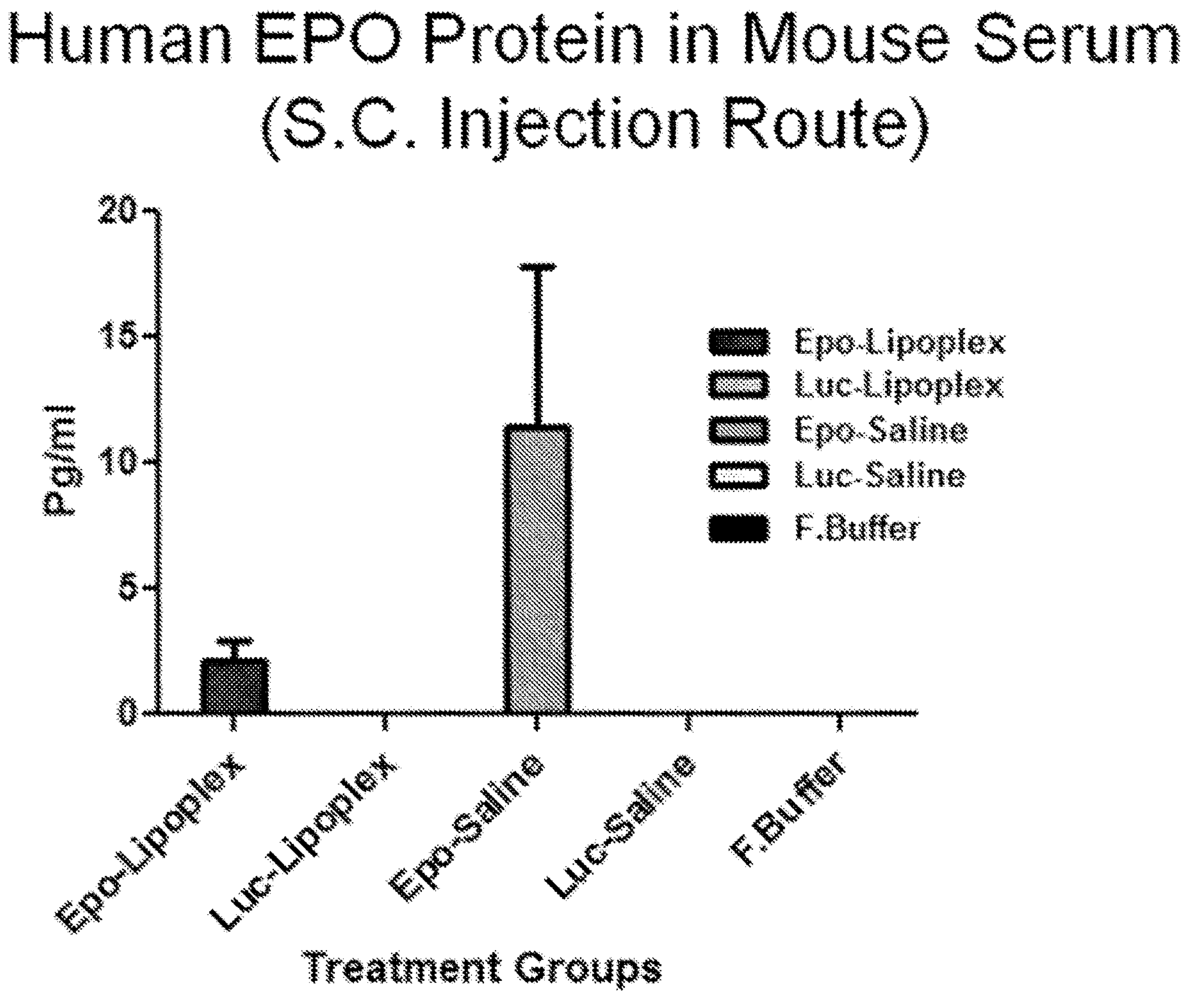

Further studies were performed to investigate dosing using different routes of administration. Following the protocol outlined in Example 15, 4 mice per group were dosed intramuscularly (I.M.), intravenously (IV) or subcutaneously (S.C.) by the dosing chart outlined in Table 8. Serum was collected 13 hours post injection from all mice, tissue was collected from the site of injection from the intramuscular and subcutaneous group and the spleen, liver and kidneys were collected from the intravenous group. The results from the intramuscular group are show in FIG. 7A and the subcutaneous group results are shown in FIG. 7B.

TABLE 8

Dosing Chart

| Group | Treatment | Route | Dose of mmRNA | Total Dose | Dosing Vehicle |
|---|---|---|---|---|---|
| 1 | Lipoplex-human EPO mmRNA | I.M. | 4 × 100 ug + 30% Lipoplex | 4 × 70 ul | Lipoplex |
| 2 | Lipoplex-human EPO mmRNA | I.M. | 4 × 100 ug | 4 × 70 ul | Buffer |
| 3 | Lipoplex-human EPO mmRNA | S.C. | 4 × 100 ug + 30% Lipoplex | 4 × 70 ul | Lipoplex |
| 4 | Lipoplex-human EPO mmRNA | S.C. | 4 × 100 ug | 4 × 70 ul | Buffer |
| 5 | Lipoplex-human EPO mmRNA | I.V. | 200 ug + 30% Lipoplex | 140 ul | Lipoplex |
| 6 | Lipoplexed-Luciferase mmRNA | I.M. | 100 ug + 30% Lipoplex | 4 × 70 ul | Lipoplex |
| 7 | Lipoplexed-Luciferase mmRNA | I.M. | 100 ug | 4 × 70 ul | Buffer |
| 8 | Lipoplexed-Luciferase mmRNA | S.C. | 100 ug + 30% Lipoplex | 4 × 70 ul | Lipoplex |
| 9 | Lipoplexed-Luciferase mmRNA | S.C. | 100 ug | 4 × 70 ul | Buffer |
| 10 | Lipoplexed-human EPO mmRNA | I.V. | 200 ug + 30% Lipoplex | 140 ul | Lipoplex |
| 11 | Formulation Buffer | I.M. | 4 × multi dosing | 4 × 70 ul | Buffer |

Example 18: In Vivo Delivery of Modified mRNA

Modified RNA was delivered to C57/BL6 mice intramuscularly, subcutaneously, or intravenously to evaluate the bio-distribution of modified RNA using luciferase. A formulation buffer used with all delivery methods contained 150 mM sodium chloride, 2 mM calcium chloride, 2 mM Na+-phosphate which included 1.4 mM monobasic sodium phosphate and 0.6 mM of dibasic sodium phosphate, and 0.5 mM ethylenediaminetetraacetic acid (EDTA) was adjusted using sodium hydroxide to reach a final pH of 6.5 before being filtered and sterilized. A 1× concentration was used as the delivery buffer. To create the lipoplexed solution delivered to the mice, in one vial 50 μg of RNA was equilibrated for 10 minutes at room temperature in the delivery buffer and in a second vial 10 μl RNAiMAX™ was equilibrated for 10 minutes at room temperature in the delivery buffer. After equilibrium, the vials were combined and delivery buffer was added to reach a final volume of 100 μl which was then incubated for 20 minutes at room temperature. Luciferin was administered by intraperitoneal injection (IP) at 150 mg/kg to each mouse prior to imaging during the plateau phase of the luciferin exposure curve which was between 15 and 30 minutes. To create luciferin, 1 g of D-luciferin potassium or sodium salt was dissolved in 66.6 ml of distilled phosphate buffer solution (DPBS), not containing Mg2+ or Ca2+, to make a 15 mg/ml solution. The solution was gently mixed and passed through a 0.2 μm syringe filter, before being purged with nitrogen, aliquoted and frozen at −80° C. while being protected from light as much as possible. The solution was thawed using a waterbath if luciferin was not dissolved, gently mixed and kept on ice on the day of dosing.

Whole body images were taken of each mouse 2, 8 and 24 hours after dosing. Tissue images and serum was collected from each mouse 24 hours after dosing. Mice administered doses intravenously had their liver, spleen, kidneys, lungs, heart, peri-renal adipose tissue and thymus imaged. Mice administered doses intramuscularly or subcutaneously had their liver, spleen, kidneys, lungs, peri-renal adipose tissue, and muscle at the injection site. From the whole body images the bioluminescence was measured in photon per second for each route of administration and dosing regimen.

A. Intramuscular Administration

Figure 8A:
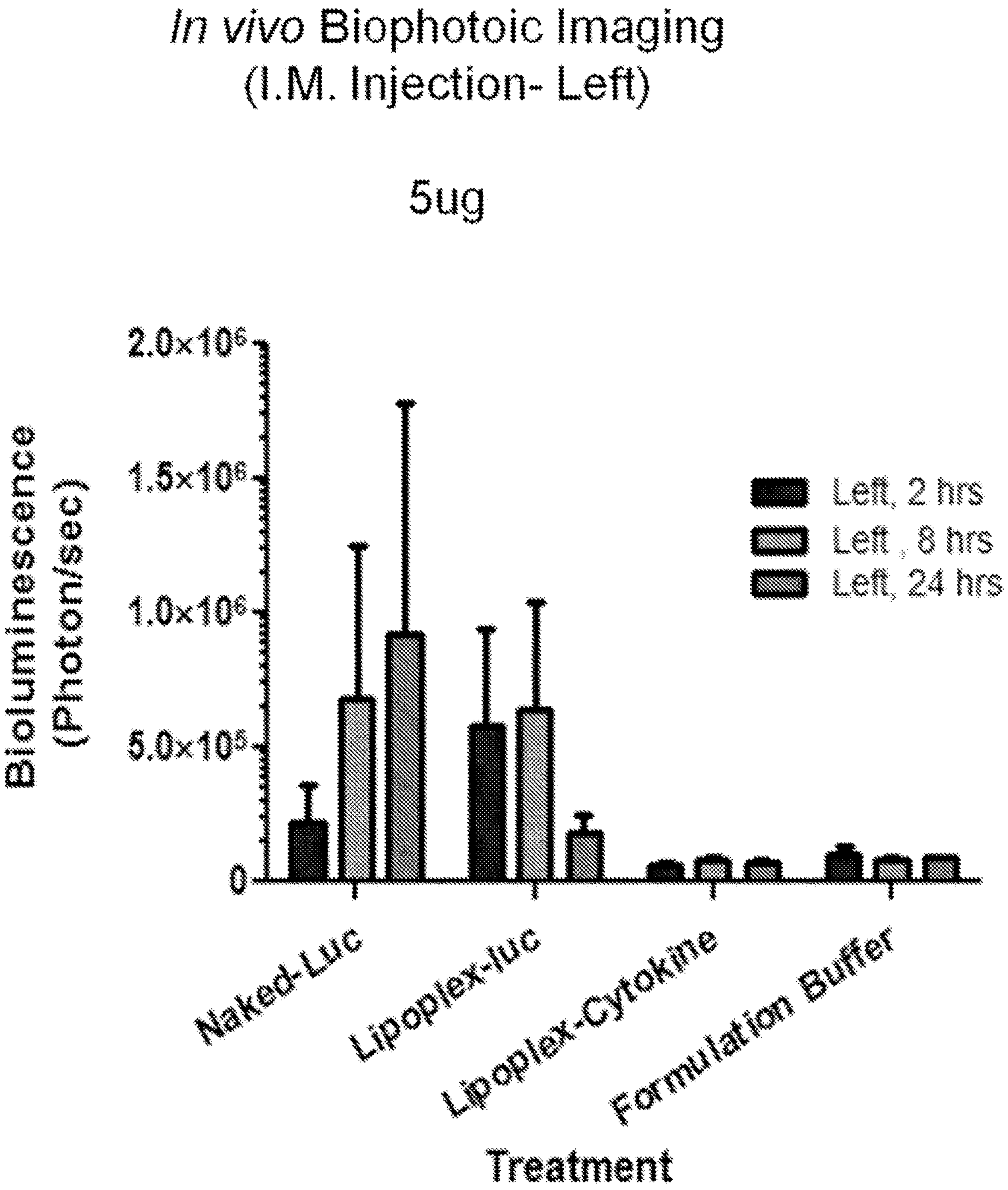
FIGS. 8A, 8B, 8C, and 8D are histograms of in vivo screening results from biophotoic imaging.
Figure 8B:
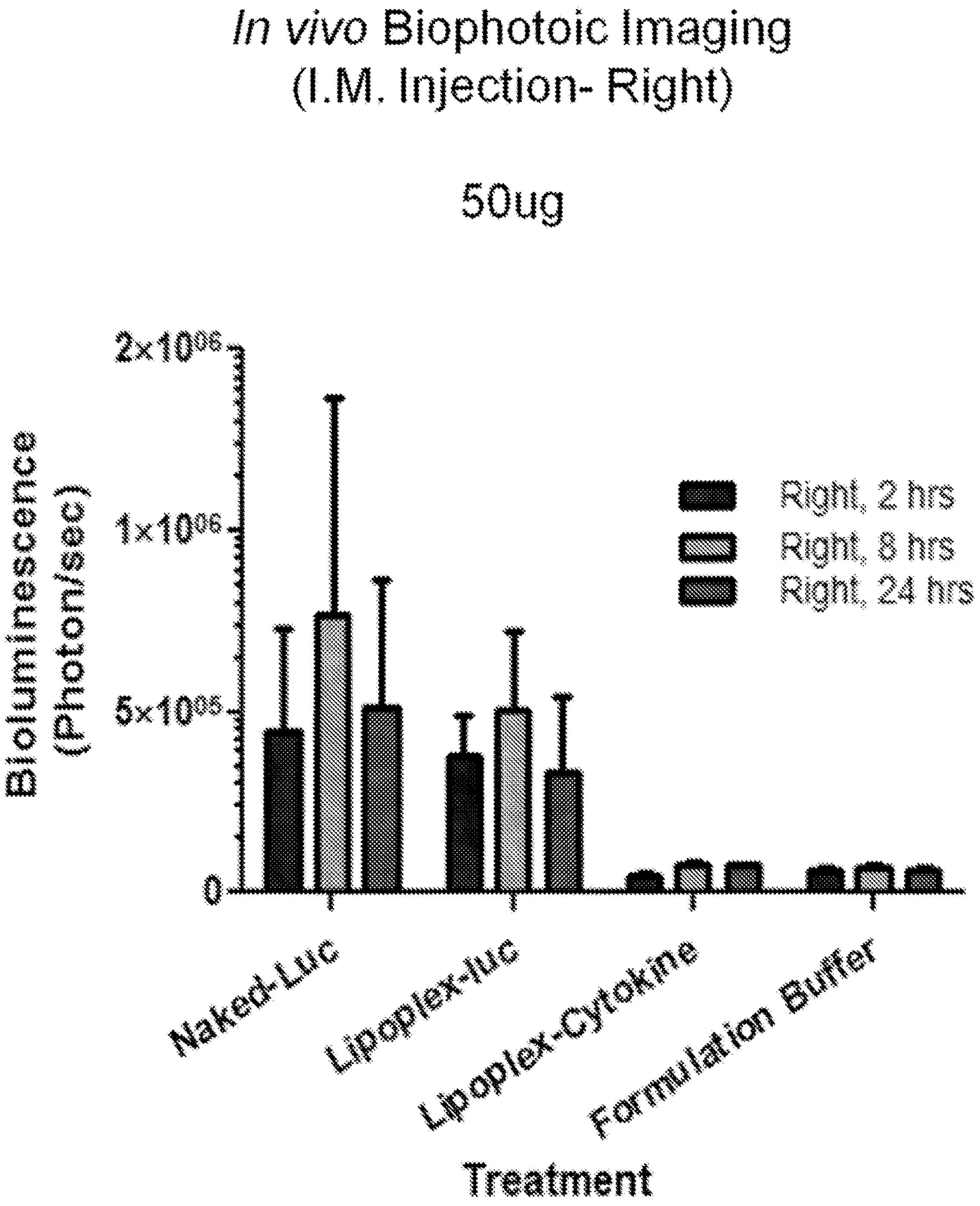

Mice were intramuscularly (I.M.) administered either modified luciferase mRNA (IVT cDNA sequence shown in SEQ ID NO: 10) (Naked-Luc), lipoplexed modified luciferase mRNA (Lipoplex-luc), lipoplexed modified granulocyte colony-stimulating factor (G-CSF) mRNA (mRNA sequence shown in SEQ ID NO: 4; poly-A tail of approximately 160 nucleotides not shown in sequence; 5' cap, Cap 1) (Lipoplex-Cytokine) or the formation buffer at a single dose of 50 μg of modified RNA in an injection volume of 50 μl for each formulation in the right hind limb and a single dose of 5 μg of modified RNA in an injection volume of 50 μl in the left hind limb. The bioluminescence average for the luciferase expression signals for each group at 2, 8 and 24 hours after dosing are shown in FIG. 8A for the left hind limb and FIG. 8B for the right hind limb. The bioluminescence showed a positive signal at the injection site of the 5 μg and 50 μg modified RNA formulations containing and not containing lipoplex.

B. Subcutaneous Administration

Figure 8C:
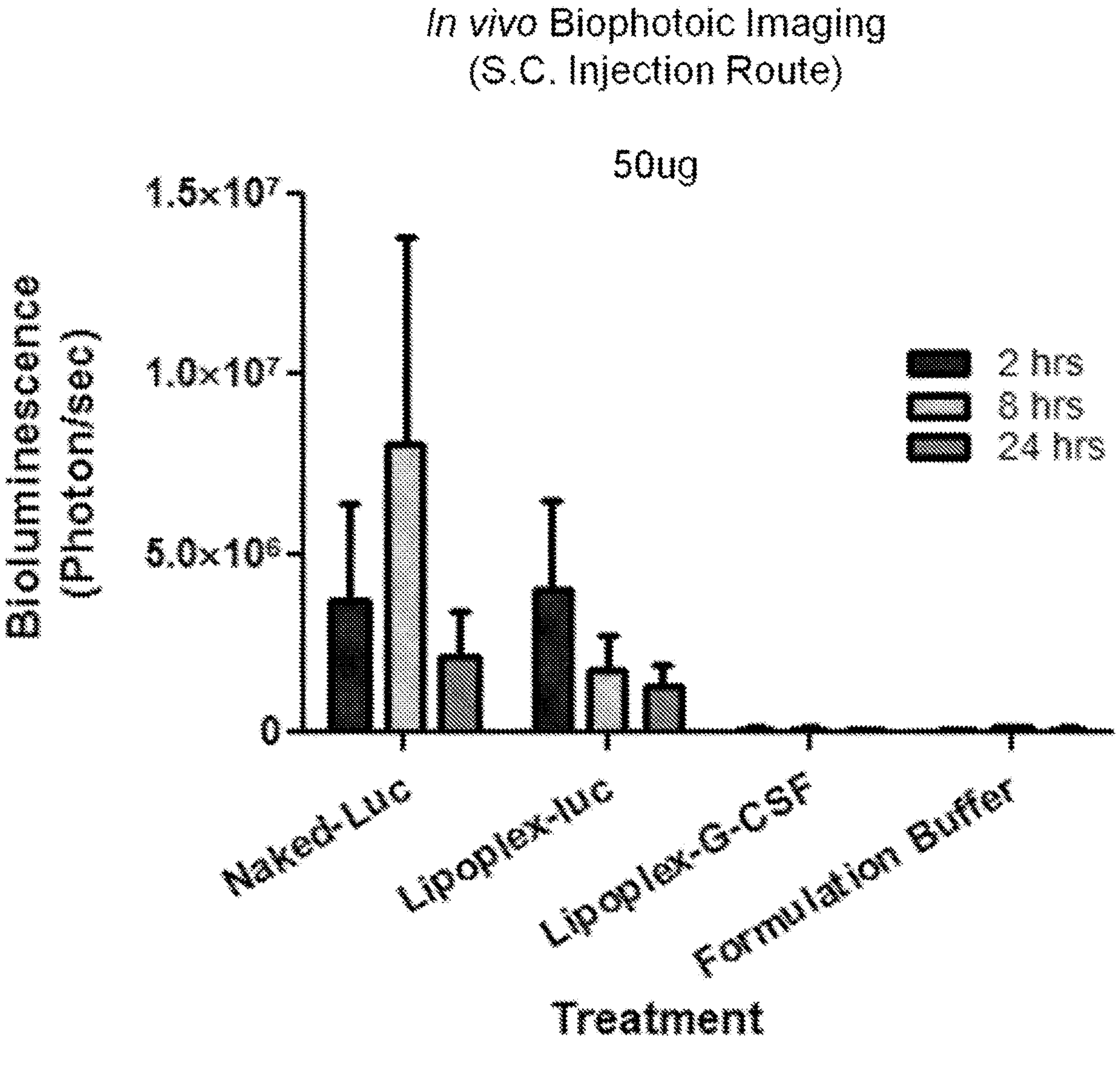

Mice were subcutaneously (S.C.) administered either modified luciferase mRNA (Naked-Luc), lipoplexed modified luciferase mRNA (Lipoplex-luc), lipoplexed modified G-CSF mRNA (Lipoplex-G-CSF) or the formation buffer at a single dose of 50 μg of modified mRNA in an injection volume of 100 μl for each formulation. The bioluminescence average for the luciferase expression signals for each group at 2, 8 and 24 hours after dosing are shown in FIG. 8C. The bioluminescence showed a positive signal at the injection site of the 50 μg modified mRNA formulations containing and not containing lipoplex.

C. Intravenous Administration

Figure 8D:
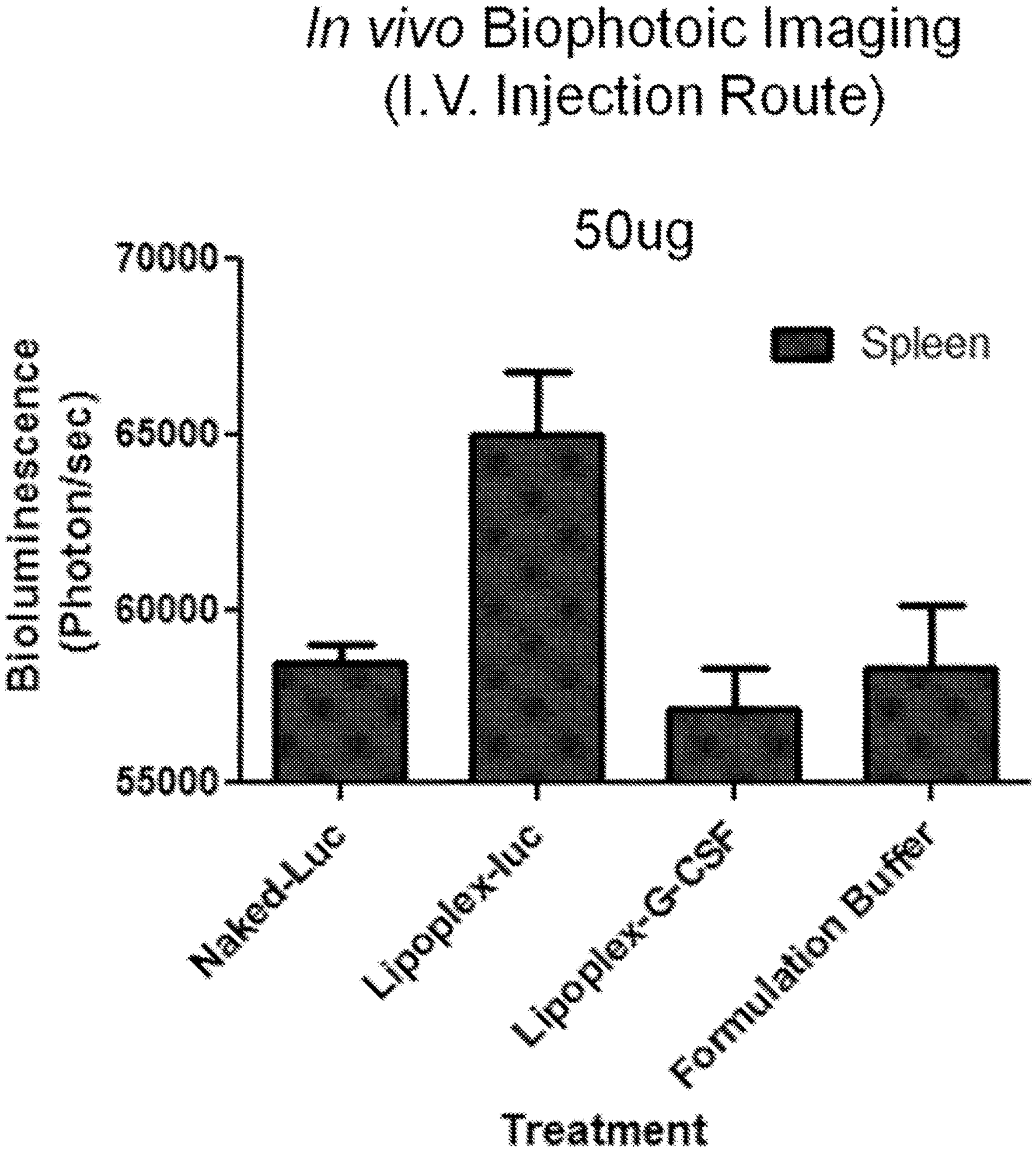

Mice were intravenously (I.V.) administered either modified luciferase mRNA (Naked-Luc), lipoplexed modified luciferase mRNA (Lipoplex-luc), lipoplexed modified G-CSF mRNA (Lipoplex-G-CSF) or the formation buffer at a single dose of 50 μg of modified mRNA in an injection volume of 100 μl for each formulation. The bioluminescence average for the luciferase expression signal in the spleen from each group at 2 hours after dosing is shown in FIG. 8D. The bioluminescence showed a positive signal in the spleen of the 50 μg modified mRNA formulations containing lipoplex.

Example 19: In Vivo Delivery Using Lipoplexes

A. Human EPO Modified RNA Lipoplex

Figure 9:
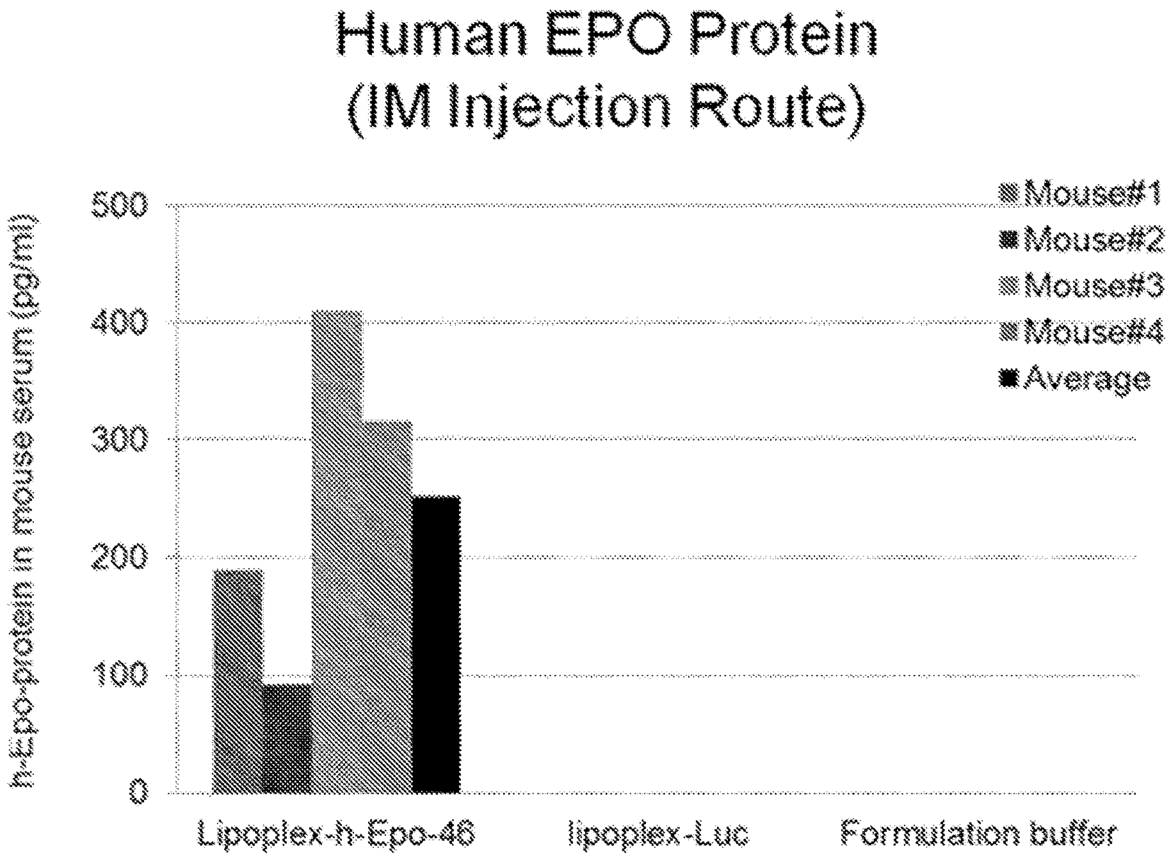
FIG. 9 is a histogram showing in vivo screening results for modified human G-CSF mmRNA administered intramuscularly, subcutaneously or intravenously in mice.

A formulation containing 100 μg of modified human erythropoietin mRNA (mRNA sequence shown in SEQ ID NO: 7; poly-A tail of approximately 160 nucleotides not shown in sequence; 5' cap, Cap1) (EPO; fully modified 5-methylcytosine; N1-methylpseudouridine) was lipoplexed with 30% by volume of RNAIMAX™ (Lipoplex-h-Epo-46; Generation 2 or Gen2) in 50-70 uL delivered intramuscularly to four C57/BL6 mice. Other groups consisted of mice receiving an injection of the lipoplexed modified luciferase mRNA (Lipoplex-luc) (IVT cDNA sequence shown in SEQ ID NO: 10) which served as a control containing 100 μg of modified luciferase mRNA was lipoplexed with 30% by volume of RNAIMAX™ or mice receiving an injection of the formulation buffer as negative control at a dose volume of 65 ul. 13 hours after the intramuscular injection, serum was collected from each mouse to measure the amount of human EPO protein in the mouse serum by human EPO ELISA and the results are shown in FIG. 9.

B. Human G-CSF Modified RNA Lipoplex

Figure 10:
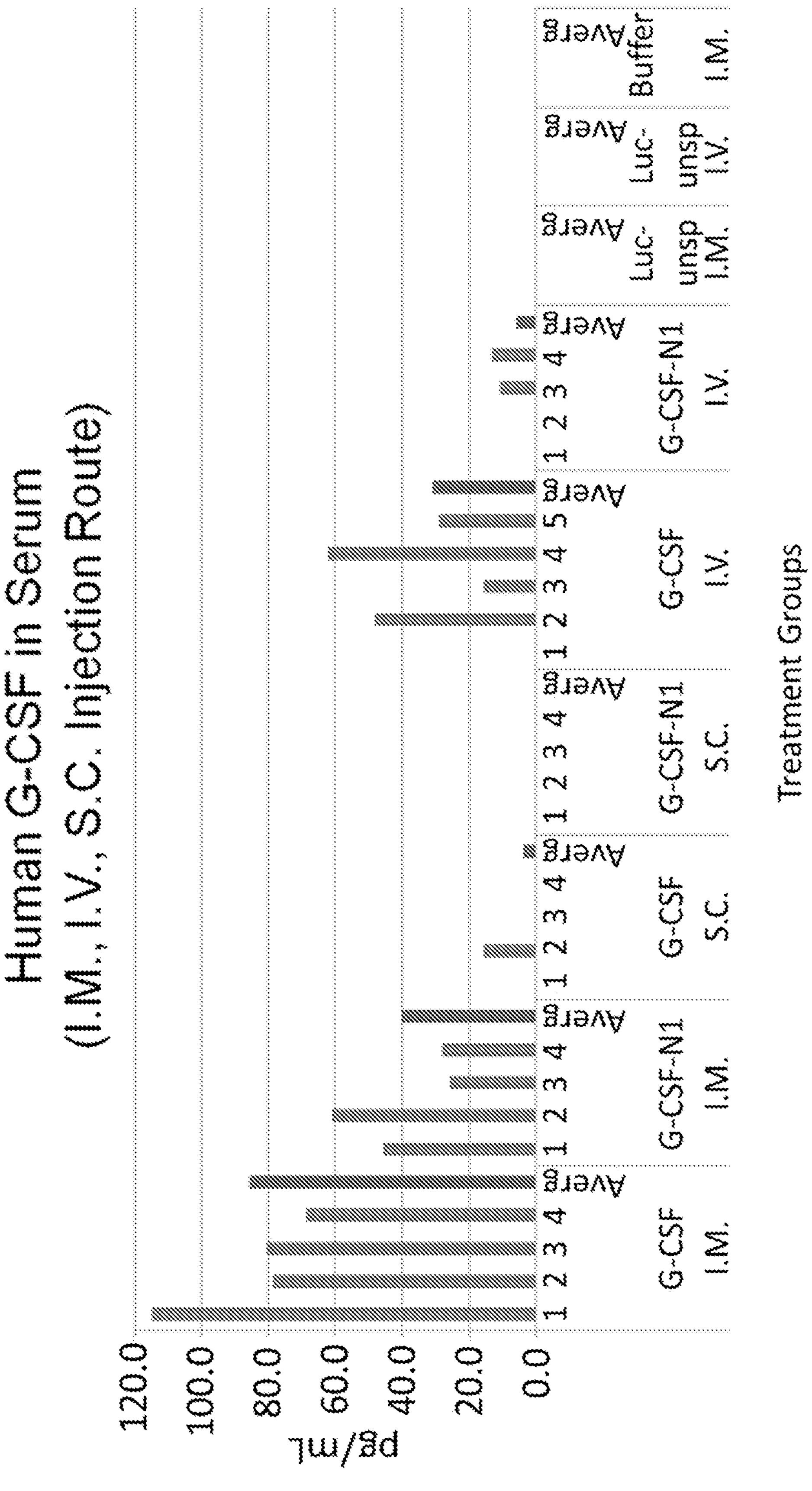
FIG. 10 is a histogram showing in vivo screening results for modified G-CSF administered intramuscularly, subcutaneously or intravenously.

A formulation containing 100 μg of one of the two types of modified human G-CSF mRNA (mRNA sequence shown in SEQ ID NO: 4; poly-A tail of approximately 160 nucleotides not shown in sequence; 5' cap, Cap1) (G-CSF fully modified with 5-methylcytosine and pseudouridine (G-CSF) or G-CSF fully modified with 5-methylcytosine and N1-methyl-pseudouridine (G-CSF-N1) lipoplexed with 30% by volume of RNAIMAX™ and delivered in 150 uL intramuscularly (I.M), in 150 uL subcutaneously (S.C) and in 225 uL intravenously (I.V) to C57/BL6 mice. Three control groups were administered either 100 μg of modified luciferase mRNA (IVT cDNA sequence shown in SEQ ID NO: 10) intramuscularly (Luc-unsp I.M.) or 150 μg of modified luciferase mRNA intravenously (Luc-unsp I.V.) or 150 μL of the formulation buffer intramuscularly (Buffer I.M.). 6 hours after administration of a formulation, serum was collected from each mouse to measure the amount of human G-CSF protein in the mouse serum by human G-CSF ELISA and the results are shown in FIG. 10.

C. Human G-CSF Modified RNA Lipoplex Comparison

Figure 11A:
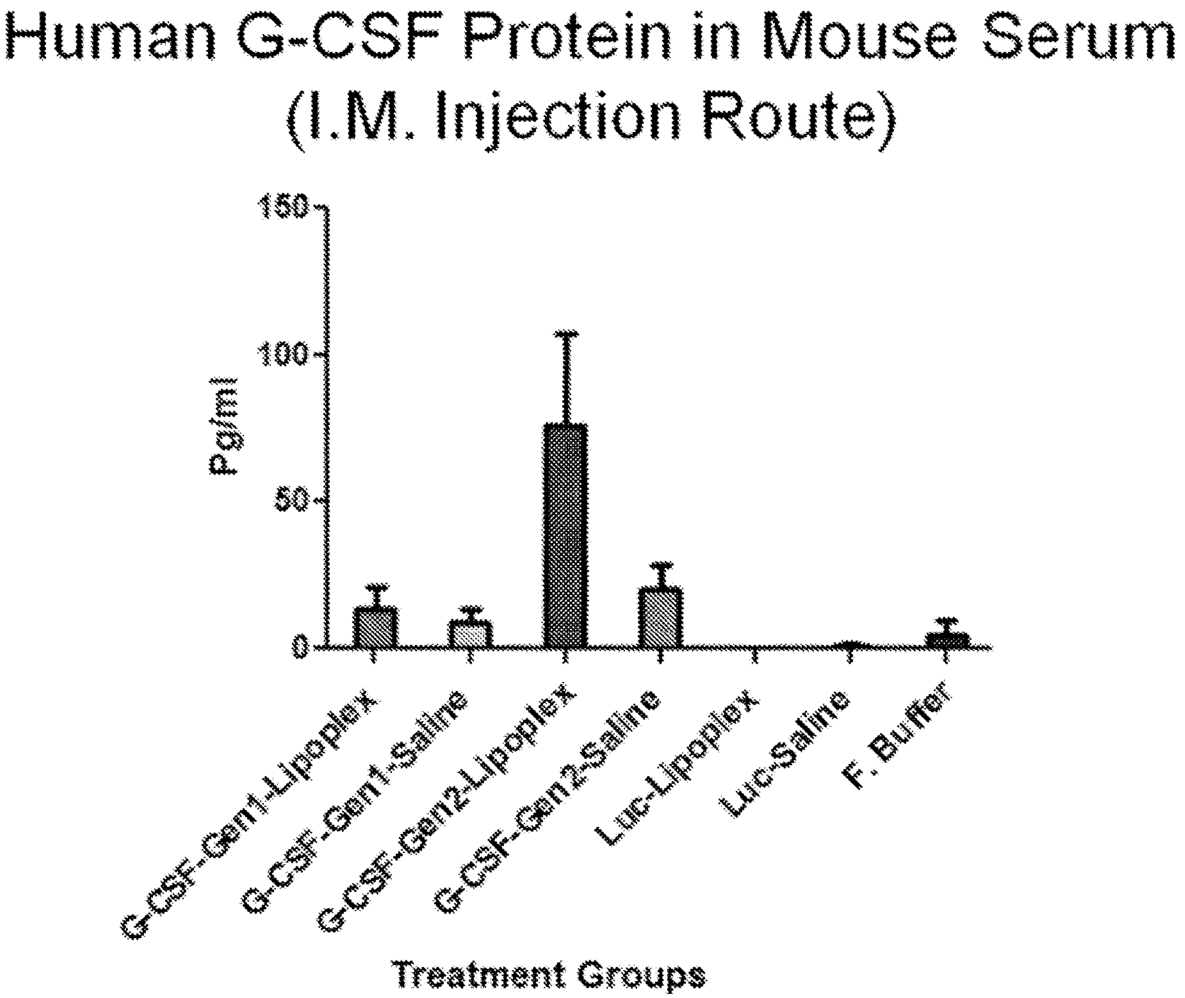
FIGS. 11A and 11B are histograms showing in vivo screening results of modified human G-CSF mmRNA administered intramuscularly or subcutaneously in mice.
Figure 11B:
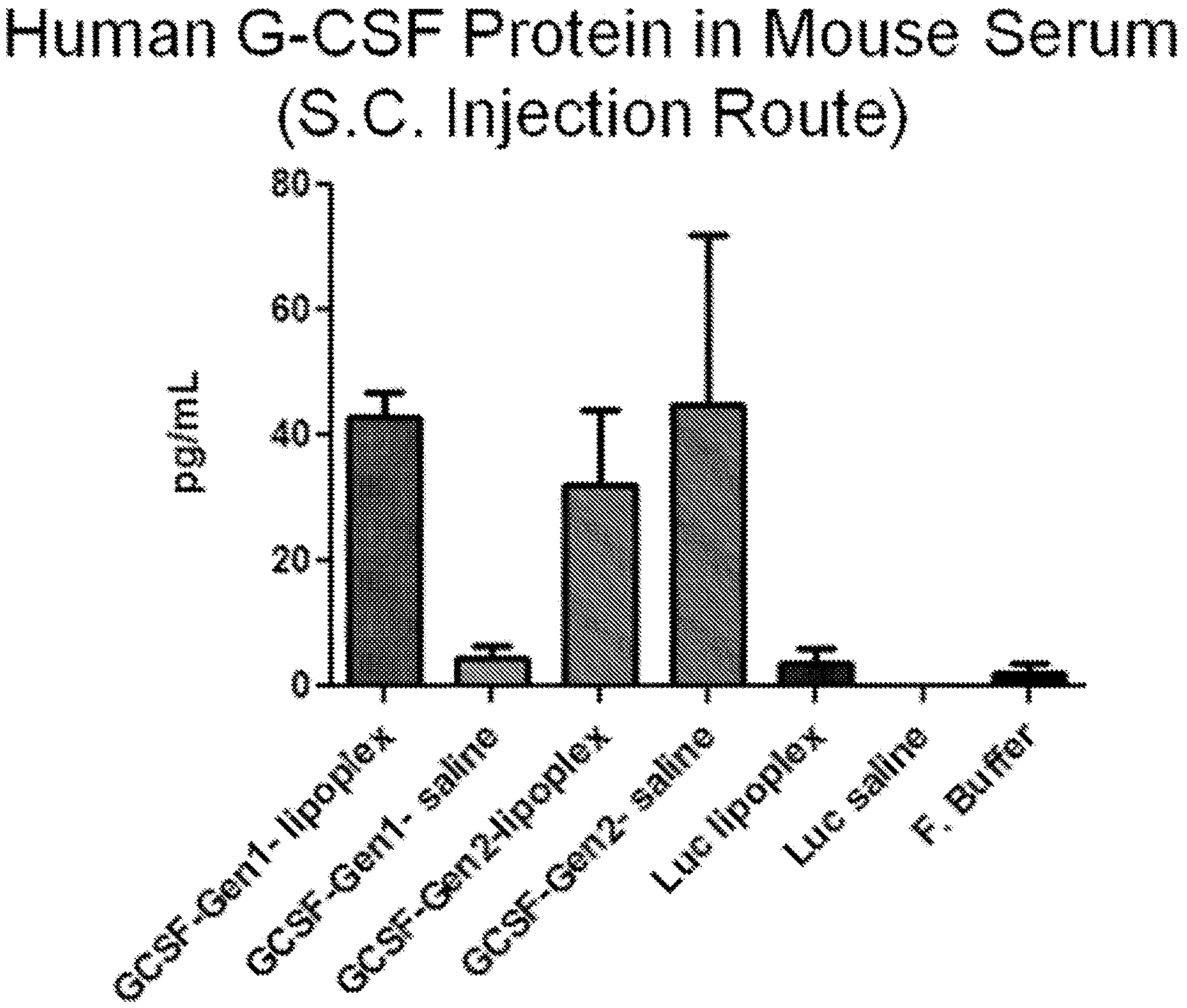

A formulation containing 100 μg of either modified human G-CSF mRNA lipoplexed with 30% by volume of RNAIMAX™ with a 5-methylcytosine (5mc) and a pseudouridine (Ψ) modification (G-CSF-Gen1-Lipoplex), modified human G-CSF mRNA with a 5mc and Ψ modification in saline (G-CSF-Gen1-Saline), modified human G-CSF mRNA with a N1-5-methylcytosine (N1-5mc) and a Ψ modification lipoplexed with 30% by volume of RNAIMAX™ (G-CSF-Gen2-Lipoplex), modified human G-CSF mRNA with a N1-5mc and Ψ modification in saline (G-CSF-Gen2-Saline), modified luciferase with a 5mc and Ψ modification lipoplexed with 30% by volume of RNAIMAX™ (Luc-Lipoplex), or modified luciferase mRNA with a a 5mc and Ψ modification in saline (Luc-Saline) was delivered intramuscularly (I.M.) or subcutaneously (S.C.) and a control group for each method of administration was giving a dose of 80 μL of the formulation buffer (F. Buffer) to C57/BL6 mice. 13 hours post injection serum and tissue from the site of injection were collected from each mouse and analyzed by G-CSF ELISA to compare human G-CSF protein levels. The results of the human G-CSF protein in mouse serum from the intramuscular administration are shown in FIG. 11A, and the subcutaneous administration results are shown in FIG. 11B.

D. mCherry Modified RNA Lipoplex Comparison

Intramuscular and Subcutaneous Administration

A formulation containing 100 μg of either modified mCherry mRNA (mRNA sequence shown in SEQ ID NO: 5; poly-A tail of approximately 160 nucleotides not shown in sequence; 5' cap, Cap 1) lipoplexed with 30% by volume of RNAIMAX™ or modified mCherry mRNA in saline is delivered intramuscularly and subcutaneously to mice. A formulation buffer is also administered to a control group of mice either intramuscularly or subcutaneously. The site of injection on the mice may be collected 17 hours post injection for sectioning to determine the cell type(s) responsible for producing protein.

Intravitreal Administration

A formulation containing 10 μg of either modified mCherry mRNA lipoplexed with RNAIMAX™, modified mCherry mRNA in a formulation buffer, modified luciferase mRNA lipoplexed with RNAMAX™, modified luciferase mRNA in a formulation buffer can be administered by intravitreal injection (IVT) in rats in a dose volume of 5 μl/eye. A formulation buffer is also administered by IVT to a control group of rats in a dose volume of 5 μl/eye. Eyes from treated rats can be collected after 18 hours post injection for sectioning and lysating to determine whether mmRNA can be effectively delivered in vivo to the eye and result in protein production, and to also determine the cell type(s) responsible for producing protein in vivo.

Intranasal Administration

A formulation containing 100 μg of either modified mCherry mRNA lipoplexed with 30% by volume of RNAIMAX™, modified mCherry mRNA in saline, modified luciferase mRNA lipoplexed with 30% by volume of RNAIMAX™ or modified luciferase mRNA in saline is delivered intranasally. A formulation buffer is also administered to a control group intranasally. Lungs may be collected about 13 hours post instillation for sectioning (for those receiving mCherry mRNA) or homogenization (for those receiving luciferase mRNA). These samples will be used to determine whether mmRNA can be effectively delivered in vivo to the lungs and result in protein production, and to also determine the cell type(s) responsible for producing protein in vivo.

Example 20: In Vivo Delivery Using Varying Lipid Ratios

Figure 12:
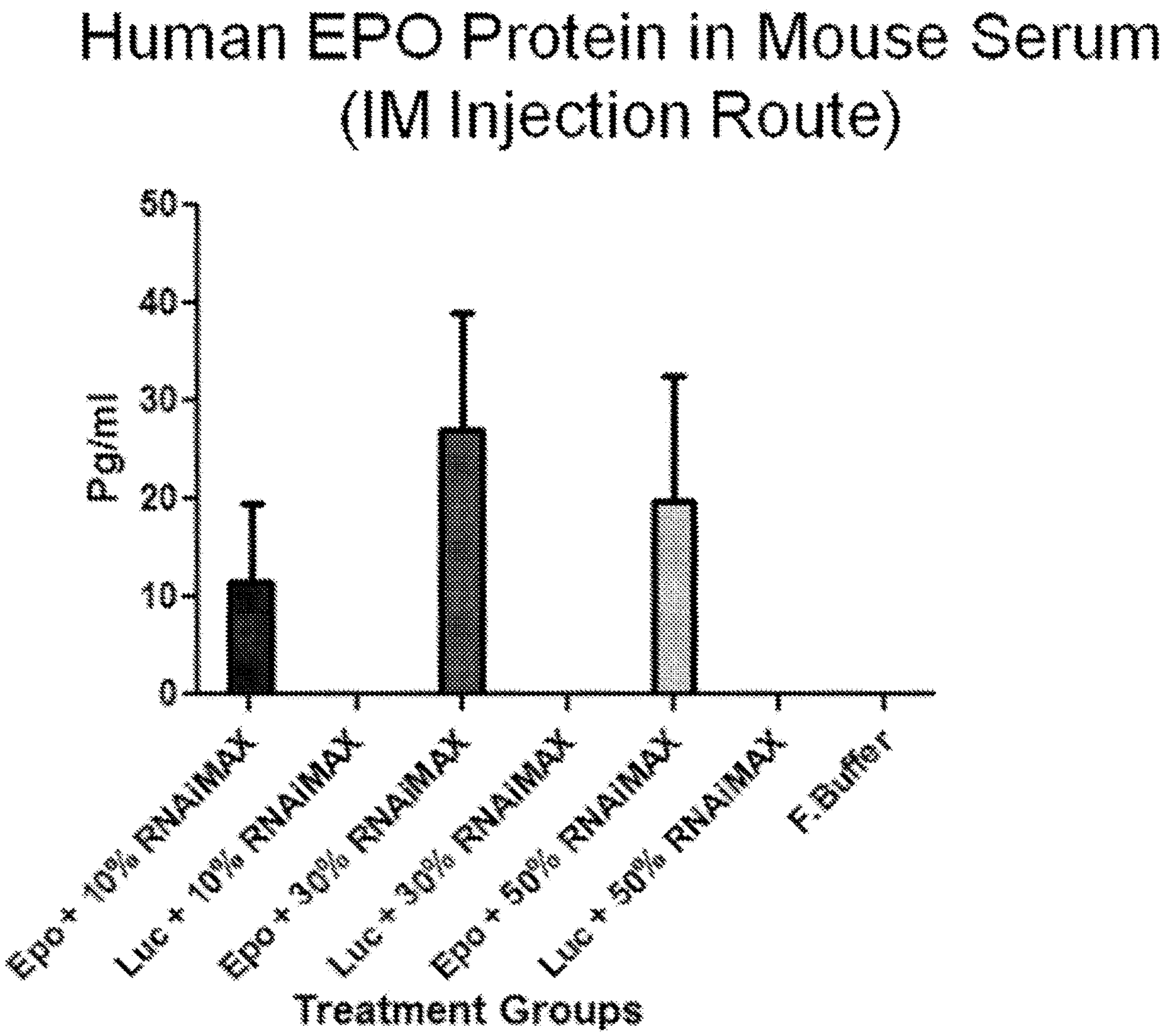
FIG. 12 is a histogram showing in vivo screening results of human erythropoietin in serum after the administration of modified human erythropoietin mmRNA or luciferase mmRNA administered intramuscularly in mice.

Modified mRNA was delivered to C57/BL6 mice to evaluate varying lipid ratios and the resulting protein expression. Formulations of 100 μg modified human EPO mRNA (mRNA sequence shown in SEQ ID NO: 7; poly-A tail of approximately 160 nucleotides not shown in sequence; 5' cap, Cap 1) lipoplexed with 10%, 30% or 50% RNAIMAX™, 100 μg modified luciferase mRNA (IVT cDNA sequence shown in SEQ ID NO: 10) lipoplexed with 10%, 30% or 50% RNAIMAX™ or a formulation buffer were administered intramuscularly to mice in a single 70 μl dose. Serum was collected 13 hours post injection to undergo a human EPO ELISA to determine the human EPO protein level in each mouse. The results of the human EPO ELISA, shown in FIG. 12, show that modified human EPO expressed in the muscle is secreted into the serum for each of the different percentage of RNAIMAX™

Example 21: Intramuscular and Subcutaneous In Vivo Delivery in Mammals

Modified human EPO mRNA (mRNA sequence shown in SEQ ID NO: 7; poly-A tail of approximately 160 nucleotides not shown in sequence; 5' cap, Cap1) formulated in saline was delivered to either C57/BL6 mice or Sprague-Dawley rats to evaluate the dose dependency on human EPO production. Rats were intramuscularly injected with 50 al of the modified human EPO mRNA (h-EPO), modified luciferase mRNA (Luc) (IVT cDNA sequence shown in SEQ ID NO: 10) or the formulation buffer (F.Buffer) as described in the dosing chart Table 9.

Mice were intramuscularly or subcutaneously injected with 50 al of the modified human EPO mRNA (h-EPO), modified luciferase mRNA (Luc) or the formulation buffer (F.Buffer) as described in the dosing chart Table 10. 13 hours post injection blood was collected and serum was analyzed to determine the amount human EPO for each mouse or rat. The average and geometric mean in pg/ml for the rat study are also shown in Table 9.

TABLE 9

| Rat Study | | | | | | | | | | | |
|---|---|---|---|---|---|---|---|---|---|---|---|
| | Group | Dose | R#1 | R#2 | R#3 | R#4 | R#5 | R#6 | Avg. pg/ml | Geometric-mean pg/ml |
| h-EPO | G#1 | 150 μg | 61.8 | 86.3 | 69.9 | 55.2 | 59 | 74.2 | 67.7 | 67.1 |
| h-EPO | G#2 | 100 μg | 69.4 | 77.8 | 48.2 | 17.6 | 101.9 | 161.5 | 79.4 | 66.9 |
| h-EPO | G#3 | 50 μg | 143.6 | 60.9 | 173.4 | 145.9 | 61.5 | 23.9 | 101.5 | 85.4 |
| h-EPO | G#4 | 10 μg | 7.8 | 11.8 | 30.9 | 36.2 | 40.6 | 150.3 | 46.3 | 31.2 |
| h-EPO | G#5 | 1 μg | 9.1 | 35.8 | — | 46.2 | 18.1 | 34.1 | 28.7 | 25.4 |
| Luc | G#6 | 100 μg | 34.1 | 36.5 | 13.5 | 13.7 | — | — | 24.5 | 22.4 |
| F. Buffer | G#7 | — | 14.7 | 18.5 | 21.2 | 20.3 | — | — | 18.7 | 18.5 |

TABLE 10

| Mouse Study | | | | |
|---|---|---|---|---|
| Route | Treatment | Group | Dose | Average Level in serum pg/ml |
| IM | h-EPO | 1 | 100 μg | 96.2 |
| IM | h-EPO | 2 | 50 μg | 63.5 |
| IM | h-EPO | 3 | 25 μg | 18.7 |
| IM | h-EPO | 4 | 10 μg | 25.9 |
| IM | h-EPO | 5 | 1 μg | 2.6 |
| IM | Luc | 6 | 100 μg | 0 |
| IM | F. Buffer | 7 | — | 1.0 |
| SC | h-EPO | 1 | 100 μg | 72.0 |
| SC | Luc | 2 | 100 μg | 26.7 |
| SC | F. Buffer | 3 | — | 17.4 |

Example 22: Duration of Activity after Intramuscular In Vivo Delivery in Rats Modified human EPO mRNA (mRNA sequence shown in SEQ ID NO: 7; poly-A tail of approximately 160 nucleotides not shown in sequence; 5' cap, Cap1) formulated in saline was delivered to Sprague-Dawley rats to determine the duration of the dose response. Rats were intramuscularly injected with 50 al of the modified human EPO mRNA (h-EPO), modified luciferase mRNA (IVT cDNA sequence shown in SEQ ID NO: 10) (Luc) or the formulation buffer (F.Buffer) as described in the dosing chart Table 11. The rats were bled 2, 6, 12, 24, 48 and 72 hours after the intramuscular injection to determine the concentration of human EPO in serum at a given time. The average and geometric mean in pg/ml for this study are also shown in Table 11.

TABLE 11

| Dosing Chart | | | | | | | | | | | |
|---|---|---|---|---|---|---|---|---|---|---|---|
| | Group | Dose | R#1 | R#2 | R#3 | R#4 | R#5 | R#6 | R#7 | Avg. pg/ml | Geometric-mean pg/ml |
| h-EPO | 2 hour | 100 μg | 60.0 | 62.4 | 53.6 | 33.2 | 68.6 | 66.4 | 72.8 | 59.6 | 58.2 |
| h-EPO | 6 hour | 100 μg | 66.4 | 102.5 | 45.6 | 78.1 | 56.8 | 122.5 | 8.1 | 68.6 | 55.8 |
| h-EPO | 12 hour | 100 μg | 132.9 | 55.1 | 89.0 | 80.1 | 85.6 | 105.6 | 63.3 | 87.4 | 84.5 |
| h-EPO | 24 hour | 100 μg | 51.1 | 76.3 | 264.3 | 142.4 | 77.6 | 73.5 | 75.0 | 108.6 | 95.3 |
| h-EPO | 48 hour | 100 μg | 96.3 | 59.0 | 85.7 | 82.6 | 63.5 | 80.3 | — | 77.9 | 77.0 |
| h-EPO | 72 hour | 100 μg | 46.3 | 66.9 | 73.5 | 57.3 | 136.7 | 110 | 69.7 | 80.1 | 75.8 |
| Luc | 24, 48 and 72 hour | 100 μg | 60.2 | 38.5 | 48.8 | 46.1 | 3.6 | 26.1 | — | 37.2 | 29.2 |
| F. Buffer | 24, 48 and 72 hour | — | 50.0 | 10.0 | 80.9 | 54.7 | — | — | — | 48.9 | 10.4 |

Example 23. In Vitro Transfection of VEGF-A

Human vascular endothelial growth factor-isoform A (VEGF-A) modified mRNA (mRNA sequence shown in SEQ ID NO: 12; poly-A tail of approximately 160 nucleotides not shown in sequence; 5' cap, Cap1) was transfected via reverse transfection in Human Keratinocyte cells in 24 multi-well plates. Human Keratinocytes cells were grown in EPILIFE® medium with Supplement S7 from Invitrogen (Carlsbad, CA) until they reached a confluence of 50-70%. The cells were transfected with 0, 46.875, 93.75, 187.5, 375, 750, and 1500 ng of modified mRNA (mmRNA) encoding VEGF-A which had been complexed with RNAIMAX™ from Invitrogen (Carlsbad, CA). The RNA:RNAIMAX™ complex was formed by first incubating the RNA with Supplement-free EPILIFE® media in a 5× volumetric dilution for 10 minutes at room temperature. In a second vial, RNAIMAX™ reagent was incubated with Supplement-free EPILIFE® Media in a 10× volumetric dilution for 10 minutes at room temperature. The RNA vial was then mixed with the RNAIMAX™ vial and incubated for 20-30 minutes at room temperature before being added to the cells in a drop-wise fashion.

The fully optimized mRNA encoding VEGF-A transfected with the Human Keratinocyte cells included modifications during translation such as natural nucleoside triphosphates (NTP), pseudouridine at each uridine site and 5-methylcytosine at each cytosine site (pseudo-U/5mC), and N1-methyl-pseudouridine at each uridine site and 5-methylcytosine at each cytosine site (N1-methyl-Pseudo-U/5mC). Cells were transfected with the mmRNA encoding VEGF-A and secreted VEGF-A concentration (pg/ml) in the culture medium was measured at 6, 12, 24, and 48 hours post-transfection for each of the concentrations using an ELISA kit from Invitrogen (Carlsbad, CA) following the manufacturers recommended instructions. These data, shown in Table 12, show that modified mRNA encoding VEGF-A is capable of being translated in Human Keratinocyte cells and that VEGF-A is transported out of the cells and released into the extracellular environment.

TABLE 12

| VEGF-A Dosing and Protein Secretion | | | | |
|---|---|---|---|---|
| Dose (ng) | 6 hours (pg/ml) | 12 hours (pg/ml) | 24 hours (pg/ml) | 48 hours (pg/ml) |
| VEGF-A Dose Containing Natural NTPs | | | | |
| 46.875 | 10.37 | 18.07 | 33.90 | 67.02 |
| 93.75 | 9.79 | 20.54 | 41.95 | 65.75 |
| 187.5 | 14.07 | 24.56 | 45.25 | 64.39 |
| 375 | 19.16 | 37.53 | 53.61 | 88.28 |
| 750 | 21.51 | 38.90 | 51.44 | 61.79 |
| 1500 | 36.11 | 61.90 | 76.70 | 86.54 |
| VEGF-A Dose Containing Pseudo-U/5 mC | | | | |
| 46.875 | 10.13 | 16.67 | 33.99 | 72.88 |
| 93.75 | 11.00 | 20.00 | 46.47 | 145.61 |
| 187.5 | 16.04 | 34.07 | 83.00 | 120.77 |
| 375 | 69.15 | 188.10 | 448.50 | 392.44 |
| 750 | 133.95 | 304.30 | 524.02 | 526.58 |
| 1500 | 198.96 | 345.65 | 426.97 | 505.41 |
| VEGF-A Dose Containing N1-methyl-Pseudo-U/5 mC | | | | |
| 46.875 | 0.03 | 6.02 | 27.65 | 100.42 |
| 93.75 | 12.37 | 46.38 | 121.23 | 167.56 |
| 187.5 | 104.55 | 365.71 | 1025.41 | 1056.91 |
| 375 | 605.89 | 1201.23 | 1653.63 | 1889.23 |
| 750 | 445.41 | 1036.45 | 1522.86 | 1954.81 |
| 1500 | 261.61 | 714.68 | 1053.12 | 1513.39 |

Example 24. In Vivo Studies of Factor IX

Human Factor IX mmRNA (mRNA shown in SEQ ID NO: 8; poly-A tail of approximately 160 nucleotides not shown in sequence; 5' cap, Cap1) (Gen1; fully modified 5-methycytosine and pseudouridine) formulated in saline was delivered to mice via intramuscular injection. The results demonstrate that Factor TX protein was elevated in serum as measured 13 hours after administration.

In this study, mice (N=5 for Factor IX, N=3 for Luciferase or Buffer controls) were intramuscularly injected with 50 al of the Factor IX mmRNA (mRNA sequence shown in SEQ ID NO: 8; poly-A tail of approximately 160 nucleotides not shown in sequence; 5' cap, Cap1), Luciferase (cDNA sequence for IVT shown in SEQ ID NO: 10) or the formulation buffer (F.Buffer) at 2×100 ug/mouse. The mice were bled at 13 hours after the intramuscular injection to determine the concentration of human the polypeptide in serum in pg/mL. The results revealed that administration of Factor IX mmRNA resulted in levels of 1600 µg/mL at 13 hours as compared to less than 100 µg/mL of Factor IX for either Luciferase or buffer control administration.

Example 25. Multi-Site Administration: Intramuscular and Subcutaneous

Human G-CSF mmRNA (mRNA sequence shown in SEQ ID NO: 4; poly-A tail of approximately 160 nucleotides not shown in sequence; 5' cap, Cap1) modified as either Gen1 or Gen2 (5-methylcytosine (5mc) and a pseudouridine (W) modification, G-CSF-Gen1; or N1-5-methylcytosine (N1-5mc) and a W modification, G-CSF-Gen2) and formulated in saline were delivered to mice via intramuscular (IM) or subcutaneous (SC) injection. Injection of four doses or 2×50 ug (two sites) daily for three days (24 hrs interval) was performed. The fourth dose was administered 6 hrs before blood collection and CBC analysis. Controls included Luciferase (cDNA sequence for IVT shown in SEQ ID NO: 10) or the formulation buffer (F.Buffer). The mice were bled at 72 hours after the first mmRNA injection (6 hours after the last mmRNA dose) to determine the effect of mmRNA-encoded human G-CSF on the neutrophil count. The dosing regimen is shown in Table 13 as are the resulting neutrophil counts (thousands/uL). Asterisks indicate statistical significance at $p<0.05$.

For intramuscular administration, the data reveal a four fold increase in neutrophil count above control at day 3 for the Gen1 G-CSF mmRNA and a two fold increase for the Gen2 G-CSF mmRNA. For subcutaneous administration, the data reveal a two fold increase in neutrophil count above control at day 3 for the Gen2 G-CSF mmRNA.

TABLE 13

Dosing Regimen

| Gr. | Treatment | Route | N= | Dose (µg/mouse) | Dose Vol. (µl/mouse) | Dosing Vehicle | Neutrophil Thous/uL |
|---|---|---|---|---|---|---|---|
| 1 | G-CSF (Gen1) | I.M | 5 | 2 × 50 ug (four doses) | 50 | F. buffer | 840* |
| 2 | G-CSF (Gen1) | S.C | 5 | 2 × 50 ug (four doses) | 50 | F. buffer | 430 |
| 3 | G-CSF (Gen2) | I.M | 5 | 2 × 50 ug (four doses) | 50 | F. buffer | 746* |
| 4 | G-CSF (Gen2) | S.C | 5 | 2 × 50 ug (four doses) | 50 | F. buffer | 683 |
| 5 | Luc (Gen1) | I.M. | 5 | 2 × 50 ug (four doses) | 50 | F. buffer | 201 |
| 6 | Luc (Gen1) | S.C. | 5 | 2 × 50 ug (four doses) | 50 | F. buffer | 307 |
| 7 | Luc (Gen2) | I.M | 5 | 2 × 50 ug (four doses) | 50 | F. buffer | 336 |
| 8 | Luc (Gen2) | S.C | 5 | 2 × 50 ug (four doses) | 50 | F. buffer | 357 |
| 9 | F. Buffer | I.M | 4 | 0 (four doses) | 50 | F. buffer | 245 |
| 10 | F. Buffer | S.C. | 4 | 0 (four doses) | 50 | F. buffer | 509 |
| 11 | Untreated | — | 4 | | | — | 312 |

Example 26. Intravenous Administration

Human G-CSF mmRNA (mRNA sequence shown in SEQ ID NO: 4; poly-A tail of approximately 160 nucleotides not shown in sequence; 5' cap, Cap1) modified with 5-methylcytosine (5mc) and a pseudouridine (W) modification; or having no modifications and formulated in 10% lipoplex (RNAIMAX™) were delivered to mice at a dose of 50 ug RNA and in a volume of 100 ul via intravenous (IV) injection at days 0, 2 and 4. Neutrophils were measured at days 1, 5 and 8. Controls included non-specific mammalian RNA or the formulation buffer alone (F.Buffer). The mice were bled at days 1, 5 and 8 to determine the effect of mmRNA-encoded human G-CSF to increase neutrophil count. The dosing regimen is shown in Table 14 as are the resulting neutrophil counts (thousands/uL; K/uL).

For intravenous administration, the data reveal a four to five fold increase in neutrophil count above control at day 5 with G-CSF mmRNA but not with unmodified G-CSF mRNA or non-specific controls. Blood count returned to baseline four days after the final injection. No other changes in leukocyte populations were observed.

An asterisk indicates statistical significance at $p<0.001$ compared to buffer.

TABLE 14

Dosing Regimen

| Gr. | Treatment | N= | Dose Vol. (µl/mouse) | Dosing Vehicle | Neutrophil K/uL |
|---|---|---|---|---|---|
| 1 | G-CSF (Gen1) Day 1 | 5 | 100 | 10% lipoplex | 2.91 |
| 2 | G-CSF (Gen1) Day 5 | 5 | 100 | 10% lipoplex | 5.32* |
| 3 | G-CSF (Gen1) Day 8 | 5 | 100 | 10% lipoplex | 2.06 |
| 4 | G-CSF (no modification) Day 1 | 5 | 100 | 10% lipoplex | 1.88 |
| 5 | G-CSF (no modification) Day 5 | 5 | 100 | 10% lipoplex | 1.95 |
| 6 | G-CSF (no modification) Day 8 | 5 | 100 | 10% lipoplex | 2.09 |
| 7 | RNA Control Day 1 | 5 | 100 | 10% lipoplex | 2.90 |
| 8 | RNA Control Day 5 | 5 | 100 | 10% lipoplex | 1.68 |
| 9 | RNA Control Day 8 | 4 | 100 | 10% lipoplex | 1.72 |
| 10 | F. Buffer Day 1 | 4 | 100 | 10% lipoplex | 2.51 |
| 11 | F. Buffer Day 5 | 4 | 100 | 10% lipoplex | 1.31 |
| 12 | F. Buffer Day 8 | 4 | 100 | 10% lipoplex | 1.92 |

Example 27. Saline Formulation: Intramuscular Administration

Human G-CSF mmRNA (mRNA sequence shown in SEQ ID NO: 4; poly-A tail of approximately 160 nucleotides not shown in sequence; 5' cap, Cap 1) and human EPO mmRNA (mRNA sequence shown in SEQ ID NO: 7; poly-A tail of approximately 160 nucleotides not shown in sequence; 5' cap, Cap 1); G-CSF mmRNA (modified with 5-methylcytosine (5mc) and pseudouridine (Ψ)) and EPO mmRNA (modified with N1-5-methylcytosine (N1-5mc) and Ψ modification), were formulated in saline and delivered to mice via intramuscular (IM) injection at a dose of 100 ug.

Controls included Luciferase (IVT cDNA sequence shown in SEQ ID NO: 10) or the formulation buffer (F.Buffer). The mice were bled at 13 hours after the injection to determine the concentration of the human polypeptide in serum in pg/mL (G-CSF groups measured human G-CSF in mouse serum and EPO groups measured human EPO in mouse serum). The data are shown in Table 15.

TABLE 15

| Dosing Regimen | | | | | |
|---|---|---|---|---|---|
| Group | Treatment | N= | Dose Vol. (μl/mouse) | Dosing Vehicle | Average Protein Product pg/mL, serum |
| G-CSF | G-CSF | 5 | 50 | Saline | 19.8 |
| G-CSF | Luciferase | 5 | 50 | Saline | 0.5 |
| G-CSF | F. buffer | 5 | 50 | F. buffer | 0.5 |
| EPO | EPO | 5 | 50 | Saline | 191.5 |
| EPO | Luciferase | 5 | 50 | Saline | 15.0 |
| EPO | F. buffer | | | F. buffer | 4.8 |

Example 28. EPO Multi-Dose/Multi-Administration

Studies utilizing multiple intramuscular injection sites at one time point were designed and performed.

The design of a single multi-dose experiment involved using human erythropoietin (EPO) mmRNA (mRNA sequence shown in SEQ ID NO: 7; poly-A tail of approximately 160 nucleotides not shown in sequence; 5' cap, Cap1) or G-CSF (mRNA sequence shown in SEQ ID NO: 4; poly-A tail of approximately 160 nucleotides not shown in sequence; 5' cap, Cap 1) administered in saline. The dosing vehicle (F. buffer) was used as a control. The EPO and G-CSF mmRNA were modified with 5-methylcytosine at each cytosine and pseudouridine replacement at each uridine site.

Animals (n=5), Sprague-Dawley rats, were injected IM (intramuscular) for the single unit dose of 100 ug (delivered to one thigh). For multi-dosing 6 doses of 100 ug (delivered to two thighs) were used for both EPO and G-CSF mmRNA. Control dosing involved use of buffer at a single dose. Human EPO blood levels were evaluated 13 hours post injection.

Human EPO protein was measured in rat serum 13 hours post I.M. Five groups of rats were treated and evaluated. The results are shown in Table 16.

TABLE 16

| Multi-dose study | | | | |
|---|---|---|---|---|
| Group | Treatment | Dose of mmRNA | Total Dose | Avg. Pg/mL human EPO, serum |
| 1 | Human EPO mmRNA | 1 × 100 ug | 100 ug | 143 |
| 2 | Human EPO mmRNA | 6 × 100 ug | 600 ug | 256 |
| 3 | G-CSF mmRNA | 1 × 100 ug | 100 ug | 43 |
| 4 | G-CSF mmRNA | 6 × 100 ug | 600 ug | 58 |
| 5 | Buffer Alone | — | — | 20 |

Example 29. Signal Sequence Exchange Study

Several variants of mmRNAs encoding human Granulocyte colony stimulating factor (G-CSF) (mRNA sequence shown in SEQ ID NO: 4; poly-A tail of approximately 160 nucleotides not shown in sequence; 5' cap, Cap 1) were synthesized using modified nucleotides pseudouridine and 5-methylcytosine (pseudo-U/5mC). These variants included the G-CSF constructs encoding either the wild-type N terminal secretory signal peptide sequence (MAGPATQSPMKLMALQLLLWHSALWTVQEA; SEQ ID NO: 13), no secretory signal peptide sequence, or secretory signal peptide sequences taken from other mRNAs. These included sequences where the wild type GCSF signal peptide sequence was replaced with the signal peptide sequence of either: human α-1-anti trypsin (MMPSSVSWGILLLAGLCCLVPVSLA; SEQ ID NO: 14), human Factor IX (MQRVNMIMAESPSLITICLLGYLLSAECTVFLDHENANKILNRPKR; SEQ ID NO: 15), human Prolactin (MKGSLLLLLVSNLLLCQSVAP; SEQ ID NO: 16), or human Albumin (MKWVTFISLLFLFSSAYSRGVFRR; SEQ ID NO: 17).

250 ng of modified mRNA encoding each G-CSF variant was transfected into HEK293A (293A in the table), mouse myoblast (MM in the table) (C2C12, CRL-1772, ATCC) and rat myoblast (RM in the table) (L6 line, CRL-1458, ATCC) cell lines in a 24 well plate using 1 ul of Lipofectamine 2000 (Life Technologies), each well containing 300,000 cells. The supernatants were harvested after 24 hrs and the secreted G-CSF protein was analyzed by ELISA using the Human G-CSF ELISA kit (Life Technologies). The data shown in Table 17 reveal that cells transfected with G-CSF mmRNA encoding the Albumin signal peptide secrete at least 12 fold more G-CSF protein than its wild type counterpart.

TABLE 17

| Signal Peptide Exchange | | | |
|---|---|---|---|
| Signal peptides | 293A (pg/ml) | MM (pg/ml) | RM (pg/ml) |
| G-CSF Natural | 9650 | 3450 | 6050 |
| α-1-anti trypsin | 9950 | 5000 | 8475 |
| Factor IX | 11675 | 6175 | 11675 |
| Prolactin | 7875 | 1525 | 9800 |
| Albumin | 122050 | 81050 | 173300 |
| No Signal peptide | 0 | 0 | 0 |

Example 30. Cytokine Study: PBMC

PBMC isolation and Culture: 50 mL of human blood from two donors was received from Research Blood Components (lots KP30928 and KP30931) in sodium heparin tubes. For each donor, the blood was pooled and diluted to 70 mL with DPBS (SAFC Bioscience 59331C, lot 071M8408) and split evenly between two 50 mL conical tubes. 10 mL of Ficoll Paque (GE Healthcare 17-5442-03, lot 10074400) was gently dispensed below the blood layer. The tubes were centrifuged at 2000 rpm for 30 minutes with low acceleration and braking. The tubes were removed and the buffy coat PMBC layers were gently transferred to a fresh 50 mL conical and washed with DPBS. The tubes were centrifuged at 1450 rpm for 10 minutes.

The supernatant was aspirated and the PBMC pellets were resuspended and washed in 50 mL of DPBS. The tubes were centrifuged at 1250 rpm for 10 minutes. This wash step was repeated, and the PBMC pellets were resuspended in 19 mL of Optimem I (Gibco 11058, lot 1072088) and counted. The cell suspensions were adjusted to a concentration of 3.0× 10^6 cells/mL live cells.

These cells were then plated on five 96 well tissue culture treated round bottom plates (Costar 3799) per donor at 50 uL per well. Within 30 minutes, transfection mixtures were added to each well at a volume of 50 uL per well. After 4 hours post transfection, the media was supplemented with 10 μL of Fetal Bovine Serum (Gibco 10082, lot 1012368)

Transfection Preparation: mmRNA encoding human G-CSF (mRNA sequence shown in SEQ ID NO: 4; poly-A tail of approximately 160 nucleotides not shown in sequence; 5' cap, Cap1) (containing either (1) natural NTPs, (2) 100% substitution with 5-methyl cytidine and pseudouridine, or (3) 100% substitution with 5-methyl cytidine and N1-methyl pseudouridine; mmRNA encoding luciferase (IVT cDNA sequence shown in SEQ ID NO: 10) (containing either (1) natural NTPs or (2) 100% substitution with 5-methyl cytidine and pseudouridine) and TLR agonist R848 (Invivogen tlr1-r848) were diluted to 38.4 ng/uL in a final volume of 2500 uL Optimem I.

Separately, 432 μL of Lipofectamine 2000 (Invitrogen 11668-027, lot 1070962) was diluted with 13.1 mL Optimem I. In a 96 well plate nine aliquots of 135 μL of each mmRNA, positive control (R-848) or negative control (Optimem I) was added to 135 μL of the diluted Lipofectamine 2000. The plate containing the material to be transfected was incubated for 20 minutes. The transfection mixtures were then transferred to each of the human PBMC plates at 50 uL per well. The plates were then incubated at 37 C. At 2, 4, 8, 20, and 44 hours each plate was removed from the incubator, and the supernatants were frozen.

After the last plate was removed, the supernatants were assayed using a human G-CSF ELISA kit (Invitrogen KHC2032) and human IFN-alpha ELISA kit (Thermo Scientific 41105-2). Each condition was done in duplicate.

Results: The ability of unmodified and modified mRNA (mmRNAs) to produce the encoded protein was assessed (G-CSF production) over time as was the ability of the mRNA to trigger innate immune recognition as measured by interferon-alpha production. Use of in vitro PBMC cultures is an accepted way to measure the immunostimulatory potential of oligonucleotides (Robbins et al., Oligonucleotides 2009 19:89-102).

Results were interpolated against the standard curve of each ELISA plate using a four parameter logistic curve fit. Shown in Tables 18 and 19 are the average from 2 separate PBMC donors of the G-CSF and IFN-alpha production over time as measured by specific ELISA.

In the G-CSF ELISA, background signal from the Lipofectamine 2000 untreated condition was subtracted at each timepoint. The data demonstrated specific production of human G-CSF protein by human peripheral blood mononuclear is seen with G-CSF mRNA containing natural NTPs, 100% substitution with 5-methyl cytidine and pseudouridine, or 100% substitution with 5-methyl cytidine and N1-methyl pseudouridine. Production of G-CSF was significantly increased through the use of modified mRNA relative to unmodified mRNA, with the 5-methyl cytidine and N1-methyl pseudouridine containing G-CSF mmRNA showing the highest level of G-CSF production. With regards to innate immune recognition, unmodified mRNA resulted in substantial IFN-alpha production, while the modified mRNA largely prevented interferon-alpha production.

TABLE 18

G-CSF Signal
G-CSF signal - 2 Donor Average

| pg/mL | 2 Hr | 4 Hr | 8 Hr | 20 Hr | 44 Hr |
|---|---|---|---|---|---|
| G-CSF (5 mC/pseudouridine) | 120.3 | 136.8 | 421.0 | 346.1 | 431.8 |
| G-CSF (5 mC/N1-methyl pseudouridine) | 256.3 | 273.7 | 919.3 | 1603.3 | 1843.3 |
| GCSF(Natural-no modification) | 63.5 | 92.6 | 129.6 | 258.3 | 242.4 |
| Luciferase (5 mC/pseudouridine) | 4.5 | 153.7 | 33.0 | 186.5 | 58.0 |

TABLE 19

IFN-alpha signal
IFN-alpha signal - 2 donor average

| pg/mL | 2 Hr | 4 Hr | 8 Hr | 20 Hr | 44 Hr |
|---|---|---|---|---|---|
| G-CSF (5 mC/pseudouridine) | 21.1 | 2.9 | 3.7 | 22.7 | 4.3 |
| G-CSF (5 mC/N1-methyl pseudouridine) | 0.5 | 0.4 | 3.0 | 2.3 | 2.1 |
| G-CSF(Natural) | 0.0 | 2.1 | 23.3 | 74.9 | 119.7 |
| Luciferase (5 mC/pseudouridine) | 0.4 | 0.4 | 4.7 | 1.0 | 2.4 |
| R-848 | 39.1 | 151.3 | 278.4 | 362.2 | 208.1 |
| Lipofectamine 2000 control | 0.8 | 17.2 | 16.5 | 0.7 | 3.1 |

Example 31. Quantification in Exosomes

The quantity and localization of the mmRNA of the present invention can be determined by measuring the amounts (initial, timecourse, or residual basis) in isolated exosomes. In this study, since the mmRNA are typically codon-optimized and distinct in sequence from endogenous mRNA, the levels of mmRNA are quantitated as compared to endogenous levels of native or wild type mRNA by using the methods of Gibbings, PCT/IB2009/005878, the contents of which are incorporated herein by reference in their entirety.

In these studies, the method is performed by first isolating exosomes or vesicles preferably from a bodily fluid of a patient previously treated with a polynucleotide, primary construct or mmRNA of the invention, then measuring, in said exosomes, the polynucleotide, primary construct or mmRNA levels by one of mRNA microarray, qRT-PCR, or other means for measuring RNA in the art including by suitable antibody or immunohistochemical methods.

Example 32: Bifunctional mmRNA

Using the teachings and synthesis methods described herein, modified RNAs are designed and synthesized to be bifunctional, thereby encoding one or more cytotoxic protein molecules as well as be synthesized using cytotoxic nucleosides.

Administration of the bifunctional modified mRNAs is effected using either saline or a lipid carrier. Once administered, the bifunctional modified mRNA is translated to produce the encoded cytotoxic peptide. Upon degradation of the delivered modified mRNA, the cytotoxic nucleosides are released which also effect therapeutic benefit to the subject.

Example 33. Synthesis of Modified mRNA

Modified mRNA is generated from a cDNA template containing a T7 RNA-polymerase promoter sequence using a commercially available T7 RNA polymerase transcription kit (MEGASCRIPT® High Yield Transcription KIT, AMBION®, Austin, TX; MSCRIPT™ mRNA Production Kit, EPICENTRE® Biotechnologies, Madison, WI). An in vitro transcription reaction contains between 1-2 g of template DNA in the form of a linearized plasmid, PCR product, or single-stranded oligonucleotide with a double-stranded polymerase promoter region. The template DNA encodes a strong translation initiation sequence such as a strong consensus Kozak sequence or an optimized, high-expression IRES including the EMCV IRES. Reaction volumes are between 20-40 μl and contain 3'-O-Me-$m^7$-G(5')ppp(5')G ARCA cap analog (NEW ENGLAND BIOLABS®) in addition to an optimized ribonucleotide mixture of determined modified adenine, guanine, cytidine and uridine ribonucleotide analogs. Final reaction concentrations for nucleotide are 6 mM for the cap analog and 1.5-7.5 mM for each of the other nucleotides. The temperature and duration of the in vitro transcription reaction are optimized for efficiency, fidelity and yield. Reactions may be incubated from 3-6 hours and up to 16 hours at 37° C. Following the in vitro transcription reaction, the capped mRNA undergoes polyadenylation using a commercially available poly-A tailing kit (EPICENTRE® Biotechnologies, Madison, WI). The resulting capped and polyadenylated synthetic mRNA is then purified by denaturing agarose gel electrophoresis to confirm production of full-length product and to remove any degradation products followed by spin column filtration (RNeasy Kit, Qiagen, Valencia, CA; MEGACLEAR™ AMBION®, Austin, TX). Purified synthetic mRNAs are resuspended in RNase-free water containing an RNase inhibitor (RNASIN® Plus RNase Inhibitor, Promega, Madison, WI), quantified by NANODROP™ (Thermo Scientific, Logan, UT) and stored at −20° C.

Example 34: Bulk Transfection of Modified mRNA into Cell Culture

A. Cationic Lipid Delivery Vehicles

RNA transfections are carried out using RNAIMax (Invitrogen, Carlsbad, CA) or TRANSIT-mRNA (Mirus Bio, Madison, WI) cationic lipid delivery vehicles. RNA and reagent are first diluted in Opti-MEM basal media (Invitrogen, Carlsbad, CA). 100 ng/uL RNA is diluted 5× and 5 μL of RNAIMax per g of RNA is diluted 10×. The diluted components are pooled and incubated 15 minutes at room temperature before they are dispensed to culture media. For TRANSIT-mRNA transfections, 100 ng/uL RNA is diluted 10× in Opti-MEM and BOOST reagent is added (at a concentration of 2 μL per g of RNA), TRANSIT-mRNA is added (at a concentration of 2 μL per g of RNA), and then the RNA-lipid complexes are delivered to the culture media after a 2-minute incubation at room temperature. RNA transfections are performed in Nutristem xenofree hES media (STEMGENT®, Cambridge, MA) for RiPS derivations, Dermal Cell Basal Medium plus Keratinocyte Growth Kit (ATCC) for keratinocyte experiments, and Opti-MEM plus 2% FBS for all other experiments. Successful introduction of a modified mRNA (mmRNA) into host cells can be monitored using various known methods, such as a fluorescent marker, such as Green Fluorescent Protein (GFP). Successful transfection of a modified mRNA can also be determined by measuring the protein expression level of the target polypeptide by e.g., Western Blotting or immunocytochemistry. Similar methods may be followed for large volume scale-up to multi-liter (5-10,000 L) culture format following similar RNA-lipid complex ratios.

B. Electroporation Delivery of Exogenous Synthetic mRNA Transcripts

Electroporation parameters are optimized by transfecting MRC-5 fibroblasts with in vitro synthetic modified mRNA (mmRNA) transcripts and measuring transfection efficiency by quantitative RT-PCR with primers designed to specifically detect the exogenous transcripts. Discharging a 150 uF capacitor charged to F into $2.5\times10^6$ cells suspended in 50 μl of Opti-MEM (Invitrogen, Carlsbad, CA) in a standard electroporation cuvette with a 2 mm gap is sufficient for repeated delivery in excess of 10,000 copies of modified mRNA transcripts per cell, as determined using the standard curve method, while maintaining high viability (>70%). Further experiments may reveal that the voltage required to efficiently transfect cells with mmRNA transcripts can depend on the cell density during electroporation. Cell density may vary from $1\times10^6$ cell/50 μl to a density of $2.5\times10^6$ cells/50 μl and require from 110V to 145V to transfect cells with similar efficiencies measured in transcript copies per cell. Large multi-liter (5-10,000 L) electroporation may be performed similar to large volume flow electroporation strategies similar to methods described with the above described constraints (Li et al., 2002; Geng et al., 2010).

Example 35. Overexpression of Ceramide Transfer Protein to Increase Therapeutic Antibody Protein Production in Established CHO Cell Lines A. Batch Culture An antibody producing CHO cell line (CHO DG44) secreting a humanized therapeutic IgG antibody is transfected a single time with lipid cationic delivery agent alone (control) or a synthetic mRNA transcript encoding wild type ceramide transfer protein (CERT) or a non-phosphorylation competent Ser132A CERT mutant. The sequences are taught in for example, U.S. Ser. No. 13/252,049, the contents of which are incorporated herein by reference in their entirety. CERT is an essential cytosolic protein in mammalian cells that transfers the sphingolipid ceramide from the endoplasmic reticulum to the Golgi complex where it is converted to sphingomyelin (Hanada et al., 2003). Overexpression of CERT significantly enhances the transport of secreted proteins to the plasma membrane and improves the production of proteins that are transported via the secretory pathway from eukaryotic cells thereby enhancing secretion of proteins in the culture medium. Synthetic mRNA transcripts are pre-mixed with a lipid cationic delivery agent at a 2-5:1 carrier:RNA ratio. The initial seeding density is about $2\times10^5$ viable cells/mL. The synthetic mRNA transcript is delivered after initial culture seeding during the exponential culture growth phase to achieve a final synthetic mRNA copy number between $10\times10^2$ and $10\times10^3$ per cell. The basal cell culture medium used for all phases of cell inoculum generation and for growth of cultures in bioreactors was modified CD-CHO medium containing glutamine, sodium bicarbonate, insulin and methotrexate. The pH of the medium was adjusted to 7.0 with 1 N HCl or 1N NaOH after addition of all components. Culture run times ended on days 7, 14, 21 or 28+. Production-level 50 L scale reactors (stainless steel reactor with two marine impellers) were used and are scalable to >10,000 L stainless steel reactors (described in commonly-assigned patent application U.S. Ser. No. 60/436,050, filed Dec. 23, 2002, and U.S. Ser. No. 10/740,645). A data acquisition system (Intellution Fix 32, OSlsoft, LLC, San Leandro, CA) recorded temperature, pH, and dissolved oxygen (DO) throughout runs. Gas flows were controlled via rotameters. Air was sparged into the reactor via a submerged frit (5 m pore size) and through the reactor head space for $CO_2$ removal. Molecular oxygen was sparged through the same frit for DO control. $CO_2$ was sparged through same frit as used for pH control. Samples of cells were removed from the reactor on a daily basis. A sample used for cell counting was stained with trypan blue (Sigma, St. Louis, MO). Cell count and cell viability determination were performed via hemocytometry using a microscope. For analysis of metabolites, additional samples were centrifuged for 20 minutes at 2000 rpm (4° C.) for cell separation. Supernatant was analyzed for the following parameters: titer, sialic acid, glucose, lactate, glutamine, glutamate, pH, $pO_2$, $pCO_2$, ammonia, and, optionally, lactate dehydrogenase (LDH). Additional back-up samples were frozen at −20° C. To measure secreted humanized IgG antibody titers, supernatant is taken from seed-stock cultures of all stable cell pools, the IgG titer is determined by ELISA and divided by the mean number of cells to calculate the specific productivity. The highest values are the cell pools with the Ser132A CERT mutant, followed by wild type CERT. In both, IgG expression is markedly enhanced compared to carrier-alone or untransfected cells.

Continuous or Batch-Fed Culture

An antibody producing CHO cell line (CHO DG44) secreting humanized IgG antibody is transfected with lipid cationic delivery agent alone (control) or a synthetic mRNA transcript encoding wild type ceramide transfer protein or a non-phosphorylation competent Ser132A CERT mutant. Synthetic mRNA transcripts are pre-mixed with a lipid cationic delivery agent at a 2-5:1 carrier:RNA ratio. The initial seeding density was about $2\times10^5$ viable cells/mL. Synthetic mRNA transcript is delivered after initial culture seeding during the exponential culture growth phase to achieve a final synthetic mRNA copy number between $10\times10^2$ and $10\times10^3$ per cell. The basal cell culture medium used for all phases of cell inoculum generation and for growth of cultures in bioreactors was modified CD-CHO medium containing glutamine, sodium bicarbonate, insulin and methotrexate. The pH of the medium was adjusted to 7.0 with 1 N HCl or 1N NaOH after addition of all components. Bioreactors of 5 L scale (glass reactor with one marine impeller) were used to obtain maximum CERT protein production and secreted humanized IgG antibody curves. For continuous or fed-batch cultures, the culturing run time is increased by supplementing the culture medium one or more times daily (or continuously) with fresh medium during the run. In the a continuous and fed-batch feeding regimens, the cultures receive feeding medium as a continuously-supplied infusion, or other automated addition to the culture, in a timed, regulated, and/or programmed fashion so as to achieve and maintain the appropriate amount of synthetic mRNA:carrier in the culture. The preferred method is a feeding regimen of a once per day bolus feed with feeding medium containing synthetic mRNA:carrier on each day of the culture run, from the beginning of the culture run to the day of harvesting the cells. The daily feed amount was recorded on batch sheets. Production-level 50 L scale reactors (stainless steel reactor with two marine impellers) were used and are scalable to >10,000 L stainless steel reactors. A data acquisition system (Intellution Fix 32) recorded temperature, pH, and dissolved oxygen (DO) throughout runs. Gas flows were controlled via rotameters. Air was sparged into the reactor via a submerged frit (5 m pore size) and through the reactor head space for $CO_2$ removal. Molecular oxygen was sparged through the same frit for DO control. $CO_2$ was sparged through same frit as used for pH control. Samples of cells were removed from the reactor on a daily basis. A sample used for cell counting was stained with trypan blue (Sigma, St. Louis, Mo.). Cell count and cell viability determination were performed via hemocytometry using a microscope. For analysis of metabolites, additional samples were centrifuged for 20 minutes at 2000 rpm (4° C.) for cell separation. Supernatant was analyzed for the following parameters: titer, sialic acid, glucose, lactate, glutamine, glutamate, pH, $pO_2$, $pCO_2$, ammonia, and, optionally, lactate dehydrogenase (LDH). Additional back-up samples were frozen at −20° C. To measure secreted humanized IgG antibody titers, supernatant is taken from seed-stock cultures of all stable cell pools, the IgG titer is determined by ELISA and divided by the mean number of cells to calculate the specific productivity. The highest values are the cell pools with the Ser132A CERT mutant, followed by wild type CERT. In both, IgG expression is markedly enhanced compared to carrier-alone or untransfected cells.

Example 36. De Novo Generation of a Mammalian Cell Line Expressing Human Erythropoietin as a Therapeutic Agent A. Batch Culture This Example describes the production of human erythropoietin protein (EPO) from cultured primary CHO cells. Erythropoietin is a glycoprotein hormone that is required for red blood cell synthesis. EPO protein may be used as a therapeutic agent for anemia from cancer, heart failure, chronic kidney disease and myelodysplasia. Primary CHO cells are isolated and cultured as described (Tjio and Puck, 1958). Primary CHO cells were then expanded in modified CD-CHO medium containing glutamine, sodium bicarbonate, insulin, and methotrexate (see Example 35) using T-75 flasks (Corning, Corning, N.Y.) and 250 and 500 mL spinners (Bellco, Vineland, N.J.). T-flasks and spinners were incubated at 37° C. in 6% $CO_2$. After sufficient inoculum was generated, the culture was transferred into a either a 5 L or a 50 L bioreactor as described above (see Example 35). Synthetic mRNA transcript encoding the human erythropoietin protein are pre-mixed with a lipid cationic delivery agent at a 2-5:1 carrier:RNA ratio in a minimum of 1% total culture volume. The initial seeding density is about $2\times10^5$ viable cells/mL. The synthetic mRNA transcript is delivered after initial culture seeding during the exponential culture growth phase to achieve a final synthetic mRNA copy number between $10\times10^2$ and $10\times10^3$ per cell. Culture growth and analysis were performed as described above (see Example 34).

B. Continuous or Batch-Fed Culture

A primary CHO cell line derived and expanded as described above (see Example 36a) is transfected with lipid cationic delivery agent alone (control) or a synthetic mRNA transcript encoding human erythropoietin protein. Synthetic mRNA transcripts are pre-mixed with a lipid cationic delivery agent at a 2-5:1 carrier:RNA ratio. The initial seeding density was about $2\times10^5$ viable cells/mL. Synthetic mRNA transcript is delivered after initial culture seeding during the exponential culture growth phase to achieve a final synthetic mRNA copy number between $10\times10^2$ and $10\times10^3$ per cell. Culture conditions were as described above (Example 35a). For continuous or fed-batch cultures, the culturing run time is increased by supplementing the culture medium one or more times daily (or continuously) with fresh medium during the run. In the a continuous and fed-batch feeding regimens, the cultures receive feeding medium as a continuously-supplied infusion, or other automated addition to the culture, in a timed, regulated, and/or programmed fashion so as to achieve and maintain the appropriate amount of synthetic mRNA:carrier in the culture. The preferred method is a feeding regimen of a once per day bolus feed with feeding medium containing synthetic mRNA:carrier on each day of the culture run, from the beginning of the culture run to the day of harvesting the cells. The daily feed amount was recorded on batch sheets. Production-level 50 L scale reactors (stainless steel reactor with two marine impellers) were used and are scalable to >10,000 L stainless steel reactors. Culture growth and analysis were performed as described herein (see Example 35).

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A messenger ribonucleic acid (mRNA) wherein 100% of uridines in the mRNA are replaced with N1-methyl-pseudouridine.

2. A pharmaceutical composition comprising a messenger ribonucleic acid (mRNA) wherein 100% of uridines in the mRNA are replaced with N1-methyl-pseudouridine.

* * * * *